US011168064B2

(12) United States Patent
Evans et al.

(10) Patent No.: US 11,168,064 B2
(45) Date of Patent: Nov. 9, 2021

(54) SYNTHESIS OF THAPSIGARGIN, NORTRILOBOLIDE, AND ANALOGS THEREOF

(71) Applicant: Queen's University at Kingston, Kingston (CA)

(72) Inventors: P. Andrew Evans, Kingston (CA); Dezhi Chen, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 16/496,688

(22) PCT Filed: Mar. 27, 2018

(86) PCT No.: PCT/CA2018/050369
§ 371 (c)(1),
(2) Date: Sep. 23, 2019

(87) PCT Pub. No.: WO2018/176133
PCT Pub. Date: Oct. 4, 2018

(65) Prior Publication Data
US 2020/0031793 A1 Jan. 30, 2020

Related U.S. Application Data

(60) Provisional application No. 62/477,118, filed on Mar. 27, 2017.

(51) Int. Cl.

| | |
|---|---|
| ***C07D 307/93*** | (2006.01) |
| ***A61K 47/64*** | (2017.01) |
| ***C07C 45/63*** | (2006.01) |
| ***C07C 67/31*** | (2006.01) |
| ***C07F 7/18*** | (2006.01) |

(52) U.S. Cl.
CPC ............ *C07D 307/93* (2013.01); *A61K 47/64* (2017.08); *C07C 45/63* (2013.01); *C07C 67/31* (2013.01); *C07F 7/188* (2013.01); *C07F 7/1892* (2013.01)

(58) Field of Classification Search
None
See application file for complete search history.

(56) References Cited

PUBLICATIONS

International Search Report and Written Opinion for correspondending International patent application No. PCT/CA2018/050369 filed on Mar. 27, 2018.
Chu, H., et al., "Scalable Synthesis of (—)-Thapsigargin", ACS Central Science, vol. 3(1), pp. 47-51, (2017).
Crestey, F., et al., "Concise Synthesis of thapsigargin from nortrilobolide". Tetrahedron Letters, vol. 56, pp. 5896-5898, (2015).
Christensen, S.B., et al., "Structure of Histamine Releasing Guaianolides from Thapsia Species", Phytochemistry, vol. 23, No. 8. pp. 1659-1663, (1984).
De Pascual Teresa, J. et al., "Phenylpropanoids and Other Derivatives from Thapsia Villosa" Phytochemistry, vol. 24, No. 9, pp. 2071-2074, (1985).

*Primary Examiner* — Samantha L Shterengarts
(74) *Attorney, Agent, or Firm* — Angela Lyon

(57) ABSTRACT

The present invention relates to the preparation of compounds of Formula I, including thapsigargin, nortrilobolide and 8-O-debutanoyl-thapsigargin from commercially available (R)-(−)-carvone via synthetic intermediate compound of formula 12 by pinacol coupling and in situ lactonization.

I

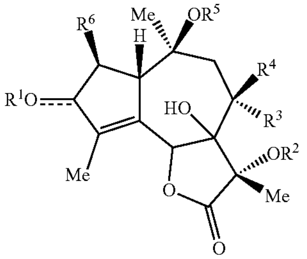

12

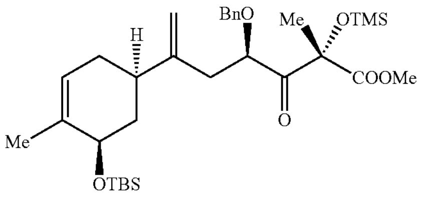

26 Claims, 5 Drawing Sheets thapsigargin (1)

nortrilobolide (3)

MIPSAGARGIN® (5)

thapsigargin (1)

6
common Synthetic Intermediate nortrilobolide (3)

6

7

9

8
E = $CO_2Me$ (R)-(−)-Carvone (10)

*thapsigargin (1)*

(R)-(−)-Carvone (10)

SI-01

11

9

12

8

E = $CO_2Me$

7

13

14

6

17

Ar = 2,4,6-$Cl_3C_6H_2$

18 nortrilobolide (3)

(*R*)-(−)-Carvone (10)
SI-01
11
9
12
8
E = $CO_2Me$
7
13
14
19
17
Ar = 2,4,6-$Cl_3C_6H_2$
20
21
22

SYNTHESIS OF THAPSIGARGIN, NORTRILOBOLIDE, AND ANALOGS THEREOF

RELATED APPLICATIONS

This application claims the benefit of the filing date of U.S. Provisional Patent Application No. 62/477,118, filed on Mar. 27, 2017, the contents of which are incorporated herein by reference in their entirety.

FIELD

The field pertains to synthesis of natural products. Specifically, the field is the synthesis of a particular family of terpenes, known as the thapsigargins, which are sesquiterpene lactones

BACKGROUND

Terpenes are a large and diverse class of natural products, which are produced by a variety of plants (e.g., conifers), and by some insects (e.g., termites, swallowtail butterflies). Their diversity stems from structural and stereochemical diversity. Of these, a particular terpene compound, thapsigargin (1), was first isolated from Mediterranean plant *Thapsia garganica* L. in 1978 (Rasmussen U. at al. *Acta. Pharm. Suec.* 1978, 15:133-140). This compound, together with structurally-related guaianolides, are collectively known as a family of compounds termed "thapsigargins". For example, nortrilobolide (3), which only differs from thapsigargin (1) at C-2 position, was isolated from the plant *Thapsia garganica* L by Christensen in 1991 (U. W. Smitt, at al., *Planta Med.* 1991, 57: 196-197). Terpenes have played significant roles as pesticides in agriculture, as fragrances in cosmetics, and as chemotherapeutic agents in human disease therapy and prevention. Their use has been restricted by limited natural sources, low natural abundance, and difficulties associated with their chemical syntheses on a preparative scale.

SUMMARY

In one aspect, the invention provides a method for synthesizing a compound of Formula I or a pharmaceutically acceptable salt thereof, wherein Formula I is:

I

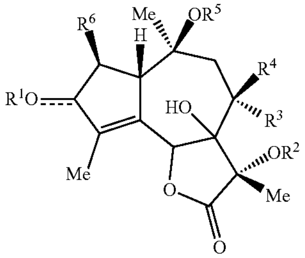

wherein $R^1$ is H, an acyl, aryl, or aliphatic group, or may not be present;

$R^2$ is H, acyl, aryl, aliphatic, or a hydroxyl protecting group;

$R^3$ and $R^4$ are independently H or acyloxy, alkoxyl, or OP wherein P is a hydroxyl protecting group;

$R^5$ is H or an acyl or aliphatic group;

$R^6$ is H or an acyloxy or alkoxy group:

carbon moieties within acyl, acyloxy, alkyl and alkoxy groups are aliphatic or aryl and may be substituted or unsubstituted; and a dotted line represents a bond that may or may not be present, the method comprising subjecting a reactant to a series of chemical reactions that produce synthetic intermediates including an alkylation to produce compound 12

12

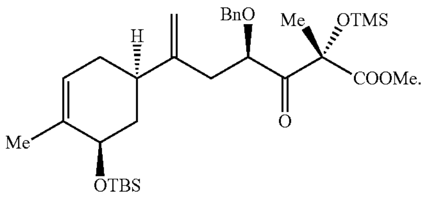

In one embodiment, the compound of Formula I is a compound of Formula IA or Formula IB:

Formula IA

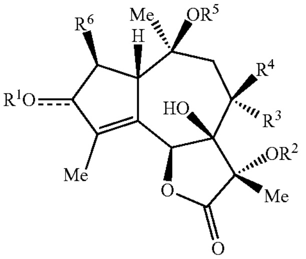

Formula IB

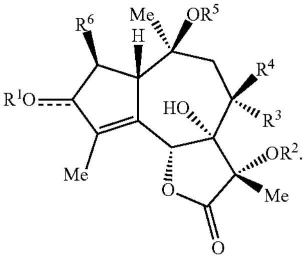

In one embodiment, the compound of Formula IA comprises:

thapsigargin, thapsigargicin, thapsitranstagin, 2-acetoxytrilobolide, thapsivillosin A, thapsivillosin B, thapsivillosin C, thapsivillosin D, thapsivillosin E, thapsivillosin H, thapsivillosin G, thapsivillosin H, thapsivillosin I, thapsivillosin J, thapsivillosin L, thapsivillosin F, trilobolide, or nortrilobolide -continued
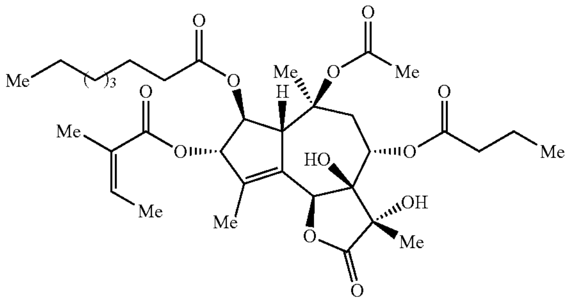
Thapsigargin
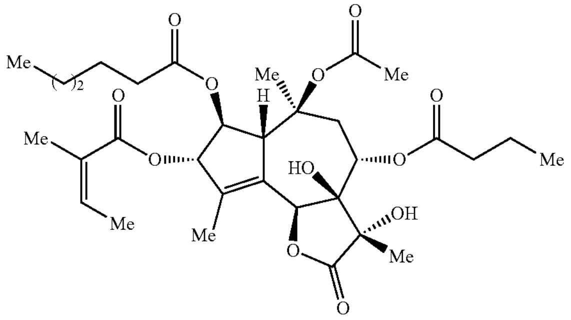
Thapsigargicin
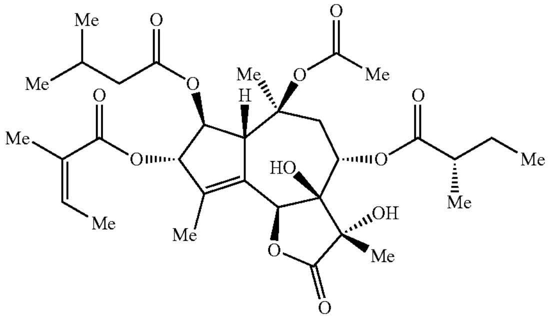
Thapsitranstagin
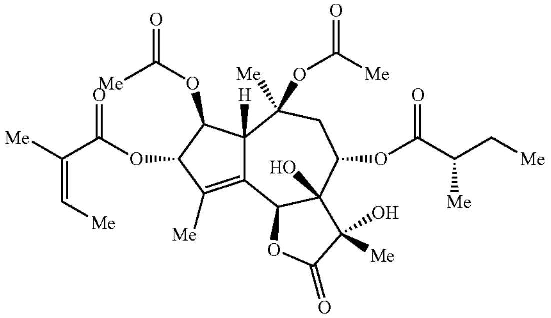
2-Acetoxytrilobolide
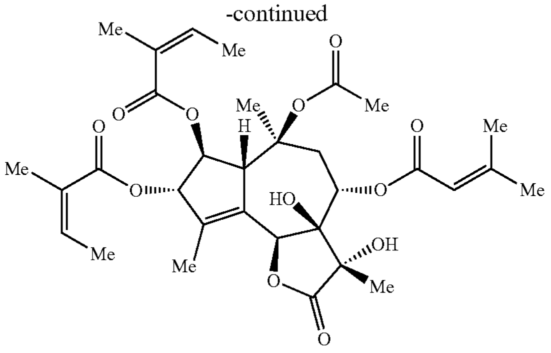
Thapsivillosin A
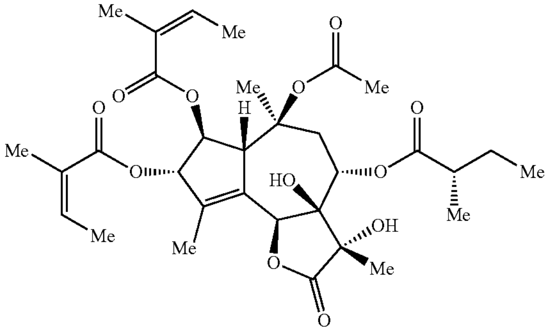
Thapsivillosin B
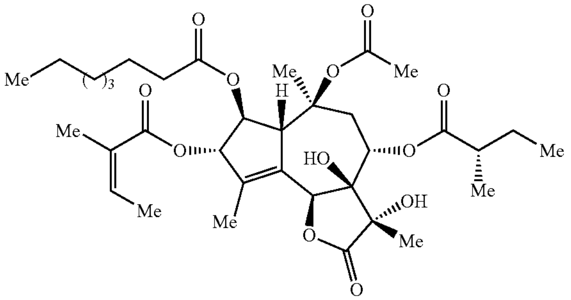
Thapsivillosin C
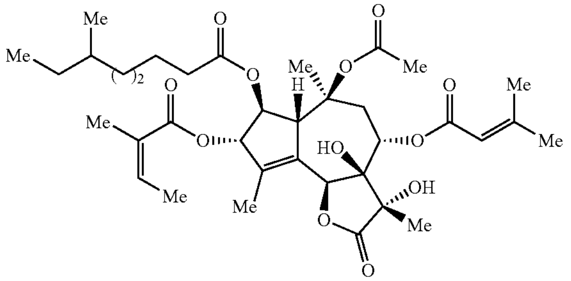
Thapsivillosin D
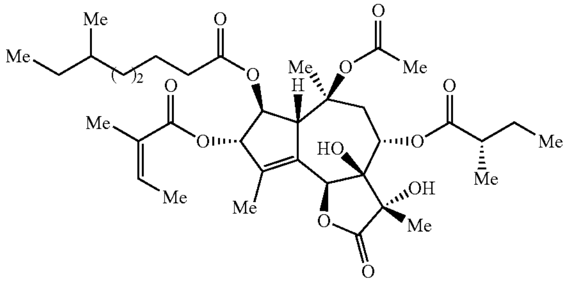
Thapsivillosin E -continued
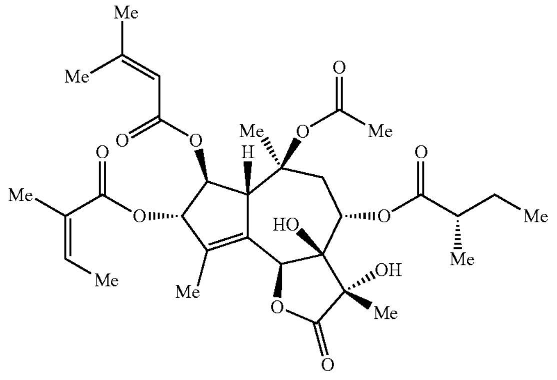
Thapsivillosin H
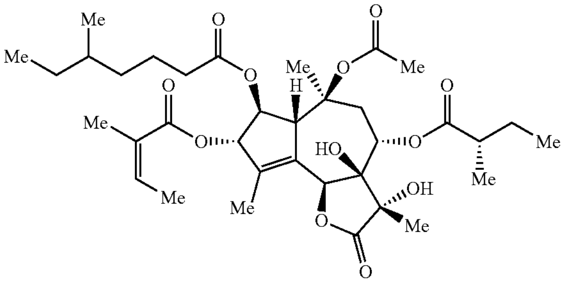
Thapsivillosin G
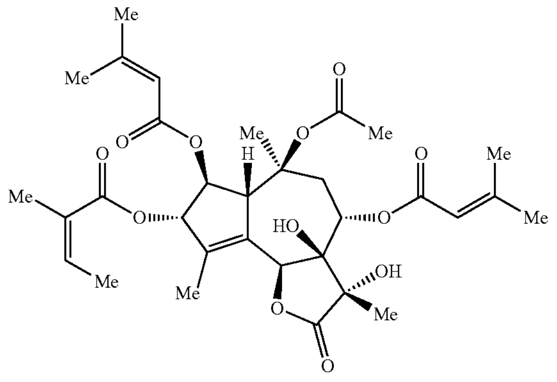
Thapsivillosin H
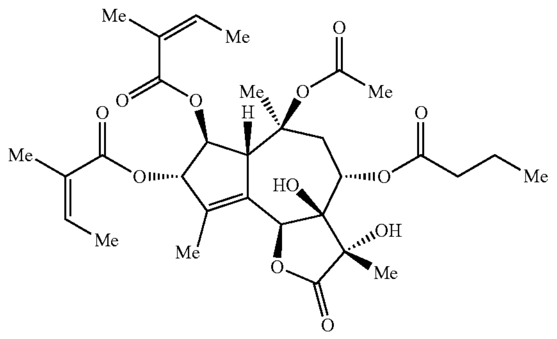
Thapsivillosin I
-continued
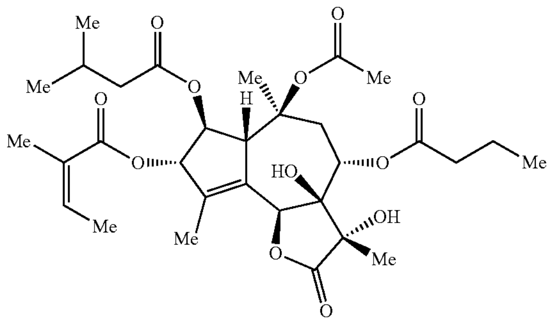
Thapsivillosin J
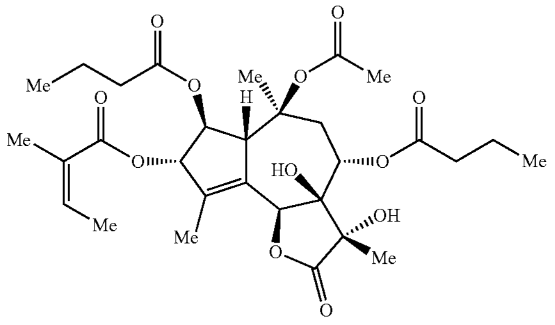
Thapsivillosin L
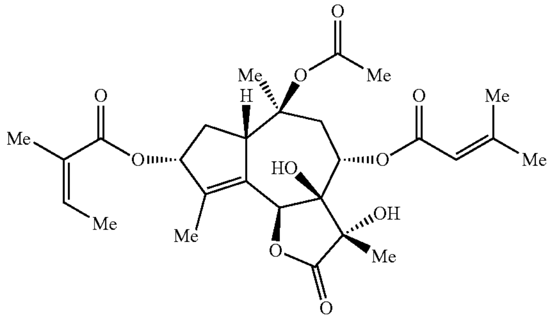
Thapsivillosin F
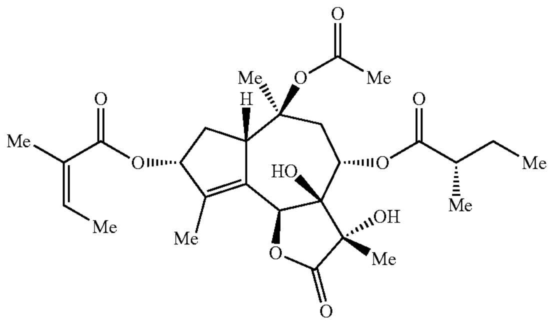
Trilobolide -continued

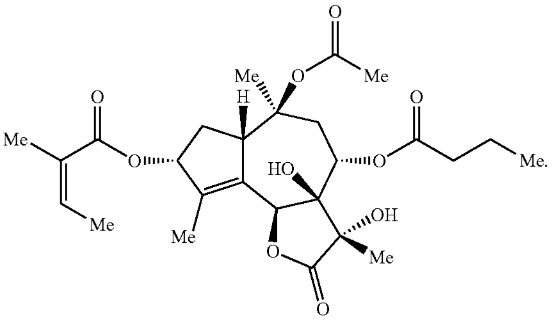

Nortrilobolide

In one embodiment, the compound of Formula IB comprises compound DC-22-042

DC-22-042

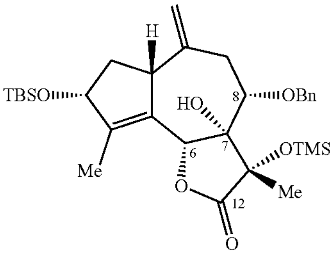

(3S,3aS,4S,6aR,8R,9bR)-4-(Benzyloxy)-8-((tert-butyldimethylsilyl)oxy)-3a-hydroxy-3,9-dimethyl-6-methylene-3-((trimethylsilyl)oxy)-3,3a,4,5,6,6a,7,8-octahydroazuleno[4,5-b]furan-2(9bH)-one In one embodiment, the compound of Formula I is thapsigargin (1)

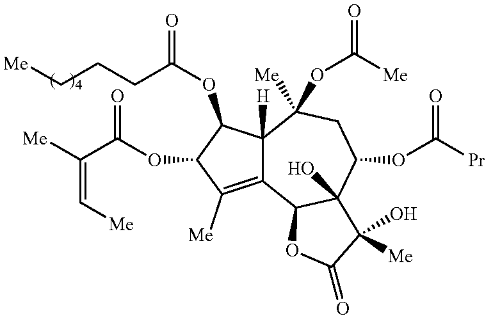

thapsigargin (1)

or a pharmaceutically acceptable salt thereof. In one embodiment, the reactant is (R)-(−)-carvone (10). In one embodiment the method further includes reacting a reactant in a series of chemical reactions that produce synthetic intermediates that include compound 7

7

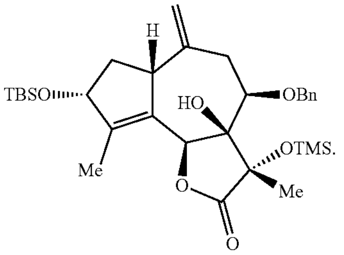

In one embodiment, the method further includes reacting a reactant in a series of chemical reactions that produce synthetic intermediates that include compound 8

8

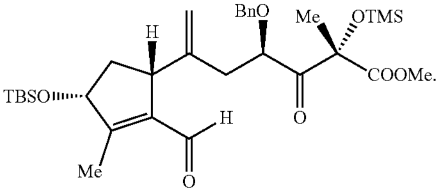

In one embodiment, the method includes steps to produce compounds 12, 7 and 8. In one embodiment, the method further includes reacting a reactant in a series of chemical reactions that produce synthetic intermediates that include compound 13

13

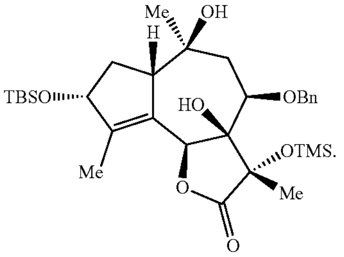

In one embodiment, the method further includes reacting a reactant in a series of chemical reactions that produce synthetic intermediates that include compound 14

14

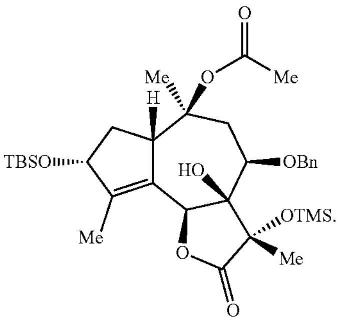

In one embodiment, the method includes steps to produce compound 14. In one embodiment, the method further includes reacting a reactant in a series of chemical reactions that produce synthetic intermediates that include compound 15

15

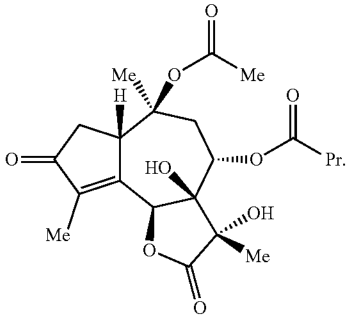

In one embodiment, the method further includes reacting a reactant in a series of chemical reactions that produce synthetic intermediates that include compound 16

16

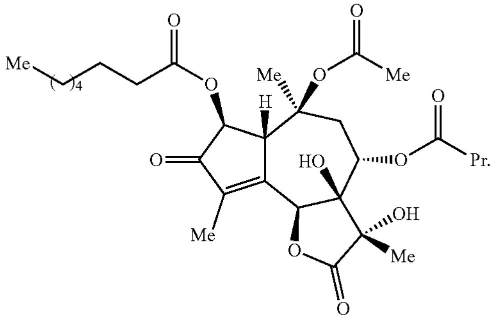

In one embodiment, the method further includes reacting a reactant in a series of chemical reactions that produce synthetic intermediates that include compound SI-04

SI-04

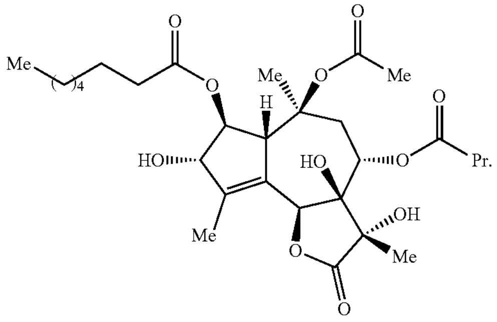

In one embodiment, the compound of Formula I is thapsigargin (1) or a pharmaceutically acceptable salt thereof, comprising the steps of:

Step 1) converting of (R)-(−)-carvone (10) to compound SI-01 by allylic halogenation;

Step 2) converting compound SI-01 to compound 11 by reduction and in situ protection;

Step 3) coupling compound 11 and compound 9 to form compound 12 by asymmetric alkylation;

Step 4) converting compound 12 to compound 8 by selective ozonolysis followed by in situ aldol condensation and dehydration;

Step 5) converting compound 8 to compound 7 by pinacol coupling and in situ lactonization;

Step 6) converting compound 7 to compound 13 by hydration;

Step 7) converting compound 13 to compound 14 by acylation;

Step 8) converting compound 14 to compound 6 by deprotection, oxidation, and reduction;

Step 9) converting compound 6 to compound 15 by acylation and oxidation;

Step 10) converting compound 15 to compound 16 by oxidation;

Step 11) converting compound 16 to compound SI-04 by reduction; and

Step 12) converting compound SI-04 to thapsigargin (1) by acylation

Si-01

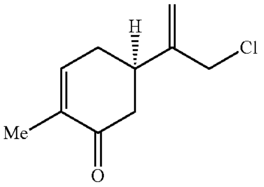

6

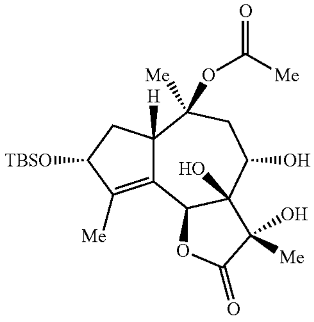

7

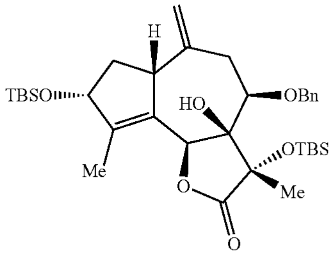

8

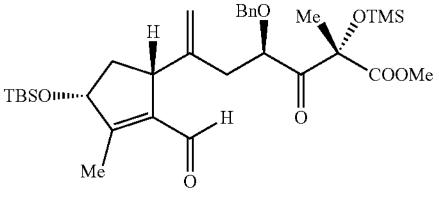

-continued

9

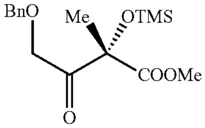

10

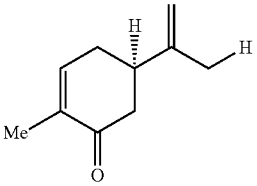

11

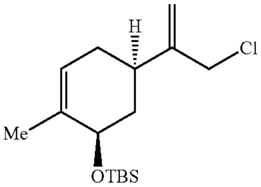

12

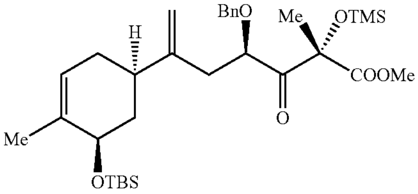

13

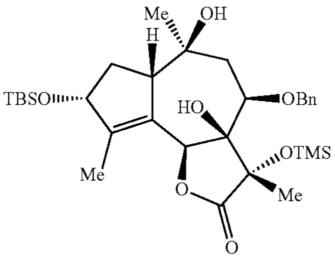

14

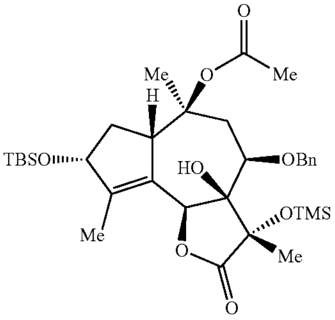

-continued

15

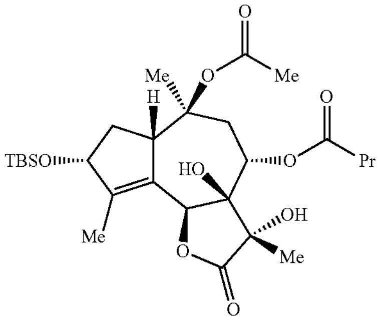

16

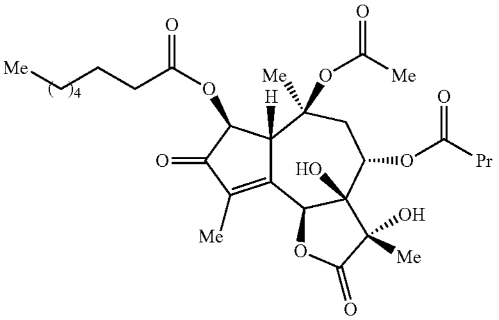

Si-04

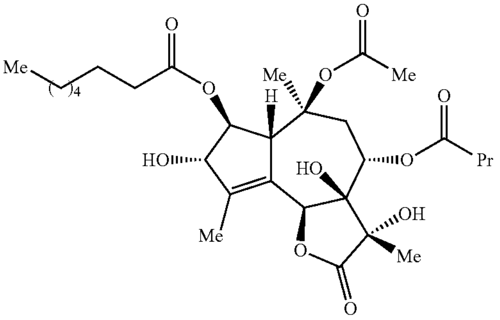

(1)

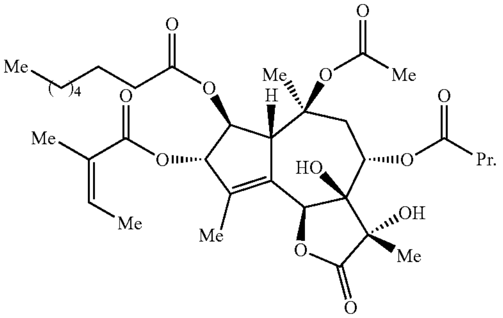

Thapsigargin

In one embodiment, the compound of Formula I is nortrilobolide (3) or a pharmaceutically acceptable salt thereof, comprising the steps of:

Step 1) converting (R)-(−)-carvone (10) to compound SI-01 by allylic halogenation;

Step 2) converting compound SI-01 to compound 11 by reduction and in situ protection;

Step 3) coupling compound 11 and compound 9 to form compound 12 by asymmetric alkylation;

Step 4) converting compound 12 to compound 8 by selective ozonolysis followed by in situ aldol condensation and dehydration;

Step 5) converting compound 8 to compound 7 by pinacol coupling and in situ lactonization;

Step 6) converting compound 7 to compound 13 by hydration;

Step 7) converting compound 13 to compound 14 by acylation;

Step 8) converting compound 14 to compound 6 by deprotection, oxidation, and reduction;

Step 9) converting compound 6 to compound 18 by acylation, and deprotection; and Step 10) converting compound 18 to nortrilobolide (3) by acylation:

6

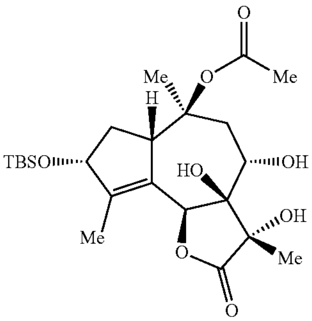

7

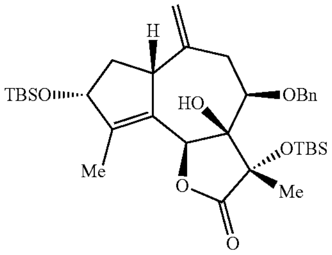

8

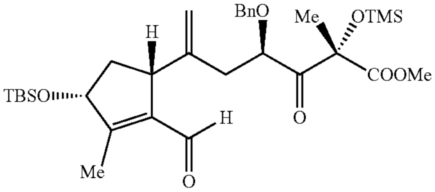

9

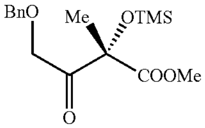

10

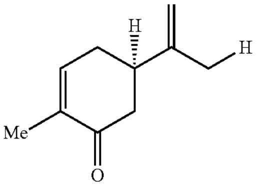

-continued

11

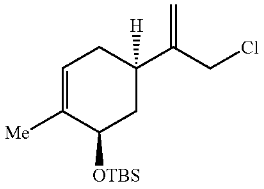

12

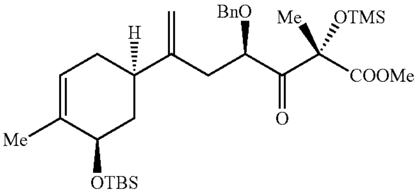

13

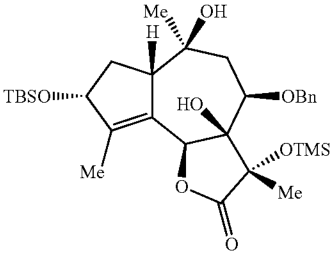

14

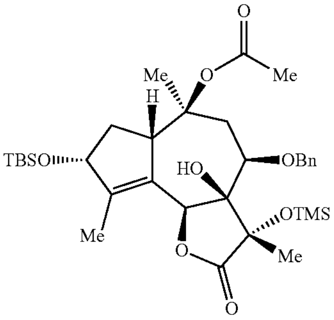

18

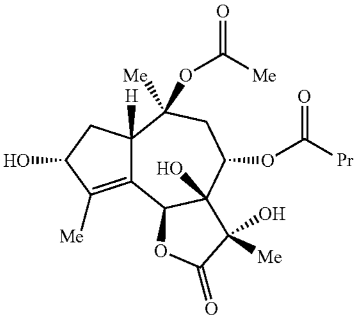

Si-01

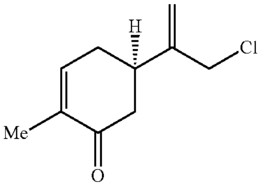

-continued (3)

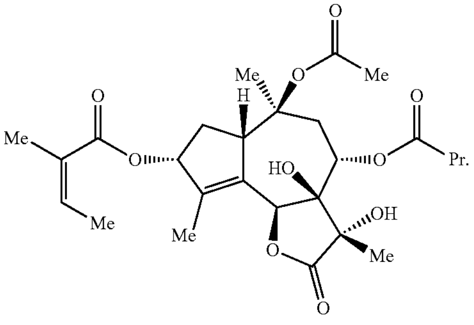

Nortrilobolide

In one embodiment, wherein the compound of Formula I is compound 9 or a pharmaceutically acceptable salt thereof, the method further comprises the steps of:

converting compound SI-02 to compound SI-03 by dihydroxylation; and converting compound SI-03 to compound 9 by oxidation and in situ protection

SI-02

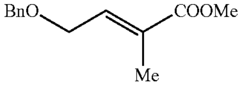

SI-03

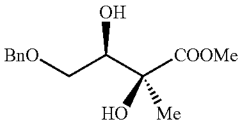

9

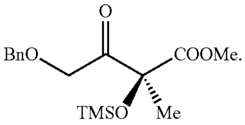

In one embodiment, wherein the compound of Formula I is compound 18 or a pharmaceutically acceptable salt thereof, the method further comprises the step of selective acylation and deprotection of compound 6

6

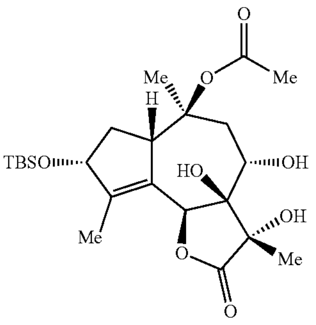

-continued

18

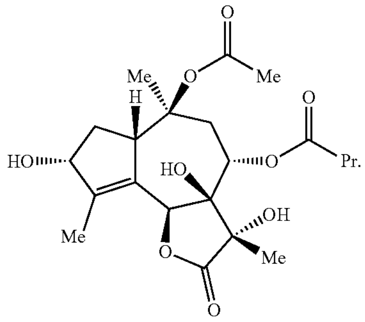

In one embodiment, wherein the compound of Formula I is compound 15 or a pharmaceutically acceptable salt thereof, the method further comprises the step of selective acylation and oxidation of compound 6

6

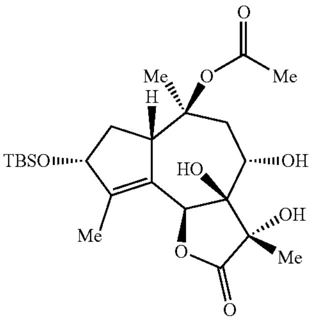

15

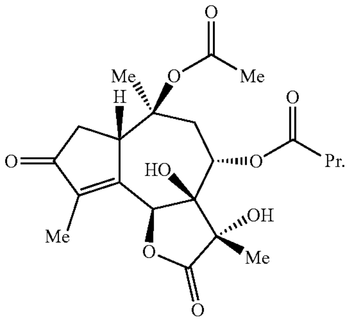

In one embodiment, wherein the compound of Formula I is compound 6 or a pharmaceutically acceptable salt thereof, the method further comprises the step of inverting stereochemistry of compound 14 at C-8

6

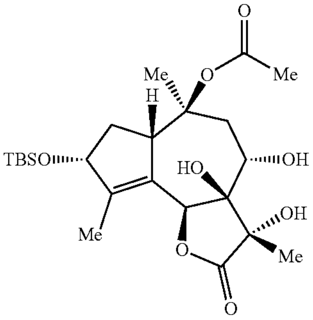

14

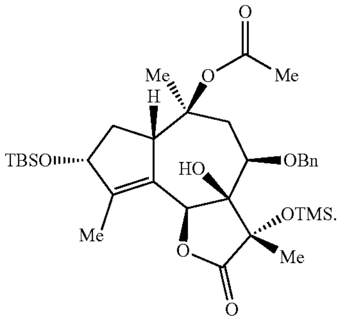

In one embodiment, wherein the compound of Formula I is compound 13 or a pharmaceutically acceptable salt thereof, the method further comprises the step of stereoselective installation of oxygen functionality at C-10 position of compound 7

7

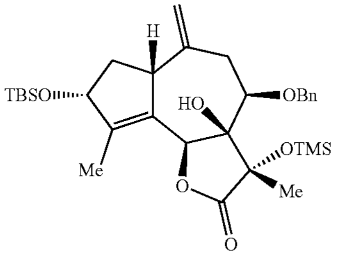

13

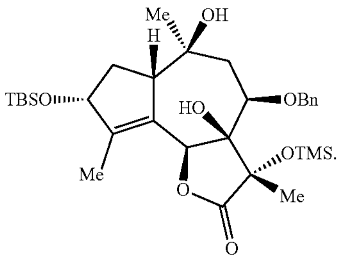

In one embodiment, wherein the compound of Formula I is compound 7 or a pharmaceutically acceptable salt thereof, the method further comprises the step of pinacol coupling and in situ lactonization of compound 8

8

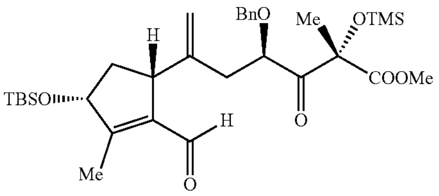

7

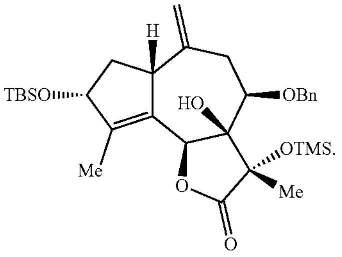

In one embodiment, the compound of Formula I is 8-O-debutanoyl-thapsigargin (22) or a pharmaceutically acceptable salt thereof, comprising the steps of Step C1) converting of (R)-(−)-carvone (10) to compound SI-01 by allylic halogenation;

Step C2) converting compound SI-01 to compound 11 by reduction and in situ protection;

Step C3) coupling compound 11 and compound 9 to form compound 12 by asymmetrical alkylation;

Step C4) converting compound 12 to compound 8 by selective ozonolysis and in situ aldol condensation and dehydration;

Step C5) converting compound 8 to compound 7 by pinacol coupling and in situ lactonization;

Step C6) converting compound 7 to compound 13 by hydration;

Step C7) converting compound 13 to compound 14 by acylation;

Step C8) converting compound 14 compound 19 by oxidation;

Step C9) converting compound 19 to compound 20 by oxidation;

Step C10) converting compound 20 to compound 21 by reduction and acylation, and

Step C11) converting compound 21 to 8-O-debutanoyl-thapsigargin (22) by deprotection, oxidation and reduction,

14

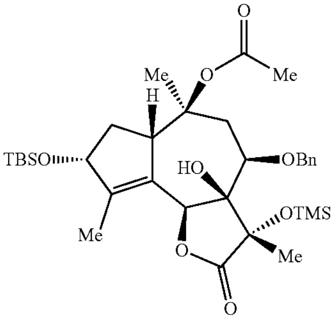

19

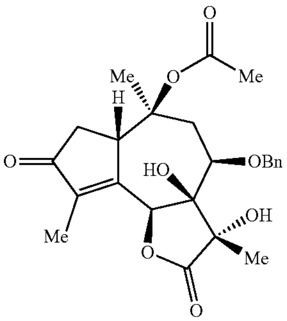

20

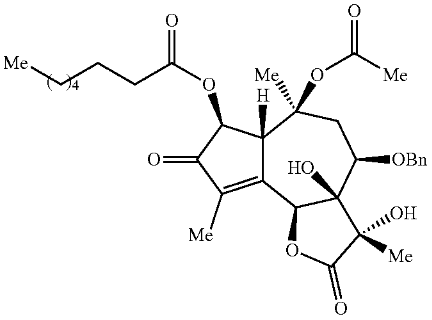

-continued

21

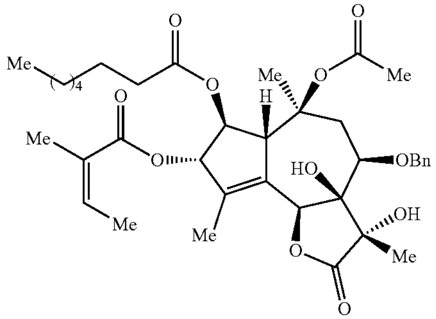

(22)

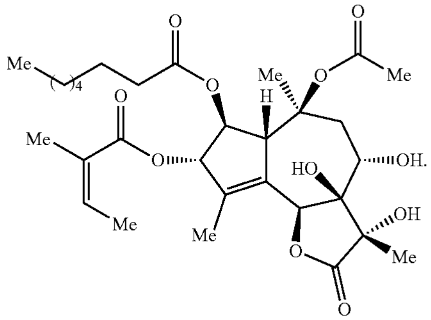

8-O-debutanoyl-thapsigargin

In one embodiment, the method further includes attaching a polypeptide or other linkers for the attachment of antibodies. In one embodiment, the product is a compound of Formula III

III

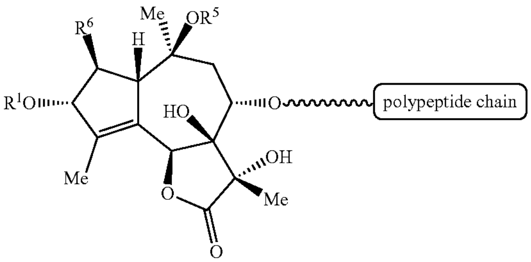

wherein $R^1$ and $R^5$ are independently acyl groups;

$R^6$ is H or an acyloxyl group.

In one embodiment, the compound of Formula III is a compound of Formula III a. In one embodiment, the compound of Formula III a is MIPSAGARGIN® (5)

(5)

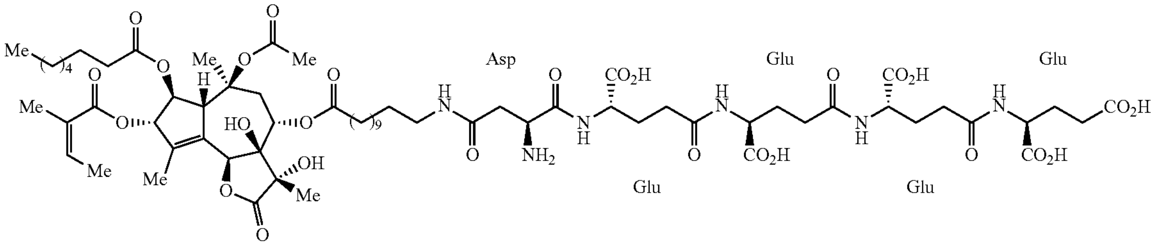

MIPSAGARGIN

In one embodiment, the compound of Formula I is DC-22-042 or a pharmaceutically acceptable salt thereof, comprising the steps of Step 1) converting compound 11 to DC-18-037 by asymmetric allylic coupling with lithium enolate of ketone 9 in the presence of lithium chloride and a chiral catalyst derived from $Pd_2(dba)_3.CHCl_3$ and (R)-BINAP followed by selective ozonolysis and an in situ intramolecular aldol condensation; and Step 2) converting compound DC-18-037 to DC-22-042 by reaction with $[V_2Cl_3(TH\ F)_6]_2[Zn_2Cl_6]$

11

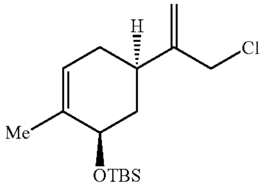

DC-18-037

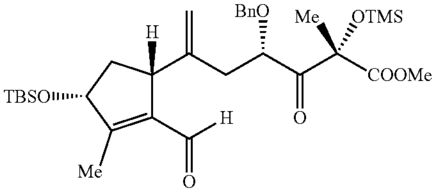

9

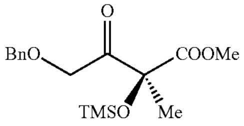

DC-22-042

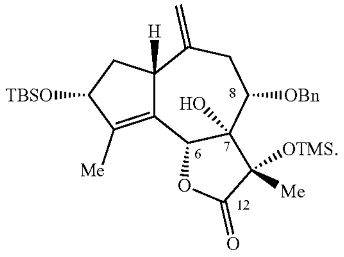

In one aspect, the invention provides a compound of Formula I or a compound used in synthesis thereof, comprising compound 6, 7, 8, 9, 12, 13, 14, 15, 16, 19, 20, 21, or DC-22-042

6

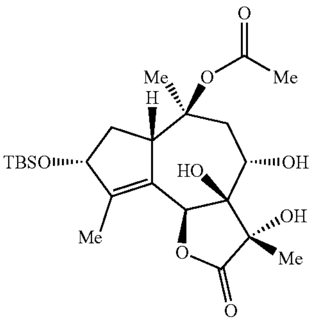

-continued

7

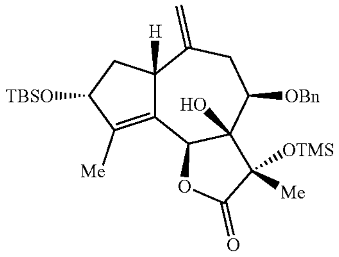

8

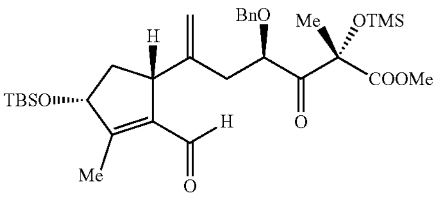

9

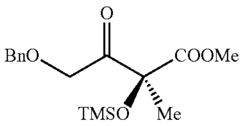

12

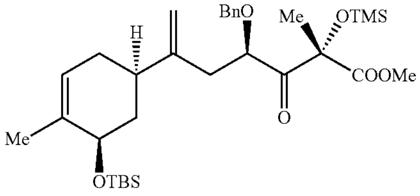

13

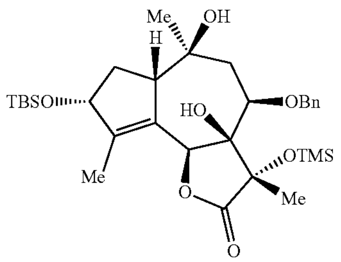

14

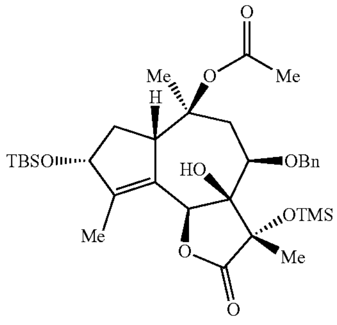

-continued

15

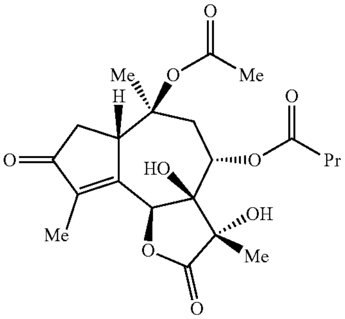

16

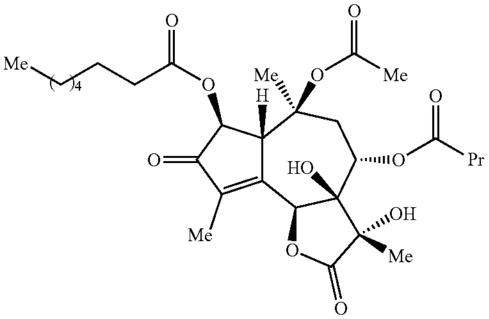

19

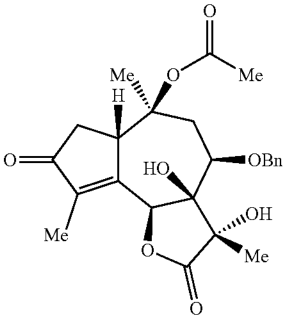

20

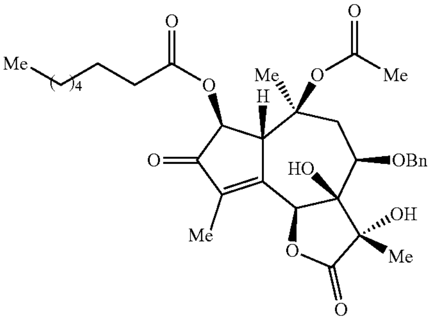

21

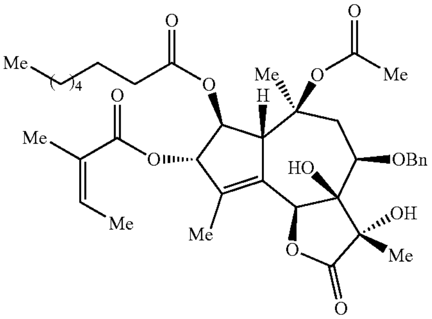

-continued

DC-22-042

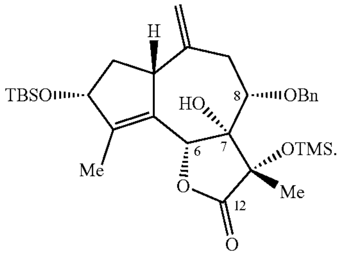

In one aspect, the invention provides a method for synthesizing compound 12, comprising palladium-catalyzed coupling of compound 11 and compound 9

11

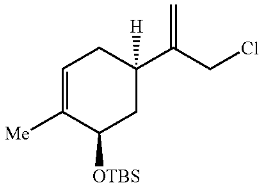

9

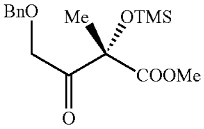

12

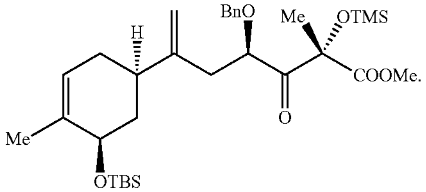

In an aspect, the invention provides a method for synthesis of thapsigargin (1)

(1)

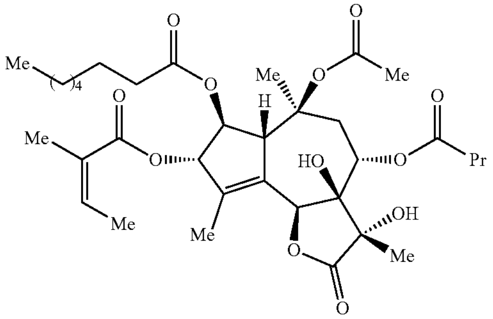

Thapsigargin or a pharmaceutically acceptable salt thereof, comprising the steps of:

Step 1) converting of (R)-(−)-carvone (10) to compound SI-01 by chlorination;

Step 2) converting compound SI-01 to compound 11 by reduction and in situ protection;

Step 3) coupling compound 11 and compound 9 to form compound 12 by asymmetrical alkylation;
Step 4) converting compound 12 to compound 8 by selective ozonolysis and in situ aldol condensation;
Step 5) converting compound 8 to compound 7 by pinacol coupling;
Step 6) converting compound 7 to compound 13 by hydration;
Step 7) converting compound 13 to compound 14 by acylation;
Step 8) converting compound 14 to compound 6 by deprotection, oxidation, and reduction;
Step 9) converting compound 6 to compound 15 by acylation and oxidation;
Step 10) converting compound 15 to compound 16 by oxidation;
Step 11) converting compound 16 to compound SI-04 by reduction; and
Step 12) converting compound SI-04 to thapsigargin (1) by acylation Si-01

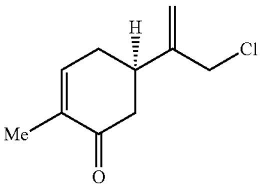

6

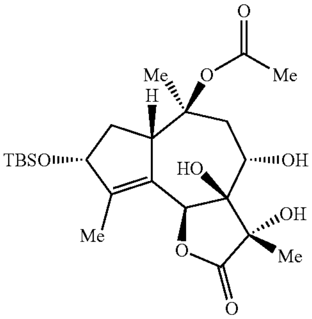

7

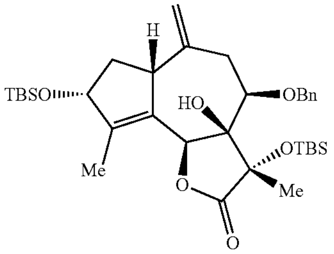

8

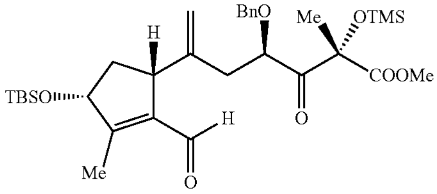

9

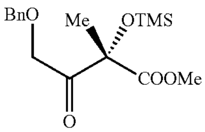

-continued

10

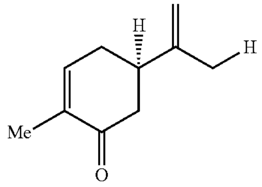

11

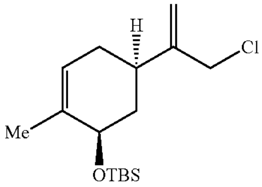

12

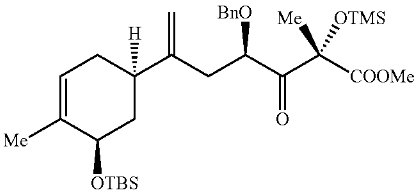

13

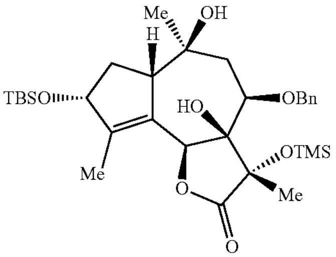

14

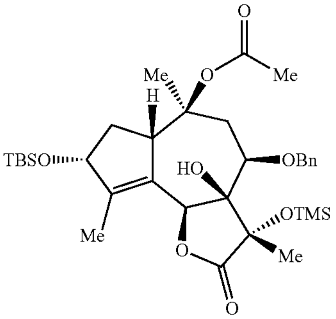

15

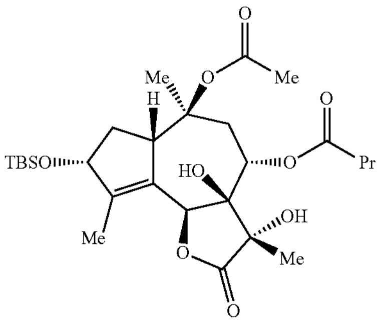

-continued

16

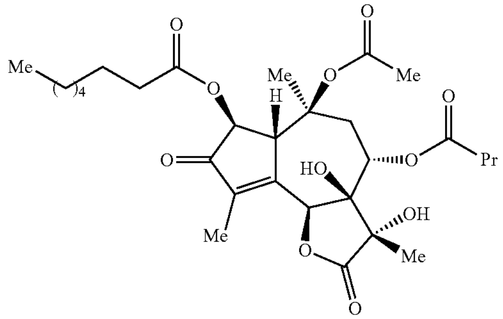

Si-04

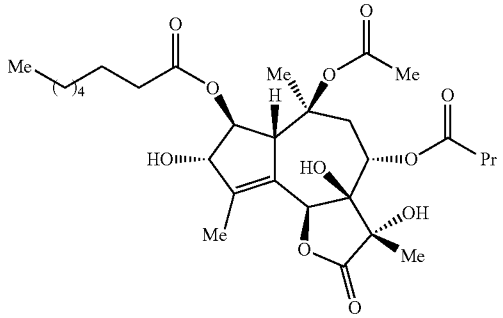

(1)

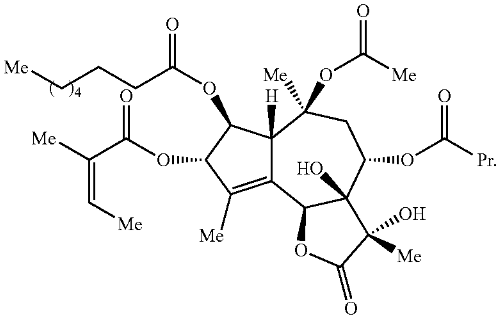

Thapsigargin

In an aspect, the invention provides a method for synthesizing nortrilobolide (3), comprising the following steps:

Step 1) converting (R)-(−)-carvone (10) to compound SI-01 by chlorination;

Step 2) converting compound SI-01 to compound 11 by reduction and in situ protection;

Step 3) coupling compound 11 and compound 9 to form compound 12 by asymmetrical alkylation;

Step 4) converting compound 12 to compound 8 by selective ozonolysis and in situ aldol condensation;

Step 5) converting compound 8 to compound 7 by pinacol coupling;

Step 6) converting compound 7 to compound 13 by hydration;

Step 7) converting compound 13 to compound 14 by acylation;

Step 8) converting compound 14 to compound 6 by deprotection, oxidation, and reduction;

Step 9) converting compound 6 to compound 18 by acylation, and deprotection; and Step 10) converting compound 18 to nortrilobolide (3) by acylation, wherein the compounds have the following structural formulae:

6

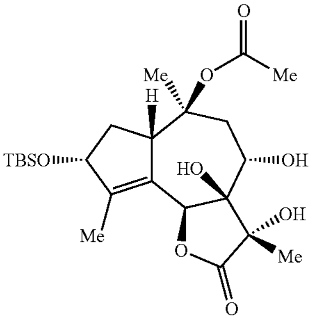

7

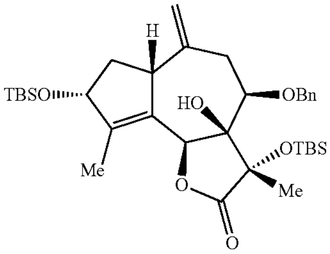

8

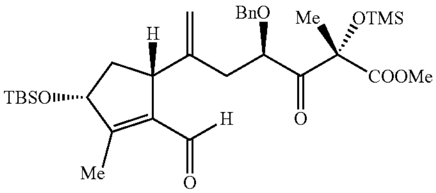

9

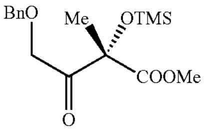

10

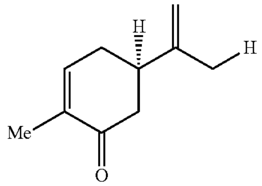

11

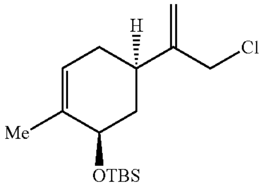

12

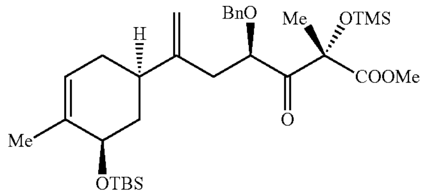

-continued

13

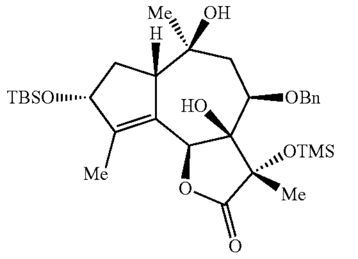

14

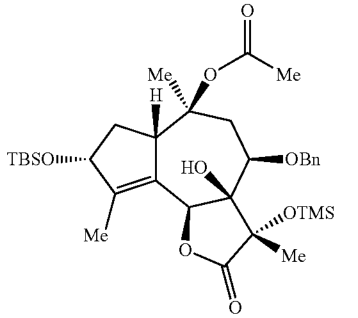

18

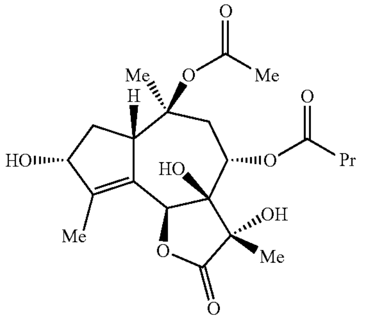

Si-01

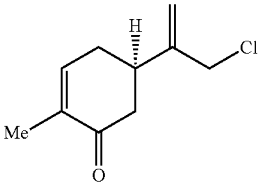

(3)

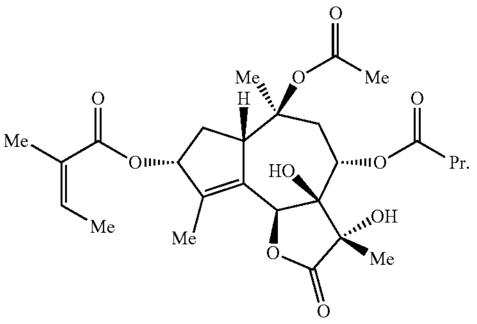

Nortrilobolide

In some embodiments, compound 10 is reacted with t-BuOCl to yield SI-01. In some embodiments, the, Compound SI-01 is reacted with a reducing agent, a protecting group, and a base to yield compound 11. In some embodiments, in step 2, the reducing agent is Dibal-H. In some embodiments, in step 2, the protecting group is TBSCl or TBOTf. In some embodiments, in step 2, the base is imidazole, or triethylamine. In some embodiments, in step 3, Compound 11 and compound 9 are reacted with a strong base, LiCl, a chiral ligand, and a palladium catalyst to yield compound 12. In some embodiments, the strong base is LiHMDS, or LDA. In some embodiments, the chiral ligand is (S)-BINAP. In some embodiments, the palladium catalyst is $Pd_2(dba)_3.CHCl_3$. In some embodiments, in step 4, Compound 12 is reacted with $O_3$, and a reducing agent, and then piperidinium acetate to yield compound 8. In some embodiments, the reducing agent is $Ph_3P$ or $Me_2S$. In some embodiments, in step 5, Compound 8 is reacted with $VCl_3(THF)_3$, Zn, and HMPA to yield compound 7. In some embodiments, in step 6, Compound 7 is reacted with a cobalt or manganese catalyst, $PhSiH_3$, and $O_2$ to yield compound 13. In some embodiments, the cobalt or manganese catalyst is $Co(acac)_2$ or $Mn(dmp)_3$. In some embodiments, the in step 7, Compound 13 is reacted with $Ac_2O$, and DMAP to yield compound 14. In some embodiments, in step 8, Compound 14 is reacted with a palladium catalyst and $H_2$, and then an oxidant and a reducing agent to yield compound 6. In some embodiments, the palladium catalyst is $Pd(OH)_2/C$. In some embodiments, the oxidant is IBX, DMP, or PCC. In some embodiments, the reducing agent is $NaBH_4$. In some embodiments, in step 9, Compound 6 is reacted with $(PrCO)_2O$ and DMAP, and then Jones reagent to yield compound 15. In some embodiments, in step 10, compound 15 is reacted with $Mn(OAc)_3$ and octanoic acid to yield compound 16. In some embodiments, in step 11, compound 16 is reacted with $Zn(BH_4)_2$ to yield compound SI-04. In some embodiments, for the acylation reaction of step 12, compound SI-04 is reacted with 17 and a base to yield thapsigargin (1). In some embodiments, the base is $NaHCO_3$. In some embodiments, in step 1, (10) is reacted with t-BuOCl to yield SI-01. In some embodiments, in step 2, SI-01 is reacted with a reducing agent, a reactant comprising a protecting group, and a base to yield compound 11. In some embodiments, the reducing agent is Dibal-H. In some embodiments, the reactant comprising a protecting group is TBSCl or TBOTf. In some embodiments, the base is imidazole or triethylamine. In some embodiments, in step 3, compound 11 and compound 9 are reacted with a strong base, LiCl, chiral ligand, and a palladium catalyst to yield compound 12. In some embodiments, the strong base is LiHMDS or LDA. In some embodiments, the chiral ligand is (S)-BINAP. In some embodiments, the palladium catalyst is $Pd_2(dba)_3(CHCl_3)$. In some embodiments, in step 4, compound 12 is reacted with $O_3$, and a reducing agent, and then piperidinium acetate to yield compound 8. In some embodiments, the reducing agent is $Ph_3P$ or $Me_2S$. In some embodiments, in step 5, compound 8 is reacted with $VCl_3(THF)_3$, Zn and HMPA to yield compound 7. In some embodiments, in step 6, compound 7 is reacted with a cobalt or manganese catalyst, $PhSiH_3$, and $O_2$, to yield compound 13. In some embodiments, cobalt or manganese catalyst is $Co(acac)_2$ or $Mn(dmp)_3$. In some embodiments, in step 7, compound 13 is reacted with $Ac_2O$ and DMAP to yield compound 14. In some embodiments, in step 8, compound 14 is reacted with a palladium catalyst, and $H_2$, and then an oxidant, and a reducing agent to yield compound 6. In some embodiments, the palladium catalyst is $Pd(OH)_2/C$. In some embodiments, the oxidant is IBX, DMP, PCC. In some embodiments, the reducing agent is $NaBH_4$. In some embodiments, in step 9, compound 6 is acylated by reaction with $(PrCO)_2O$ and DMAP; and deprotected in AcOH/THF/$H_2O$ to yield compound 18. In some embodiments, in step 10, compound 18 is acylated by reaction with compound 17 and a base to yield nortrilobolide (3).

In an aspect, the invention provides compound 9

9

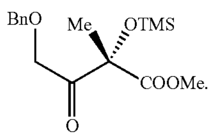

In an aspect, the invention provides compound 6

6

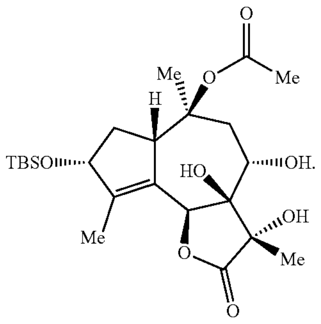

In an aspect, the invention provides compound 13

13

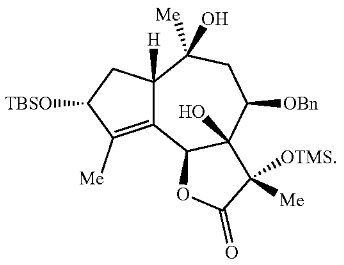

In an aspect, the invention provides compound 7

7

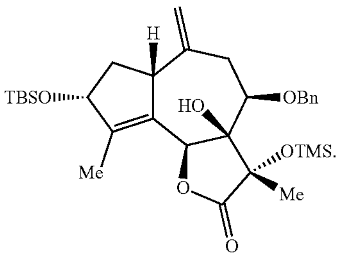

In an aspect, the invention provides compound 8

8

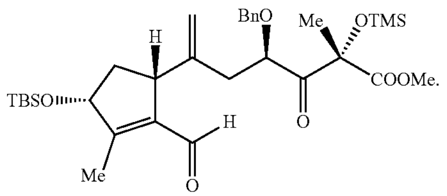

In an aspect, the invention provides compound 12

12

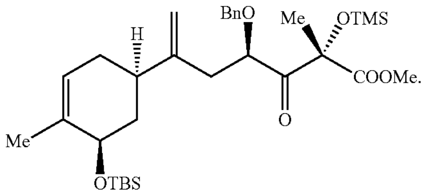

In an aspect, the invention provides a method for synthesizing compound 9, comprising the following steps converting compound SI-02 to compound SI-03 by dihydroxylation, and converting compound SI-03 to compound 9 by oxidation and in situ protection

SI-02

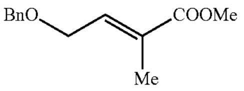

SI-03

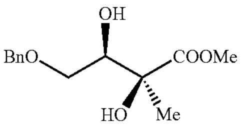

9

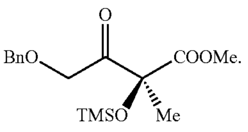

In an aspect, the invention provides a method for synthesizing compound 18, comprising selective acylation of an alcohol at C-8 position of compound 6 and deprotection at C-3 position

6

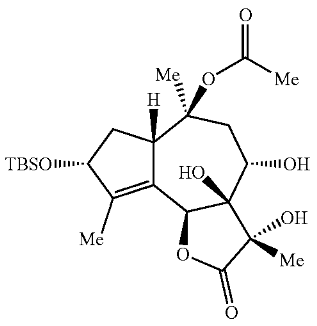

-continued

18

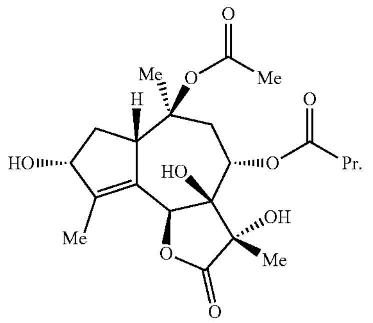

In an aspect, the invention provides a method for synthesizing compound 15, comprising selective acylation of an alcohol at C-8 position of compound 6 and direct oxidation of TBS ether at C-3 position

6

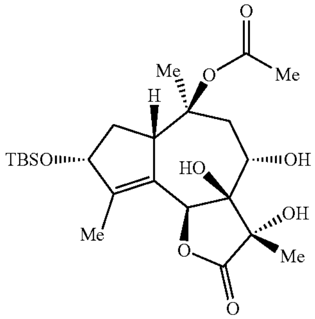

15

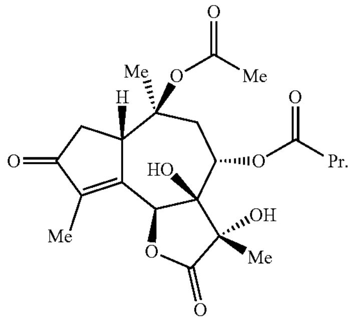

In an aspect, the invention provides a method for synthesizing compound 6, comprising inversion of stereochemistry of compound 14 at C-8 position

6

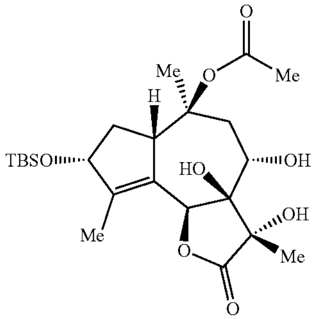

-continued

14

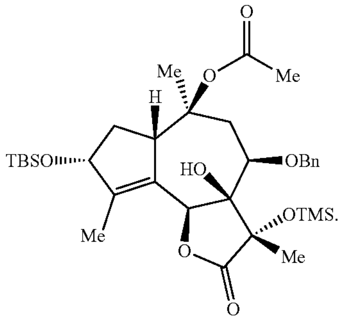

In an aspect, the invention provides a method for synthesizing compound 13, comprising stereoselective installation of oxygen functionality at C-10 position of compound 7

7

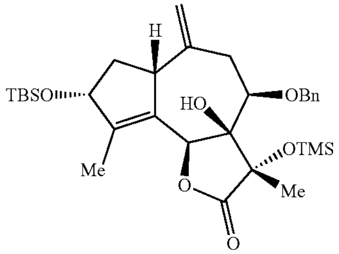

13

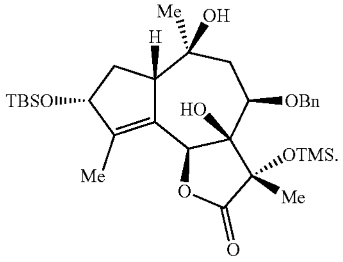

In an aspect, the invention provides a method for synthesizing compound 7, comprising pinacol coupling of compound 8

7

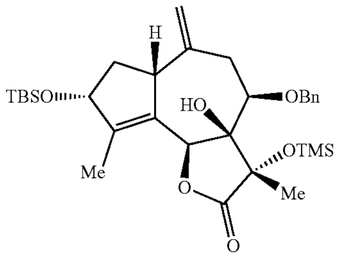

-continued

8

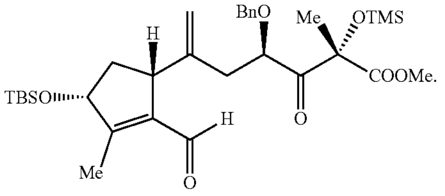

In some embodiments, the pinacol coupling uses a reducing reagent. In some embodiments, the reducing reagent is $[V_2Cl_3(THF)_6]2[Zn_2Cl_6]$. In some embodiments, the $[V_2Cl_3(THF)_6]_2[Zn_2Cl_6]$ is generated in situ from $VCl_3(THF)_3$ and Zn or is prepared beforehand.

In an aspect, the invention provides a method for synthesizing compound 8, comprising ozonolysis of compound 12 followed by aldol condensation

12

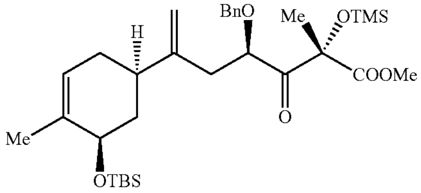

8

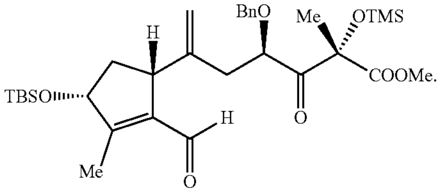

In an aspect, the invention provides a method for synthesizing compound 12, comprising palladium-catalyzed coupling of compound 11 and compound 9

11

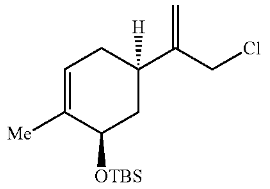

9

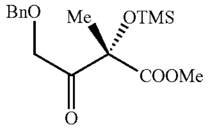

12

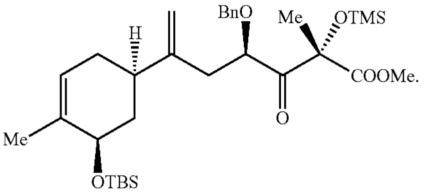

In an aspect, the invention provides a method for synthesizing compound 11, comprising chlorination of (R)-(−)-carvone, followed by reduction and protection (10)

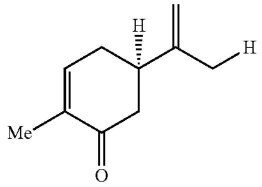

(R)-(-)carvone

11

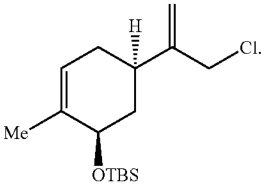

In another aspect, the invention provides a method for synthesizing 8-O-debutanoyl-thapsigargin (22), comprising steps C1 to C7 are the same as steps 1 to 7 of the above synthesis of thapsigargin wherein (R)-(−)-carvone (10) is converted to compound 14;

step C8) converting compound 14 compound 19 by oxidation;

step C9) converting compound 19 to compound 20 by oxidation;

step C10) converting compound 20 to compound 21 by reduction and acylation, and step C11) converting compound 21 to 8-O-debutanoyl-thapsigargin (22) by deprotection, oxidation and reduction, wherein the compounds have the following structural formulae:

14

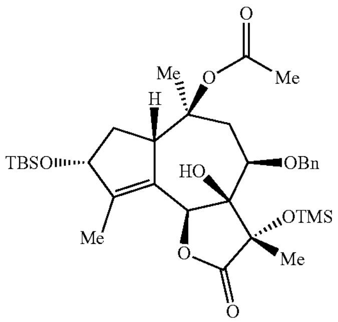

19

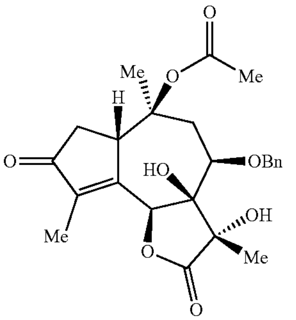

-continued

20

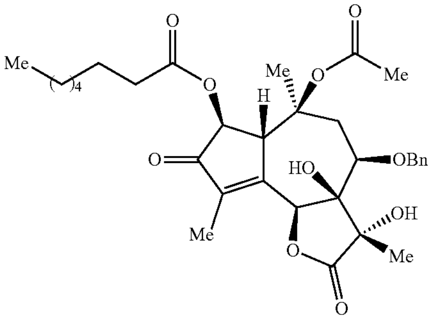

21

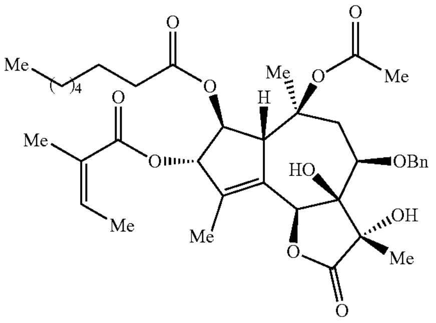

(22)

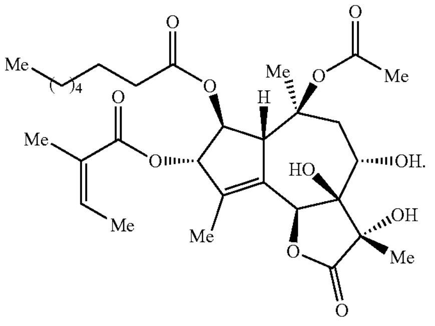

8-O-debutanoyl-thapsigargin

In some embodiments, compound 14 is oxidized by reaction with $CrO_3$ to yield compound 19

14

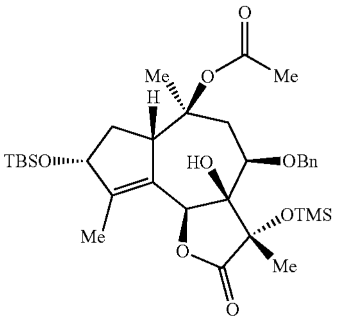

-continued

19

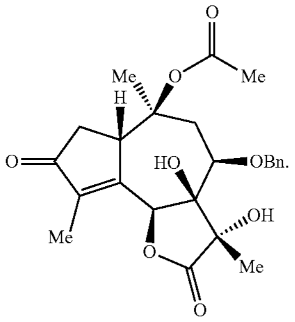

In some embodiments, compound 19 undergoes radical oxidation by reaction with $Mn(OAc)_3$ and octanoic acid to form compound 20

19

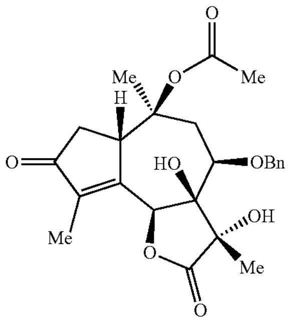

20

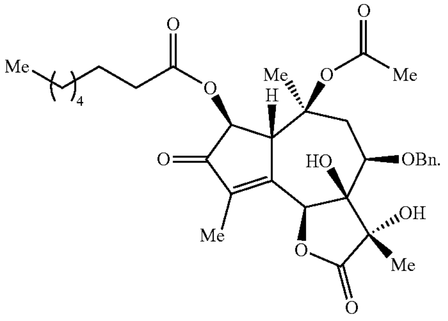

In some embodiments, compound 20 is reacted with $Zn(BH_4)_2$ and acylated by reaction with 17 and a base to form compound 21

20

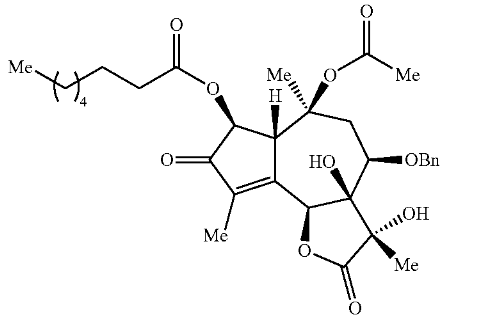

21

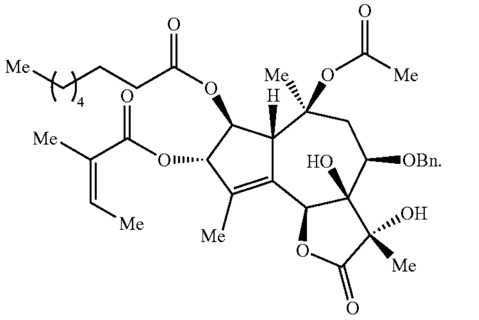

In some embodiments, the base is $NaHCO_3$. In some embodiments, compound 21 is deprotected by reaction with $Pd(OH)_2/C$, $H_2$ followed by oxidation by reaction with IBX, and followed by reduction to form 8-O-debutanoyl-thapsigargin (22)

21

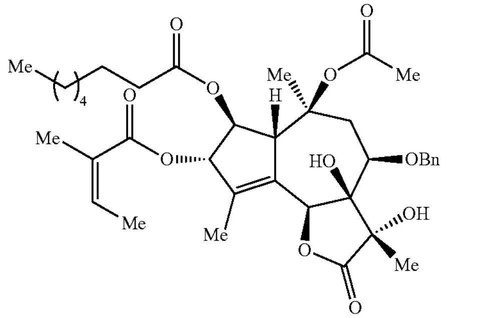

-continued (22)

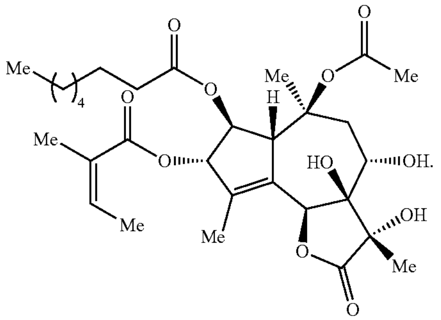

8-O-debutanolyl-thapsigargin

In some embodiments, the reduction occurs by reaction with $NaBH_4$.

In another aspect, the invention provides a method for synthesizing compounds of Formula III, comprising preparing compound (1) according to the above synthesis of thapsigargin, and attaching a polypeptide to form a compound of Formula III

III

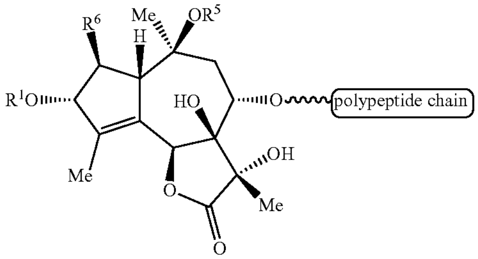

wherein $R^1$ and $R^5$ are independently acyl groups; and $R^6$ is H or an acyloxyl group.

In some embodiments, the compound of Formula III is MIPSAGARGIN® (5).

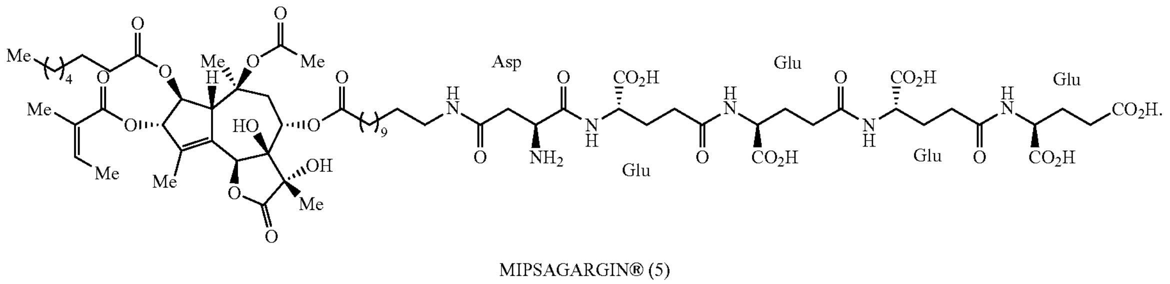

MIPSAGARGIN® (5)

In another aspect, the invention provides a compound having the structural formulae of compound 12, 8, 7, 13, 14, 19, 6, 20, 15, 16, 21, or a pharmaceutical salt thereof.

In another aspect, the invention provides a method for synthesizing a compound of Formula I or a pharmaceutically acceptable salt thereof, wherein Formula I has the following structural formula:

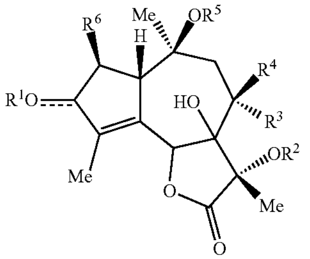

I wherein $R^1$ is H, an acyl or aliphatic group, or may not be present;

$R^2$ is H or a hydroxyl protecting group;

$R^3$ is H or an acyloxy or alkoxy group;

$R^4$ is H or acyloxy group or OP wherein P is a hydroxyl protecting group;

$R^5$ is H or an acyl or aliphatic group;

$R^6$ is H or an acyloxy or alkoxy group:

carbon moieties within acyl, acyloxy, alkyl and alkoxy groups are aliphatic or aryl and may be substituted or unsubstituted, and a dotted line represents a bond that may or may not be present.

BRIEF DESCRIPTION OF THE DRAWINGS

For a better understanding of the present invention and to illustrate more clearly how it may be carried into effect, reference will now be made by way of example to the accompanying drawings, which illustrate aspects and features according to preferred embodiments of the present invention, and in which.

Step 1. t-BuOCl (1.2 equiv), pentane, RT.

Step 2. Dibal-H (1M in hexanes, 1.1 equiv), DCM, −78° C.; TBSCl (3.0 equiv), imidazole (3.0 equiv), rt, 88% over two steps.

Step 3. 11 (1.1 equiv), LiHMDS (1.1 equiv), LiCl (2.4 equiv), (S)-BINAP (0.04 equiv), $Pd_2(dba)_3.(CHCl_3)$ (0.01 equiv), THF, 0° C., 93%, dr=8:1.

Step 4. $O_3$, EtOAc, −78° C.; then $Ph_3P$ (3.0 equiv), RT; then piperidinium acetate (0.2 equiv), 78° C., 40-55%.

Step 5. $VCl_3(THF)_3$ (4.6 equiv), Zn (2.8 equiv), HMPA (12.0 equiv), DCM, RT, 60%.

Step 6. $Co(acac)_2$ (0.3 equiv), $PhSiH_3$ (2.5 equiv), $O_2$, EtOH, 0° C., 79%, dr≥19:1.

Step 7. $Ac_2O$ (10.0 equiv), DMAP (1.1 equiv), PhMe, 110° C., 85-96%.

Step 8. $Pd(OH)_2/C$, $H_2$, EtOAc, RT; then IBX (5.0 equiv), RT, DMSO; $NaBH_4$ (3.0 equiv), DMSO/MeOH, −10° C., 94% over two steps, dr≥19:1.

Step 9. $(PrCO)_2O$ (2.0 equiv), DMAP (0.2 equiv), DCM, RT; then Jones reagent (4.2 equiv), acetone, 87%.

Step 10. $Mn(OAc)_3$ (6.0 equiv), Benzene/Octanoic acid, 80° C., 61%.

Step 11. $Zn(BH_4)_2$ (0.5 M in $Et_2O$, 24.0 equiv), $Et_2O$, −20° C.

Step 12. 17 (10.0 equiv), $NaHCO_3$ (20.0 equiv), PhMe, 90° C., 64% over 2 steps.

Figure 4:
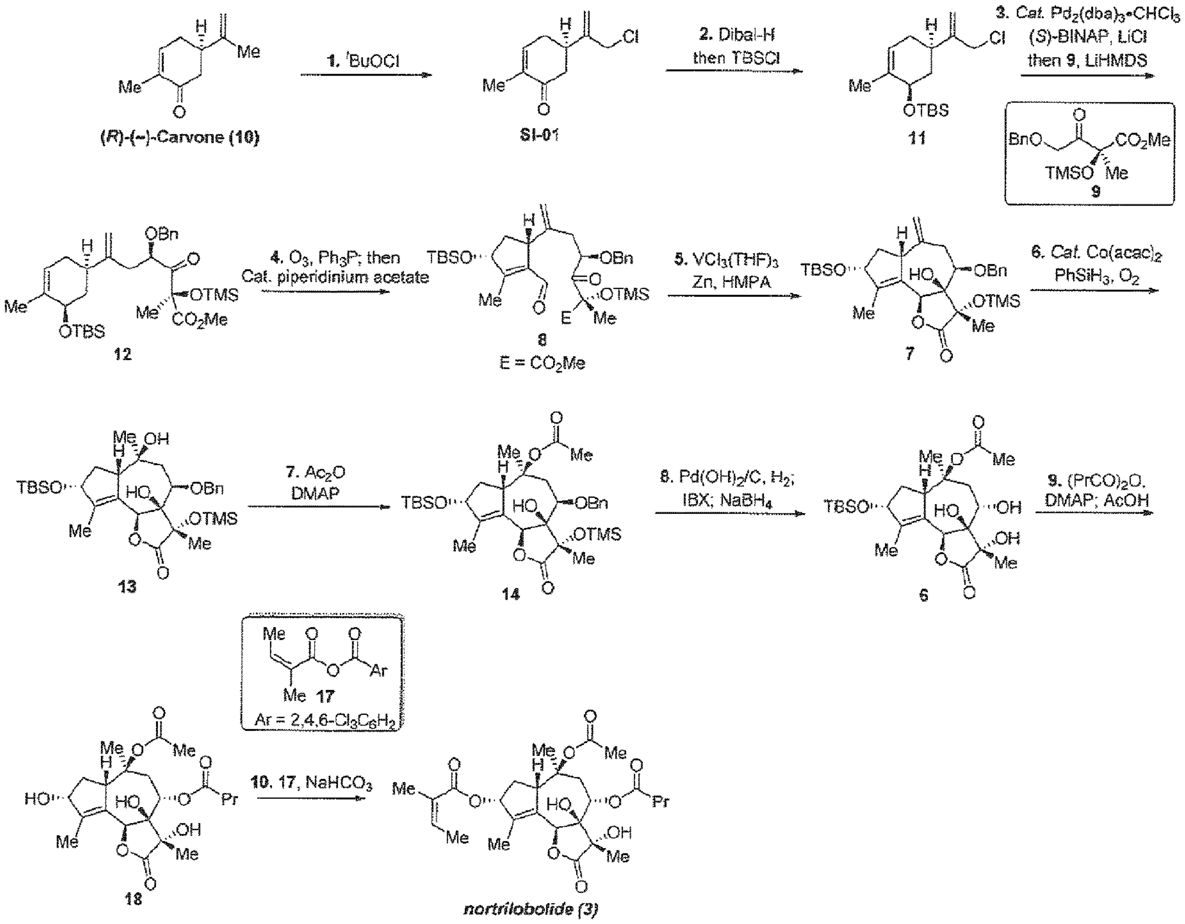

FIG. 4 illustrates a 10-step synthesis of nortrilobolide (3).

Figure 3:
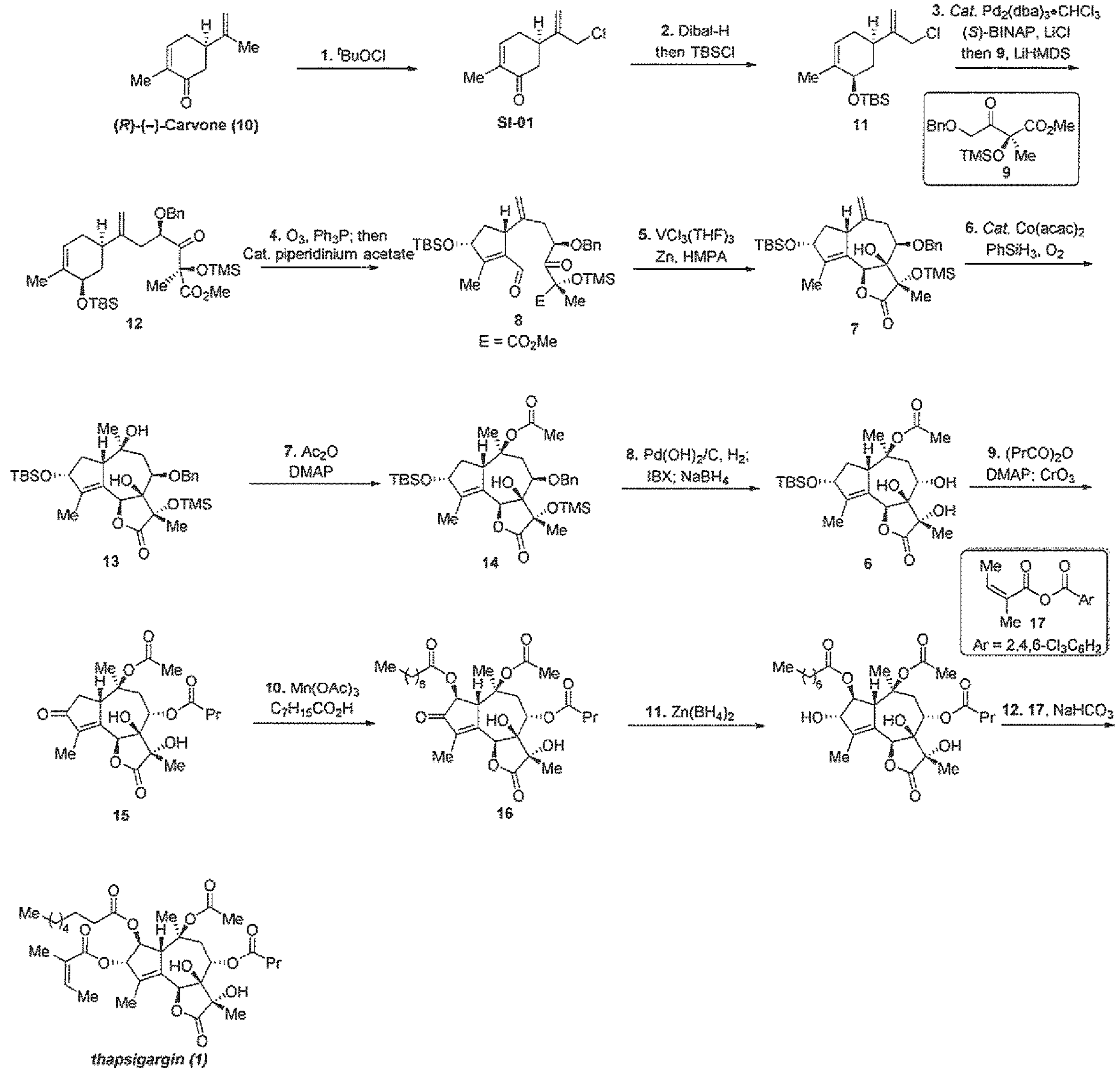
FIG. 3 illustrates a 12-step synthesis of thapsigargin (1), reactants and conditions as follows.
Figure 5:
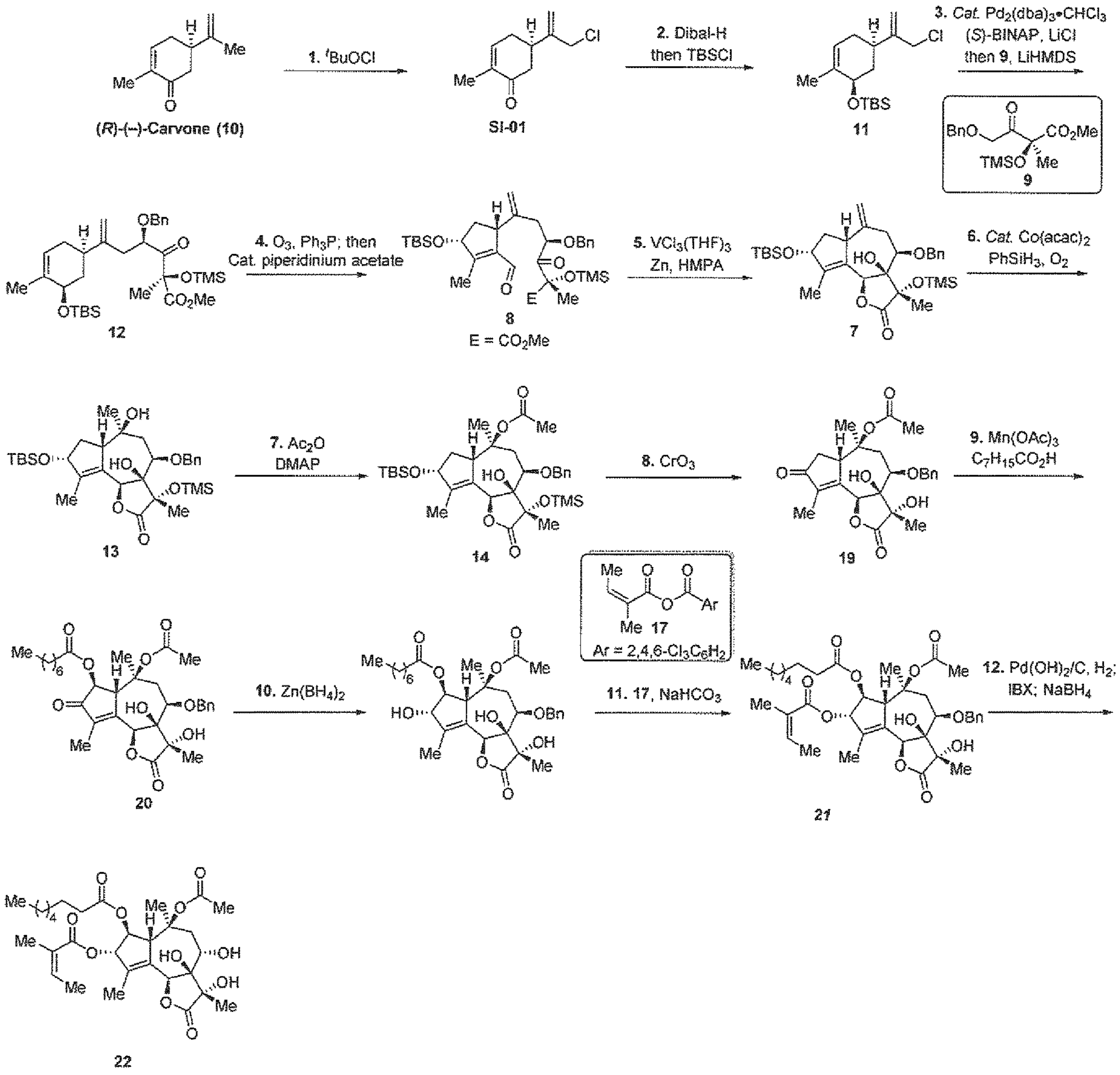

FIG. 5 illustrates a 12-step prophetic synthesis of 8-O-debutanoyl-thapsigargin (22) which shares its first seven steps with the synthesis of thapsigargin (1) of FIG. 3.

DETAILED DESCRIPTION OF EMBODIMENTS

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein "aliphatic" includes alkyl, alkenyl and alkynyl. An aliphatic group may be substituted or unsubstituted. It may be straight chain, branched chain or cyclic. The term "alkyl" refers to a linear or branched or cyclic hydrocarbon unit with certain number of carbon atoms, which may be fully saturated or partially saturated and may be substituted by other alkyl groups or heteroatoms.

As used herein "aryl" includes aromatic carbocycles and aromatic heterocycles and may be substituted or unsubstituted.

As used herein "unsubstituted" refers to any open valence of an atom being occupied by hydrogen.

As used herein "substituted" refers to the structure having one or more substituents.

As used herein "heteroatom" means a non-carbon, non-hydrogen atom, and may be used to denote atoms that have a lone pair of electrons available to form dative or coordinate bonds (e.g., N, O, P).

As used herein "synthetic intermediate" refers to any chemical substance produced in a given step of a multi-step synthetic pathway of a reactant to a final product.

As used herein the term "TBSO" refers to a tertbutyldimethylsilyloxy moiety.

As used herein the term "alkoxy" or "alkoxy group" refers to an —O—R moiety, where R is an aliphatic or aryl moiety that may be substituted or unsubstituted.

As used herein the term "acyloxy" or "acyloxy group" refers to a —O—C(═O)—R moiety, where R is an aliphatic or aryl moiety that may be substituted or unsubstituted.

As used herein the term "acyl" or "acyl group" refers to a —C(═O)—R moiety, where R is an aliphatic or aryl moiety that may be substituted or unsubstituted.

As used herein the term "ester" refers to a —C(═O)—O—R or a —C(═O)—S—R moiety, where R is an aliphatic or aryl moiety that may be substituted or unsubstituted.

As used herein the term "amide" refers to a —C(═O)—$NR^1R^2$ moiety where $R^1$ and $R^2$ are independently hydrogen atoms or aliphatic or aryl moieties.

As used herein the term "leaving group" refers to a moiety of a reactant that is displaced by another moiety during a reaction. Common leaving groups include, for example, chloride, bromide, iodide, mesylate, tosylate, and triflate.

As used herein, the term "substituted" means having one or more substituent moieties whose presence either facilitates or improves the desired reaction or does not impede the desired reaction. A "substituent" is an atom or group of bonded atoms that can be considered to have replaced one or more hydrogen atoms attached to a parent molecular entity; and, whose presence either facilitates or improves desired reactions and/or functions of the invention or does not impede desired reactions and/or functions of the invention. Examples of substituents include alkyl, alkenyl, alkynyl, aryl, polycyclic aryl, benzyl, polycyclic benzyl, fused aromatic rings, aryl-halide, heteroaryl, cycloalkyl (non-aromatic ring), $Si(alkyl)_3$, $Si(alkoxy)_3$, halo, alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfonamide, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents defined above, such as alkyl, alkenyl, alkynyl, aryl, aryl-halide, and heteroaryl cycloalkyl (non-aromatic ring).

As used herein, "aliphatic" refers to hydrocarbon moieties that are linear, branched or cyclic, may be alkyl, alkenyl or alkynyl, and may be substituted or unsubstituted. "Alkenyl" means a hydrocarbon moiety that is linear, branched or cyclic and contains at least one carbon to carbon double bond. "Alkynyl" means a hydrocarbon moiety that is linear, branched or cyclic and contains at least one carbon to carbon triple bond.

As used herein, "alkyl" or "alkylene" refers to a linear, branched or cyclic, saturated hydrocarbon, which consists solely of single-bonded carbon and hydrogen atoms, which can be unsubstituted or is optionally substituted with one or more substituents, for example, a methyl or ethyl group. Examples of saturated straight or branched chain alkyl groups include, but are not limited to, methyl, ethyl, 1-propyl, 2-propyl, 1-butyl, 2-butyl, 2-methyl-1-propyl, 2 methyl 2-propyl, 1 pentyl, 2-pentyl, 3-pentyl, 2-methyl-1-butyl, 3-methyl-1-butyl, 2-methyl-3-butyl, 2,2 dimethyl 1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups.

The term "cycloalkyl" as used herein refers to a non-aromatic, saturated or partially saturated, monocyclic, bicyclic or tricyclic hydrocarbon ring system containing at least 3 carbon atoms. Examples of $C_3$-$C_n$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, "alkenyl" or "alkenylene" means a hydrocarbon moiety that is linear, branched or cyclic and comprises at least one carbon to carbon double bond which can be unsubstituted or optionally substituted with one or more substituents. "Alkynyl" or "alkynylene" means a hydrocarbon moiety that is linear, branched or cyclic and comprises at least one carbon to carbon triple bond which can be unsubstituted or optionally substituted with one or more substituents.

As used herein, "aryl" and/or "aromatic ring" refers to hydrocarbons derived from benzene or a benzene derivative that are unsaturated aromatic carbocyclic groups from 6 to 100 carbon atoms, or from which may or may not be a fused ring system, in some embodiments 6 to 50, in other embodiments 6 to 25, and in still other embodiments 6 to 15. The aryls may have single or multiple rings. The term "aryl" and/or "aromatic ring" as used herein also includes substituted aryls and/or aromatic rings. Examples include, but are not limited to, phenyl, naphthyl, xylene, phenylethane, substituted phenyl, substituted naphthyl, substituted xylene, substituted 4-ethylphenyl and the like.

As used herein, the term "unsubstituted" refers to any open valence of an atom being occupied by hydrogen. Also, if an occupant of an open valence position on an atom is not specified then it is hydrogen.

As used herein the term "hydroxyl protecting groups" includes many moieties that are used to block an oxygen moiety from reaction until the protecting group is cleaved and the oxygen is once again available for reaction (Wuts, P. G. M. and Greene, T. W. (2007) "Protective Groups in Organic Synthesis" John Wiley & Sons).

As used herein "SERCA" refers to sarco/endoplasmic reticulum $Ca^{2+}$-ATPases.

As used herein "TBS" refers to tert-butyldimethylsilyl.

As used herein "Bn" refers to benzyl.

As used herein "TMS" refers to trimethylsilyl.

As used herein "$^t$BuOCl" refers to tert-butyl hypochlorite.

As used herein "Dibal-H" refers to diisobutylaluminum hydride.

As used herein "LiHMDS" refers to lithium hexamethyldisilazide.

As used herein "LiCl" refers to lithium chloride.

As used herein "$Pd_2(dba)_3.CHCl_3$" refers to tris (dibenzylideneacetone) dipalladium (0)-chloroform adduct.

As used herein "(S)-BINAP" refers to (S)-(−)-2,2'-Bis (diphenylphosphino)-1,1'-binaphthyl.

As used herein "HMPA" refers to hexamethylphosphoramide.

As used herein "DMAP" refers to dimethylaminopyridine.

As used herein "IBX" refers to 2-lodoxybenzoic acid.

As used herein "DCM" refers to dichloromethane.

As used herein "$(DHQD)_2PHAL$" refers to hydroquinidine 1,4-phthalazinediyl diether.

As used herein "TMSCl" refers to trimethylsilyl chloride.

As used herein "THF" refers to tetrahydrofuran.

As used herein "PhMe" refers to toluene.

As used herein "$Pd(OH)_2/C$" refers to palladium hydroxide on carbon.

As used herein "NaEDTA" refers to disodium ethylenediaminetetraacetate.

As used herein "AcOH" refers to acetic acid.

EMBODIMENTS

Figure 1:
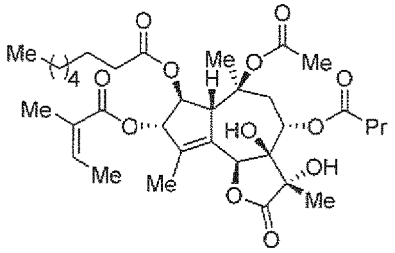
FIG. 1 illustrates molecular structures of thapsigargin (1), nortrilobolide (3), and MIPSAGARGIN® (5).
Figure 1:
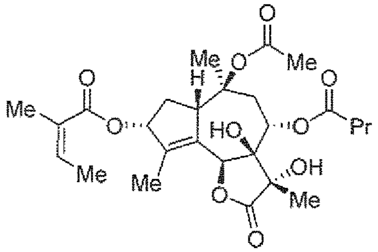
Figure 1:
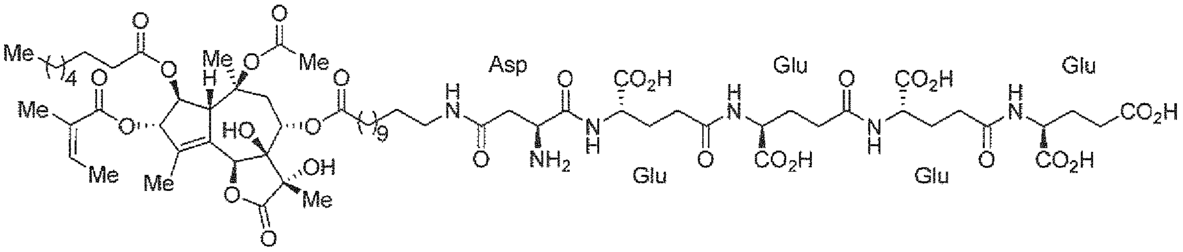

Thapsigargin (1) and nortrilobolide (3) (see FIG. 1) are complex, densely oxygenated sesquiterpene lactones, which have, until now, provided a significant and ongoing challenge for the development of a commercially feasible synthetic route to these agents. For instance, they were first synthesized in 2007 by Ley and coworkers, who reported that thapsigargin (1) and nortrilobolide (3) could be prepared from (S)-(+)-carvone in 42 and 36 steps with an overall yield of 0.6% and 1.32%, respectively (Ball, M., Ley, S. V., et al., Org. Lett. 2007, 9: 663-666). In addition, Baran recently completed the synthesis of these agents in 11 and 10 steps, but with overall yields of 0.16% and 0.46%, respectively (Chu, H. et al. *ACS Cent. Sci.* 2017, 3: 47-51). Hence, despite these achievements, the large number of steps and low overall yield has not enabled synthesis on a practical scale to be affordable.

Hence, synthetic routes to thapsigargin (1) and nortrilobolide (3) and analogs thereof were complicated by long, multi-step synthetic routes that were not suitable on a preparative scale. At this time, synthetic routes have been discovered that address the need for efficient and practical chemical synthetic pathways to prepare, for example, thapsigargin (1), nortrilobolide (3), 8-O-debutanoyl-thapsigargin (22), and analogs and synthetic intermediates thereof. Such synthetic pathways are needed since thapsigargins are structurally complex and medicinally relevant family of compounds. They function as a selective and irreversible subnanomolar inhibitor of sarco/endoplasmic reticulum $Ca^{2+}$ ATPases (SERCAs). Also, MIPSAGARGIN® (5), which is a prodrug of thapsigargin (1), is currently in phase II clinical trials for the treatment of liver, brain, prostate, and kidney cancer. Accordingly, development of commercially feasible synthetic routes, as provided herein, are a valuable contribution enabling preparation of thapsigargins for clinical applications.

A concise, efficient, and scalable synthesis has been developed for preparation of a highly oxidized guaianolide skeleton, which has been shown to enable total synthesis of thapsigargin (1), nortrilobolide (3), thapsigargicin, thapsitranstagin, 2-acetoxytrilobolide, thapsivillosin A, thapsivillosin B, thapsivillosin C, thapsivillosin D, thapsivillosin E, thapsivillosin H, thapsivillosin G, thapsivillosin H, thapsivillosin I, thapsivillosin J, thapsivillosin L, thapsivillosin F, and trilobolide, from commercially available starting reagent (R)-(−)-carvone (10). In one embodiment, the synthetic route is 12 steps. A 12-step synthetic route for 8-O-debutanoyl-thapsigargin (22) has also been developed. A compound of Formula IB, a diastereomer of Formula I, has also been prepared, namely DC-22-042. These synthetic routes are summarized in the figures and details are provided in the Working Examples.

In one embodiment, a compound of Formula I has been prepared by subjecting a reactant to a series of chemical reactions that produce synthetic intermediates. In one embodiment, the synthetic route includes an alkylation to produce compound 12. In one embodiment, the synthetic route includes a chlorination to produce compound SI-01. In one embodiment, the synthetic route includes a reduction and in situ protection of SI-01 to produce compound 11. In one embodiment, the synthetic route includes coupling 11 and 9 to form compound 12 by asymmetric alkylation. In one embodiment, the synthetic route includes selective ozonolysis and in situ aldol condensation of 12 to produce compound 8. In one embodiment, the synthetic route includes pinacol coupling of 8 to produce compound 7. In one embodiment, the synthetic route includes a hydration of 7 to produce compound 13. In one embodiment, the synthetic route includes acylation of 13 to produce compound 14. In one embodiment, the synthetic route includes deprotection, oxidation, and reduction of 14 to produce compound 6. In one embodiment, the synthetic route includes acylation and oxidation of 6 to produce compound 15. In one embodiment, the synthetic route includes oxidation of 15 to produce compound 16. In one embodiment, the synthetic route includes reduction of 16 to produce compound SI-04. In one embodiment, the synthetic route includes acylation of SI-04 to produce thapsigargin (1). In one embodiment, the synthetic route includes acylating, and deprotecting compound 6 to form compound 18. In one embodiment, the synthetic route includes acylating compound 18 to form nortrilobolide 3. In one embodiment, the synthetic route includes carvone (10) is converted to compound 14. In one embodiment, the synthetic route includes oxidation of 14 to form compound 19. In one embodiment, the synthetic route includes oxidation of 19 to form compound 20. In one embodiment, the synthetic route includes reduction and acylation of compound 20 to form compound 21. In one embodiment, the synthetic route includes deprotecting, oxidation and reduction of compound 21 to form 8-O-debutanoyl-thapsigargin (22). In one embodiment, the synthetic route includes converting compound 11 by asymmetric allylic coupling with lithium enolate of ketone 9 in the presence of lithium chloride and a chiral catalyst derived from $Pd_2(dba)_3.CHCl_3$ and (R)-BINAP followed by selective ozonolysis and an in situ intramolecular aldol condensation to form compound DC-18-037. In one embodiment, the synthetic route includes converting compound DC-18-037 by reaction with $[V_2Cl_3(THF)_6]2[Zn_2Cl_6]$ to form compound DC-22-042.

The synthetic strategy described herein emulates nature's carbon-carbon bond formation sequence, which facilitates construction of a highly functionalized sesquiterpene lactone skeleton in only 5-steps. This skeleton was accomplished via an enantioselective ketone alkylation and a diastereoselective pinacol cyclization. Further, this synthetic strategy provides access to structurally-related molecules, and provides a practical synthetic route to nortrilobolide (3), which is a bioactive agent as it is a potent inhibitor of SERCA.

Figure 2:
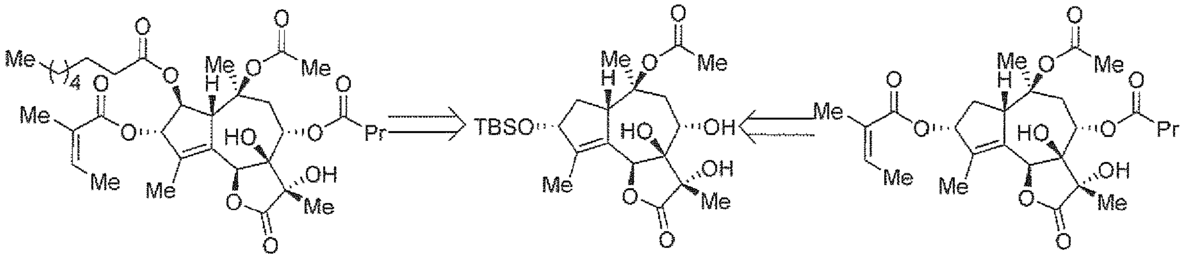
FIG. 2 illustrates a retrosynthetic analysis.
Figure 2:
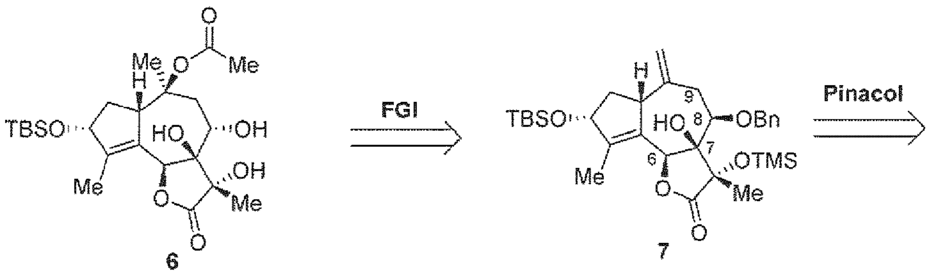
Figure 2:
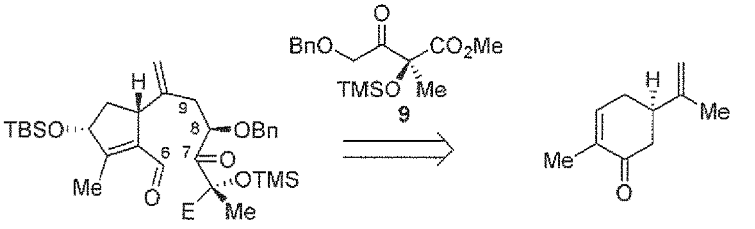

Total synthesis of thapsigargin (1) has a number of inherent challenges. Including asymmetrical construction of a hexa-oxygenated 5-7-5 tricyclic guaianolide skeleton functionalized with eight contiguous stereogenic centers. Additional challenges include installation of four different ester groups, a trans-vicinal tertiary diol, and an internal tetrasubstituted olefin. Efficient synthesis of thapsigargin (1) required a strategic introduction of oxygen substituents to minimize redox chemistry, protecting group, and functional group manipulations. To this end, a divergent strategy has been developed, wherein a common synthetic intermediate 6 provided access both to thapsigargin (1) and to all other members of the thapsigargin family, including nortrilobolide (3) (see FIG. 2). In accord with sesquiterpene lactone biosynthesis pathway (Andersen, T. B. et al. *Plant Physiol.* 2017, DOI:10.1104/pp. 16.00055), it was recognized that retrosynthetic disconnection of carbon-carbon bonds at C-6/C-7 and C-8/C-9 achieved these goals and thereby minimized functional group transformations.

As shown in the figures, an assembly from (R)-(−)-carvone (10) and methylerythritol derivative 9 combined 10 and 5 carbon fragments, which is consistent with nature's building blocks and carbon-carbon bond formations in assembly of sesquiterpene lactones. Hence, this abiotic approach utilized a transition metal-catalyzed enantioselective alkylation reaction. To forge the 15-carbon framework in compound 8, which is necessary for a metal-mediated aldehyde/ketone pinacol coupling reaction to construct guaianolide skeleton 7 en route to a common synthetic intermediate 6 (see FIG. 2). This novel and biosynthetically-inspired process has incorporated the necessary stereochemistry and functionality for the syntheses of thapsigargin (1) and nortrilobolide (3) in a concise manner.

The synthetic pathway provided rapid and scalable access to guaianolide 7, which served as a key synthetic intermediate for thapsigargin (1), nortrilobolide (3), and the preparation of structurally-related molecules that permitted structure activity studies.

Synthetic Steps to Form Thapsigargin (1)

Synthesis of thapsigargin (1) commenced with conversion of commercially available monoterpene, (R)-(−)-carvone (10), into an appropriate electrophile for the alkylative coupling with compound 9 (FIG. 3). This conversion involved a selective allylic chlorination of terminal olefin with tert-butyl hypochlorite (t-BuOCl) at room temperature (Nakamura, E., et al. *J. Am. Chem. Soc.* 1987, 109: 8056-8066).

This chlorination step was followed by stereoselective reduction of ketone using diisobutylaluminum hydride (DIBAL-H) and in situ silylation of the resulting alcohol using tertbutyldimethylsilyl chloride (TBSCl), which provided allylic chloride 11 in 88% yield over two steps (Ceschi M. A. et al. *J. Braz. Chem. Soc.* 2006, 2: 321-327). Asymmetrical alkylative coupling of 11 with the lithium enolate of ketone 9, which was generated with lithium hexamethyldisilazide (LiHMDS), was achieved in the presence of lithium chloride (LiCl) and the chiral catalyst derived from $Pd_2(dba)_3.CHCl_3$ with (S)-BINAP to furnish the coupled product 12 in 93% yield and with 8:1 diastereoselectivity.

A ring-contraction of the cyclohexene in 12 was then accomplished via selective oxidative cleavage of more electron rich olefin with ozone followed by an in situ intramolecular aldol condensation catalyzed by piperidinium acetate, to afford after dehydration the cyclopentene derivative 8 in moderate overall yield. This one-pot transformation permitted installation of the internal tetrasubstituted double bond present in the natural product and simultaneously sets the stage for the key sequential pinacol cyclization/lactonization cascade reaction.

Dimeric vanadium complex, $[V_2Cl_3(THF)_6]2[Zn_2Cl_6]$, which was prepared in situ in the presence of hexamethylphosphoramide (HMPA) (A. W. Konradi, et al., *J. Am. Chem. Soc.* 1994, 116: 1316-1323 and A. S. Raw, et al., *J. Org. Chem.* 1991, 56: 830-833), facilitated conversion of 8 to sesquiterpene lactone 7 in 60% overall yield and with ≥19:1 diastereoselectivity on a multigram reaction scale. Interestingly, the C-8 benzyloxy ether group is critical for the stereochemical outcome of the pinacol coupling reaction, since the epimer provides the opposite stereochemistry at C6/C7 Hence, this 5-step sequence provides a scalable and stereochemically versatile approach to the highly oxidized guaianolide skeleton 7. This skeleton is a synthetic tool that enables construction of a wide array of structural and stereochemically diverse analogs.

Installation of oxygenated functionality at the C-10 position was then accomplished by a selective cobalt-catalyzed Mukaiyama hydration of the less sterically hindered olefin and the acetylation of the resulting tertiary alcohol.

Treatment of compound 7 with cobalt(II) acetylacetonate $[Co(acac)_2]$ catalyst and excess phenylsilane ($PhSiH_3$) under oxygen atmosphere provided 13 in 79% yield and with ≥19:1 diastereoselectivity (Isayama, S.; Mukaiyama, T. *Chem. Lett.* 1989, 18: 1071-1074). Single-crystal X-ray diffraction analysis of 13 confirmed both the relative configuration and structural assignment of this key tricyclic intermediate.

Selective acetylation of the C-10 tertiary alcohol in 13 under elevated temperature afforded the desired tertiary acetate, compound 14, in 85% yield. The stereochemistry at C-8 was then adjusted and the requisite ester introduced. Inversion of the C-8 alcohol using the following sequence, which involved the selective hydrogenation of the benzyl ether with palladium hydroxide $[Pd(OH)_2]$ under a hydrogen atmosphere and the oxidation of the secondary hydroxyl with 2-iodoxybenzoic acid (IBX) followed by sodium borohydride ($NaBH_4$) reduction, generated compound 6 in 94% overall yield and with ≥19:1 diastereoselectivity on a gram reaction scale. In addition, these conditions conveniently cleave the trimethylsilyl (TMS) protecting group. The selective acylation of 6 proceeded cleanly, which permits the in situ Jones oxidation of tert-butyldimethylsilyl (TBS) ether to furnish an α,β-unsaturated cyclopentenone, compound 15, in 87% yield.

In the final stage of this synthesis, conversion of 15 to thapsigargin (1) was achieved by via a slight modification of Christensen's three-step protocol (Crestey, F., et al., *Tetrahedron Lett.* 2015, 56: 5896-5898). Stereoselective introduction of an octanoxyl side chain at C-2 position in enone 16 was accomplished with manganese(III) acetate $[Mn(OAc)_3]$ in benzene and octanic acid as a mixed solvent system. Diastereoselective reduction of the α,β-unsaturated ketone with zinc borohydride $[Zn(BH_4)_2]$ at −20° C. followed by the angeloylation of the sterically hindered C-3 alcohol using mixed anhydride (17) in the presence of sodium bicarbonate ($NaHCO_3$) affords the natural product, thapsigargin (1) in 64% yield.

Synthetic Steps to Form Nortrilobolide (3)

Nortrilobolide (3) differs from thapsigargin (1) at C-2 position. Although there is no oxygenated substituent at C-2 position, it is reported that 3 exhibits equipotent inhibition of Sarco/endoplasmic reticulum $Ca^{2+}$-ATPase to that of 1. Hence, nortrilobolide (3) has recently been utilized as an alternative to thapsigargin (1) for the development of a new generation of anticancer agents. By taking advantage of the rapid and scalable access to synthetic intermediate 6, the total synthesis of nortrilobolide (3) was accomplished as described herein and as illustrated in FIG. 4. The selective acylation of C-8 secondary alcohol in 6 followed by in situ deprotection of a tert-butyldimethylsilyl protecting group under mild acidic conditions gave 18 in 94% yield, which was subjected to the same Yamaguchi acylation described above in the synthesis of thapsigargin (1), to provide the natural product, nortrilobolide (3) in 80% yield.

Synthetic Steps to Form 8-O-Debutanoyl-Thapsigargin (22)

8-O-Debutanoyl-thapsigargin (22) is a key precursor in the manufacturing of MIPSAGARGIN® (5) which is currently in the late-stage clinical trials for the treatment of multiple cancers (Lynch, J. K et al. Methods of Making Cancer Compositions. WO 2014145035 A1, Sep. 18, 2014). Compound 22 was previously synthesized by the selective hydrolysis of thapsigargin (1) (Andersen, A. et al. *J. Label. Compd. Radiopharm.* 1992, 31: 199-206). It is postulated that 8-O-debutanoyl-thapsigargin (22) can be prepared by the synthetic strategy described herein. Specifically, common synthetic intermediate 14 would be converted to enone 19 by Jones oxidation, which allowed installation of octanoyl ester at C-2 position to afford compound 20. The subsequent reduction and acylation would provide compound 21, which would undergo the deprotection/oxidation/reduction sequence to permit to synthesis of 8-O-Debutanoyl-thapsigargin (22).

Overall, the total synthesis of thapsigargin (1) and nortrilobolide (3) was accomplished in 12 and 10 steps (longest linear sequence), respectively (5.8% and 13.3% overall yield) from commercially available (R)-(−)-carvone (10).

Notably, the total syntheses were accomplished in less than one-third of the number of steps required by Ley and coworkers (42 and 36 steps, respectively) and significantly more efficient (30 and 40 times, respectively) than the synthesis reported by Baran and coworkers. In addition, the efficient 5-step synthesis of 7 represents the shortest total synthesis route to the guaianolide skeleton to date, which should allow the rapid preparation of a library of simplified thapsigargin analogs for detailed Structure Activity Relationship Studies. Furthermore, this scalable synthetic route will provide the basis of a manufacturing route to this important agent, particularly given that the key sequence was carried out on gram-scale. Finally, these biosynthetically inspired synthesis of thapsigargin (1), nortrilobolide (3), and 8-O-debutanoyl-thapsigargin (22) will provide a guide for the construction of related polyoxygenated terpenes.

Synthetic Methods for Compounds of Formula I

As described above, methods disclosed herein provide efficient and practical synthetic routes to thapsigargin (1), nortrilobolide (3), and 8-O-debutanoyl-thapsigargin (22) starting from (R)-(−)-carvone (10), which is a commercially available material. In addition, embodiments of the invention provide methods for preparing compounds of Formula I and pharmaceutically acceptable salts thereof, wherein Formula I is:

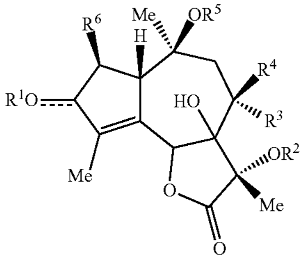

I wherein $R^1$ is H, acyl, aryl, or aliphatic group, or may not be present;

$R^2$ is H, acyl, aliphatic or a hydroxyl protecting group;

$R^3$ and $R^4$ are independently H or acyloxy, alkoxyl, or OP wherein P is a hydroxyl protecting group;

$R^5$ is H or an acyl or aliphatic group;

$R^6$ is H or an acyloxy or alkoxy group:

carbon moieties within acyl, acyloxy, alkyl and alkoxy groups are aliphatic or aryl and may be substituted or unsubstituted, and a dotted line represents a bond that may or may not be present.

Some embodiments provide synthetic routes to make prodrugs. For example, by attaching appropriate polypeptide chains to compounds of Formula II at C-8 position to make compounds of Formula III. Notably, Formula II includes Formulas II a and II b, and Formula III includes Formulas III a and III b as indicated below.

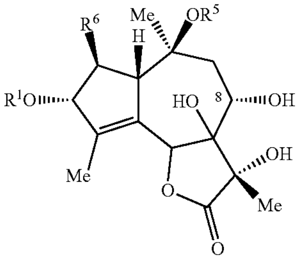

II

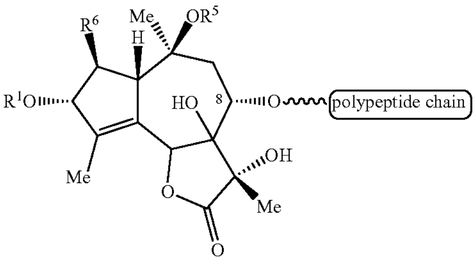

III

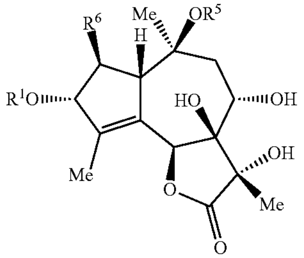

IIa

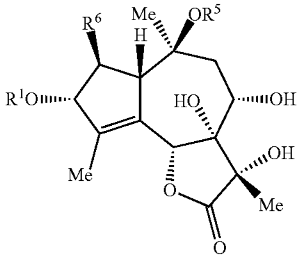

IIb

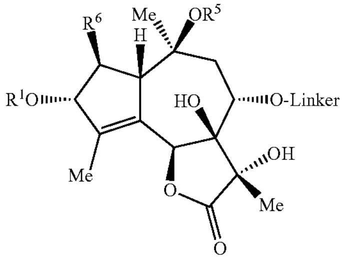

IIIa

-continued

IIIb

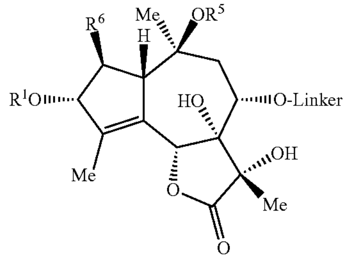

Linker = Acyl, Aryl, or Alkyl
for attachment of polypeptide/antibody wherein $R^1$ and $R^5$ are independently acyl groups;
$R^6$ is H or an acyloxyl group.

An example of a compound of Formula III a includes MIPSAGARGIN® (5).

-continued

VI

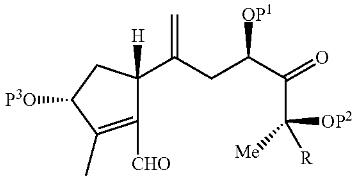

VII

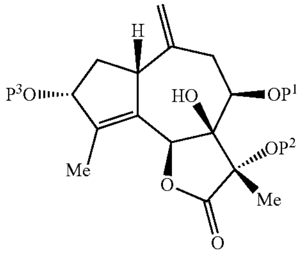

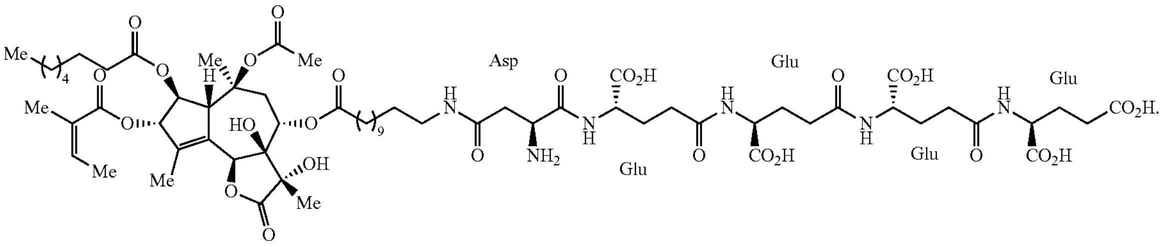

MIPSAGARGIN® (5)

Some embodiments provide a method to prepare compounds of Formula I, starting from a compound of Formula IV.

(IV)

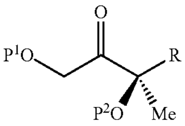

wherein R is an ester or amide (and derivatives thereof); and $P^1$ and $P^2$ are independently hydroxyl protecting groups.

Intermediates of General Formula V, VI, VII, VIII, IX, X, XI, XII and XIII

In certain embodiments, synthetic intermediates in the synthesis of thapsigargin (1) and nortrilobolide (3) were prepared, including compounds of Formulas V, VI, VII, VIII, IX, X, XI, XII and XIII:

V

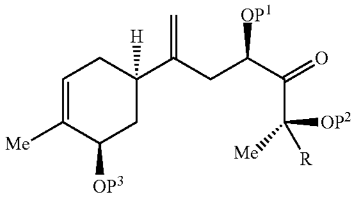

-continued

VIII

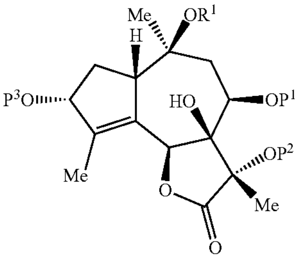

IX

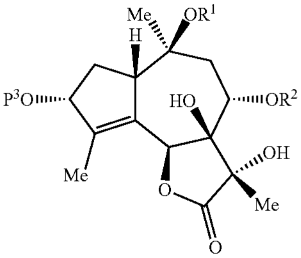

-continued

X

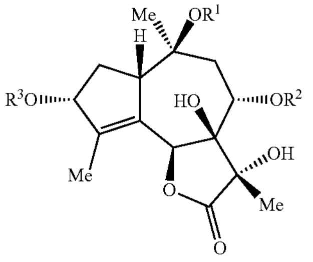

XI

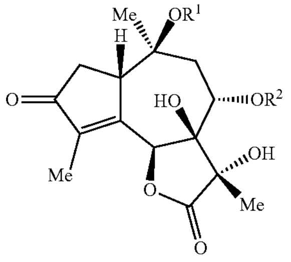

XII

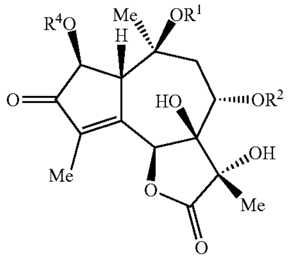

XIII

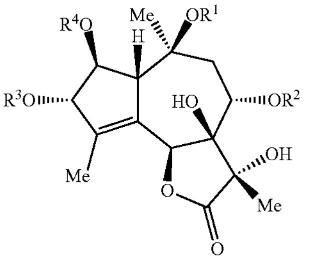

wherein $P^1$, $P^2$, $P^3$ are independently hydroxyl protecting groups;

R is an ester, amide, or derivatives thereof;

$R^1$, $R^2$, $R^3$ and $R^4$ are independently H, acyl groups; and carbon moieties within ($P^1$, $P^2$, $P^3$, $R^1$, $R^2$, $R^3$ and $R^4$) are aliphatic or aryl and may be substituted or unsubstituted.

Synthesis of Compounds of Formula V

In one embodiment, a compound of Formula V is prepared from a coupling reaction of a compound of Formula IV and a compound of Formula XIV:

IV

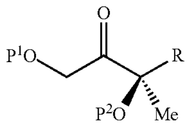

-continued

XIV

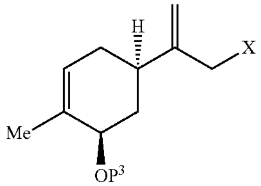

V

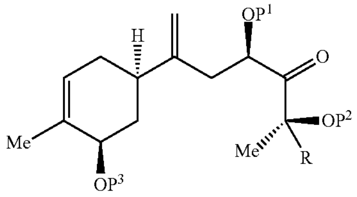

epi-V

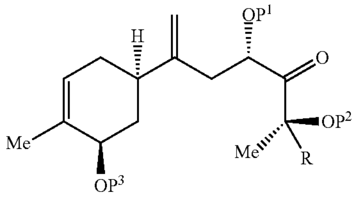

wherein R is either ester, amide and other related derivatives;

$P^1$, $P^2$, $P^3$ are independently hydroxyl protecting groups; and X is a leaving group.

In one embodiment, an enolate of a compound of Formula IV was generated from treatment of conventional strong base, for example LiHMDS or LDA. A coupling reaction was performed under a transition-metal catalyzed condition, e.g., Rh, Ir, Ni with various chiral ligands, for example $Pd_2(dba)_3.CHCl_3$ and (S)-BINAP. A compound of Formula (epi-V) was also prepared by using (R)-BINAP ligand.

Synthesis of Compounds of Formula VI

In one embodiment, a compound of Formula VI was synthesized from a compound of Formula V by a selective ozonolysis of the double bond and in situ aldol condensation catalyzed by piperidinium acetate.

V

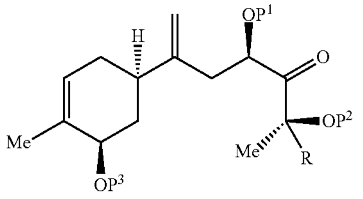

VI

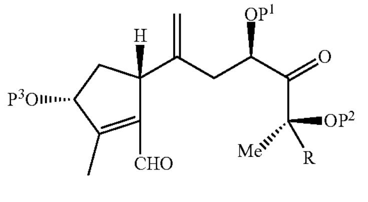

wherein R is either ester, amide and other related derivatives;

$P^1$, $P^2$, $P^3$ are independently hydroxyl protecting groups.

In a further embodiment, oxidative cleavage of a double bond in a compound of Formula VI was not limited to ozonolysis. Other methods were used, for example, $OsO_4$-$NaO_4$, or $RuO_4/NaIO_4$. Aldol condensation was also feasible using conditions such as molecular sieves, basic aluminum oxide, or other reagents.

In another embodiment, a compound of Formula VI was synthesized from a compound of Formula IV and compound XV under the coupling reaction conditions described in the reaction to prepare a compound of Formula V, followed by in situ deprotection of acetal protecting group. A compound of Formula XV was prepared from a compound of Formula XIV under the oxidative cleavage and condensation conditions described in the reaction to prepare a compound of Formula VI.

IV

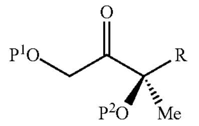

XV

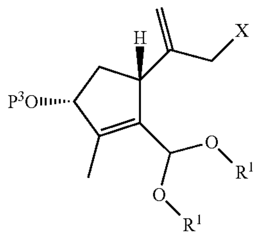

VI

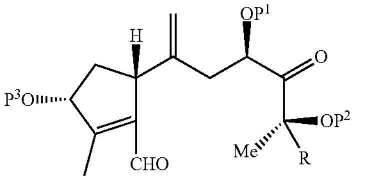

wherein R is either ester, amide and other related derivatives;

$P^1$, $P^2$, $P^3$ are independently hydroxyl protecting groups; and $R^1$ is an aliphatic group;

X is a leaving group.

Synthesis of Compounds of Formula VII

In one embodiment, conversion of a compound of Formula VI to form a compound of Formula VII was achieved by a pinacol coupling, promoted by $[V_2Cl_3(THF)_6]_2[Zn_2Cl_6]$ which was either prepared beforehand or generated in situ from Zn and $VCl_3(THF)_3$ (or other vanadium (II) complexes, for example, $VCl_2(TMEDA)_2$ or $VCl_2(DMPE)_2$). HPMA or DMF additive was used for this transformation. Other one-electron reducing agents may also be applied to this transformation, for example $SmI_2$. Critically, a pinacol coupling reaction was directed by the C-8 oxygen group to provide flexible stereochemical outcomes shown in a compound of Formula epi-VI and a compound of Formula epi-VII.

VI

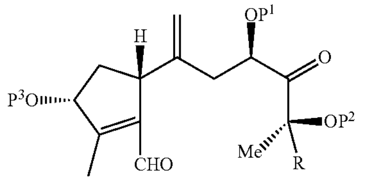

VII

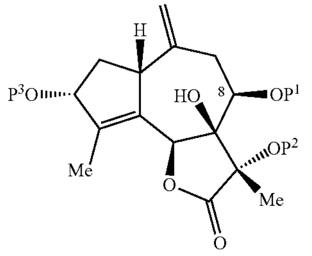

epi-VI

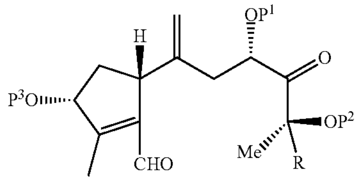

epi-VII

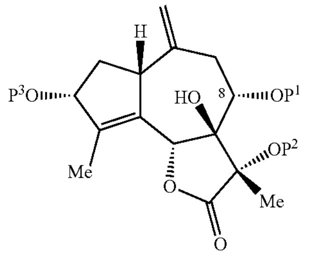

wherein R is either ester, amide and other related derivatives;

$P^1$, $P^2$, $P^3$ are independently hydroxyl protecting groups.

Synthesis of Compounds of Formula VIII

In one embodiment, conversion of a compound of Formula VII to a compound of Formula VIII was catalyzed by $Co(acac)_2$ in the presence of reducing agent $PhSiH_3$ and under an oxygen atmosphere. In some embodiments, other transition metal catalysts would also be suitable for this conversion, including, for example, $Co(tfa)_2$, $Co(dpm)_2$, Fe(pc), or $Mn(dpm)_2$. Other suitable reducing reagents would include, for example, $PhSiH_3$, $Et_3SiH$, or i-PrOH.

VII

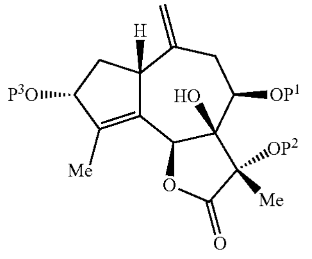

-continued

VIII

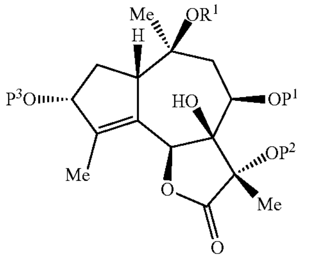

wherein $P^1$, $P^2$ and $P^3$ are independently hydroxyl protecting groups;

$R^1$ is H.

In another embodiment, the selective acylation of a compound of Formula VIII (wherein $P^1$, $P^2$, $P^3$ and $P^4$ are independently hydroxyl protecting groups; R is H) at elevated temperature provided a compound of Formula VIII (wherein $P^1$, $P^2$ and $P^3$ are independently hydroxyl protecting groups; $R^1$ is acyl group)

Synthesis of Compounds of Formula IX

In one embodiment, inversion of stereochemistry at C-8 position of a compound of Formula VIII was performed using deprotection/oxidation/reduction protocol to generate a compound of Formula IX. In some embodiments, oxidizing agents may be IBX, DMP, PCC and other oxidants known to the one skilled in the art; Reducing agents can be $NaBH_4$ and other reagents known to the one skilled in the art. Mitsunobu/hydrolysis protocol may be used to invert the stereochemistry of a compound of Formula VIII at C-8 position.

VIII

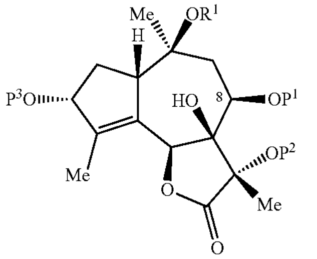

IX

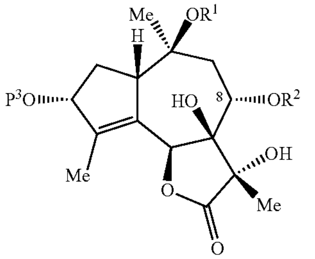

wherein $P^1$, $P^2$ and $P^3$ are independently hydroxyl protecting groups;

$R^1$ is acyl group;

$R^2$ is H.

Synthesis of Compounds of Formula X

In one embodiment, a series of thapsigargins of Formula X which do not have an oxygenated substituent at the C-2 position were synthesized from a compound of Formula IX.

IX

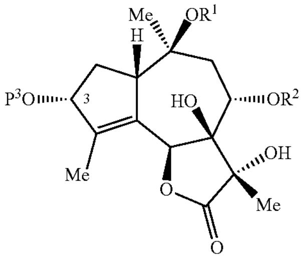

X

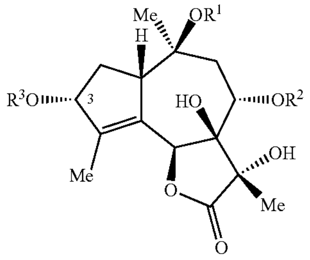

wherein $R^1$, $R^2$ and $R^3$ are independently H or acyl groups; $P^3$ is a hydroxyl protecting group.

Synthesis of Compounds of Formula XI

In one embodiment, conversion of a compound of Formula IX to a compound of Formula XI can be accomplished via one-pot manipulation comprising selective acylation at C-8 position and oxidation at C-3 position. In some embodiments, Jones reagent or other reagents, for example PCC, known to the one skilled in the art. can be used to achieve the oxidation.

IX

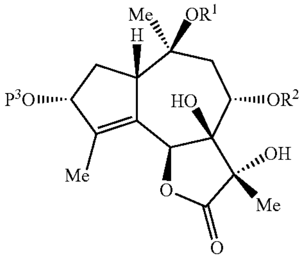

XI

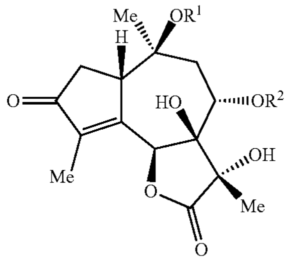

wherein $P^3$ is H or hydroxyl protecting group;

$R^1$ is an acyl group;

$R^2$ is H or an acyl group.

Synthesis of Compounds of Formula XII

In one embodiment, conversion of a compound of Formula XI to a compound of Formula XII was performed using an oxidation protocol. In some embodiments, $Mn(OR^3)_3$ was used, which may also be generated from $Mn(OAc)_3$ and $R^3OH$.

XI

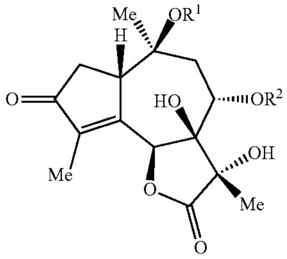

XII

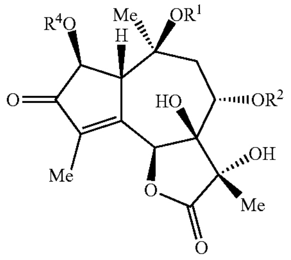

wherein $R^1$, $R^2$ and $R^4$ are independently acyl groups.

Synthesis of Compounds of Formula XIII

In one embodiment, stereoselective reduction of a compound of Formula XII provided a compound of Formula XIII. Common reducing reagents may be used such as, for example, $NaBH_4$ or Dibal-H. In some embodiments, $Zn(BH_4)_2$ is used since it gives a high level of stereoselectivity.

XII

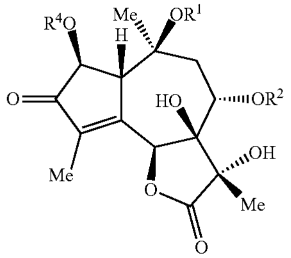

XIII

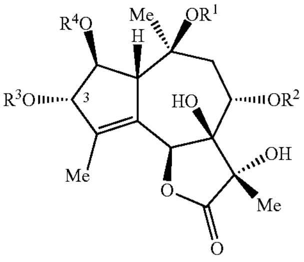

wherein $R^1$, $R^2$ and $R^4$ are independently acyl groups; $R^3$ is H.

In a further embodiment, selective acylation of a compound of Formula XIII (wherein $R^1$, $R^2$ and $R^4$ are independently acyl groups; $R^3$ is H) provided a compound of Formula XIII (wherein $R^1$, $R^2$, $R^3$ and $R^4$ are independently acyl groups)

Biological Activity

Thapsigargin is categorized as a highly selective subnanomolar inhibitor of intracellular calcium ion transport enzymes. Such enzymes are termed sarco/endoplasmic reticulum $Ca^{2+}$-ATPases (SERCAs) (Thastrup, O. et al. *Proc. Natl. Acad. Sci. U.S.A* 1990, 87: 2466-2470). The remarkably high level of selectivity towards SERCAs makes thapsigargin a particularly useful tool to investigate a variety of $Ca^{2+}$-dependent cellular processes (Treiman, M. et al. *Trends Pharmacol. Sci.* 1998, 19: 131-135). More significantly, the induction of cell apoptosis is also dependent on $Ca^{2+}$ signals, in which the strategic application of thapsigargin to promote the induction of programmed cancer cell death in a proliferation independent manner has led to the development of novel cancer therapeutics (Christensen, S. B. et al. *Anti-cancer Agents Med. Chem.* 2009, 9: 276-294). For example, as described herein, the prodrug, MIPSAGARGIN®, is currently in clinical trials for the treatment of cancer.

The following working examples further illustrate the present invention and are not intended to be limiting in any respect.

WORKING EXAMPLES

Materials and Methods

All reactions were carried out under an atmosphere of argon in anhydrous solvents using oven-dried or flame-dried glassware and commercially available reagents that were used as received, unless otherwise stated; Anhydrous dichloromethane (DCM), tetrahydrofuran (THF), diethyl ether ($Et_2O$), and toluene (PhMe) were obtained by passing degassed solvents through activated alumina columns in a Grubbs solvent purification system (PureSolv MD-6 of Innovative Technology Inc.); Hexamethylphosphoramide (HMPA) and dimethyl sulfoxide (DMSO) were distilled from $CaH_2$ under reduced pressure and stored over 4 Å molecular sieves; Triethylamine was distilled from $CaH_2$ under an atmosphere of argon. Analytical thin layer chromatography (t.l.c.) was performed on pre-coated 0.2 mm thick silica gel 60-$F_{254}$ plates (Merck) and visualized using UV light and by treatment with acidic vanillin solution (in EtOH), followed by heating. All compounds were purified by flash column chromatography using silica gel 60 (40-63 μm, Silicycle) and gave spectroscopic data consistent with being ≥95% the assigned structure. Melting points (uncorrected) were obtained from a Büchi M560 melting point instrument. Optical rotations ($[\alpha]_D^{20}$) were measured on an Anton Parr MCP 200 polarimeter with a tungsten halogen lamp (589 nm) at the stated temperature using a 0.7 mL quartz cell of 100 mm length; Solution concentrations (c) are given in g/100 mL; $^1$H NMR and $^{13}$C NMR spectra were recorded on Bruker Avance 600 spectrometers in $CDCl_3$ at ambient temperature; Chemical shifts (6) are given in ppm and calibrated using the signal of residual undeuterated solvent as internal reference for $^1$H NMR ($\delta_H$=7.26 ppm for $CDCl_3$) and using the signal of the deuterated solvent for $^{13}$C NMR ($\delta_C$=77.16 ppm for $CDCl_3$). $^1$H NMR data are reported as follows: chemical shift (multiplicity, coupling constant, integration). Coupling constants (J) are reported in Hz and apparent splitting patterns are designated using the following abbreviations: s (singlet), d (doublet), t (triplet), q(quartet), m (multiplet), br (broad) and the appropriate combinations thereof. IR spectra were recorded on an Agilent Technologies Cary 630 FT-IR (ATR) spectrometer; Wavenumbers (v) are given in $cm^{-1}$. Mass spectra were obtained through the Chemistry Department Mass Spectrometry Service at Queen's University.

Example 1. Syntheses of Indicated Compounds Including Compounds of Formula I

Synthesis of Compound SI-01: (R)-5-(3-Chloroprop-1-en-2-yl)-2-methylcyclohex-2-en-1-one

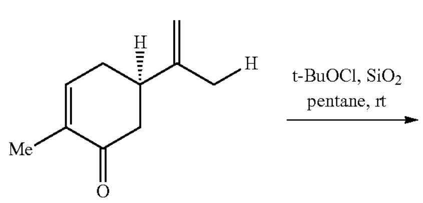

10

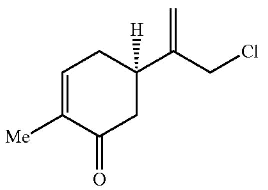

SI-01

To a solution of (R)-(−)-carvone (10) (3.03 g, 20.14 mmol, 1.0 equiv) in pentane (60 mL) was added silica gel (5.0 g) and then tert-butyl hypochlorite (2.73 ml, 24.17 mmol, 1.2 equiv) at room temperature. The solution was stirred at room temperature for 12 hours before being filtrated through a pad of silica gel and washed with $Et_2O$/pentane=1:4. The resulting solution was concentrated in vacuo to afford crude SI-01 as a yellow oil, which was used in the next step without further purification. A small portion of crude product was purified by flash column chromatography (silica gel, $Et_2O$/pentane=1:9) to afford SI-01 as a colorless oil. All spectral data matched the reported values (Nakamura, E., et al. *J. Am. Chem. Soc.* 1987, 109: 8056-8066).

Color and State: colorless oil $R_f$=0.48 ($Et_2O$/pentane=1:4; UV, vanillin)

$[\alpha]_D^{20}$ −41.5 (c=0.45, $CHCl_3$)

$^1$H NMR (600 MHz, $CDCl_3$) δ 6.75-6.73 (m, 1H), 5.25 (s, 1H), 5.05 (s, 1H), 4.09 (d, A of AB, $J_{AB}$=12.0 Hz, 1H), 4.07 (d, B of AB, $J_{AB}$=11.9 Hz, 1H), 2.96 (app. tt, J=11.9, 3.7 Hz, 1H), 2.65 (ddd, J=16.0, 3.7, 1.3 Hz, 1H), 2.55 (app. dtd, J=17.0, 5.5, 2.0 Hz, 1H), 2.37 (dd, J=16.0, 13.1 Hz, 1H), 2.31 (ddt, J=17.9, 10.7, 2.4, 1H), 1.78 (d, J=1.0 Hz, 3H).

IR (Neat) 2953, 2922, 2887, 1666, 1431, 1364, 1252, 1211, 1144, 1107, 1055, 1014, 962, 901, 802, 748, 714, 686 $cm^{-1}$.

HRMS (ESI, $[M+Na]^+$) calcd for $C_{10}H_{13}OClNa$ 207.0547, found 207.0541.

Synthesis of Compound 11: tert-Butyl(((1R,5R)-5-(3-chloroprop-1-en-2-yl)-2-methylcyclohex-2-en-1-yl)oxy)dimethylsilane

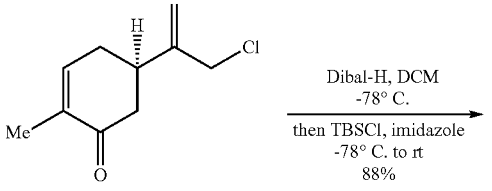

SI-01

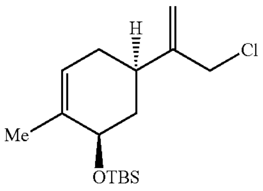

11

To a solution of crude SI-01 in DCM (100 ml) at −78° C. was added Dibal-H (1 M in hexanes, 22.16 ml, 22.16 mmol, 1.1 equiv), after 30 minutes, TBSCl (9.11 g, 60.4 mmol, 3.0 equiv) and imidazole (4.11 g, 60.4 mmol, 3.0 equiv) were added. The reaction was warmed to room temperature and further stirred for 12 hours before being quenched with slow addition of water (50 ml). The reaction mixture was partitioned between DCM (100 ml) and aqueous HCl (1 M, 200 ml). The organic phase was separated and washed with saturated (sat.) aqueous $NaHCO_3$ (200 ml), dried over anhydrous $MgSO_4$, filtered and concentrated in vacuo and the residue was purified by flash column chromatography (silica gel, DCM/hexanes=1:10) to afford allylic chloride 11 (5.33 g, 17.71 mmol, 88% yield) as a colorless oil. All spectral data matched the reported values (Ceschi M. A. et al. *J. Braz. Chem. Soc.* 2006, 2: 321-327).

Color and State: colorless oil $R_f$=0.25 (DCM/hexanes=1:4; vanillin)

$[\alpha]_D^{20}$ −44.0 (c=2.05, $CHCl_3$)

$^1$H NMR (600 MHz, $CDCl_3$) δ 5.47-5.44 (m, 1H), 5.18 (s, 1H), 5.02 (s, 1H), 4.30-4.25 (m, 1H), 4.09 (s, 2H), 2.50 (app. td, J=11.9, 3.3 Hz, 1H), 2.19-2.13 (m, 1H), 2.12-2.08 (m, 1H), 1.96-1.91 (m, 1H), 1.71 (br. s, 3H), 1.55 (td, J=12.4, 10.0 Hz, 1H), 0.92 (s, 9H), 0.11 (s, 3H), 0.10 (s, 3H).

IR (neat) 2951, 2928, 2886, 2855, 1641, 1449, 1361, 1343, 1301, 1251, 1217, 1090, 1061, 1040, 984, 963, 892, 832, 811, 772, 748, 673 $cm^{-1}$.

HRMS (ESI, $[M+Na]^+$) calcd for $C_{16}H_{29}OClNaSi$ 323.1568, found 323.1559.

Synthesis of Compound SI-03: Methyl (2S,3R)-4-(benzyloxy)-2,3-dihydroxy-2-methylbutanoate

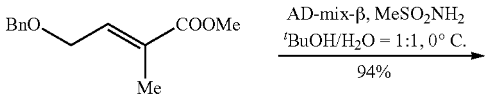

SI-02

-continued

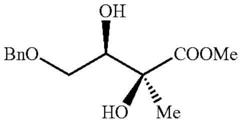

SI-03

To a solution of methyl (E)-4-(benzyloxy)-2-methylbut-2-enoate (SI-02) (21.0 g, 95.0 mmol, 1.0 equiv) in $H_2O$ (238 ml) and tBuOH (238 ml), $K_3[Fe(CN)_6]$ (105 g, 286 mmol, 3.0 equiv), $K_2CO_3$ (39.5 g, 286 mmol, 3.0 equiv), $NaHCO_3$ (24.0 g, 286 mmol, 3.0 equiv), $MeSO_2NH_2$ (9.2 g, 95 mmol, 1.0 equiv), $(DHQD)_2PHAL$ (547 mg, 0.667 mmol, 0.007 equiv) were added successively, followed by addition of $K_2OsO_4.2H_2O$ (0.105 g, 0.286 mmol) at 0° C. The reaction was stirred at 0° C. for 18 hours before quenched with sat. aqueous $Na_2SO_3$ (600 ml). The reaction mixture was extracted with EtOAc (300 ml) three times, dried over anhydrous $MgSO_4$, filtered and concentrated in vacuo and the residue was purified by flash column chromatography (silica gel, EtOAc/hexanes=1:3) to afford SI-03 (22.90 g, 90.0 mmol, 94% yield) as a colorless oil. Optical purity was determined by chiral HPLC analysis (CHIRALPAK AD-H column), hexane:2-propanol=90:10, flow rate=1.0 mL/min, $t_R$ (major)=18.6 min, $t_R$ (minor)=21.8 min, ee>99%.

Color and State: colorless oil

Rf=0.12 (EtOAc/hexanes=1:2; vanillin)

$[\alpha]_D^{20}$ +13.6 (c=1.19, $CHCl_3$)

$^1$H NMR (600 MHz, $CDCl_3$) δ 7.36-7.28 (m, 5H), 4.52 (s, 2H), 3.93 (ddd, J=6.9, 5.6, 4.2 Hz, 1H), 3.71 (s, 3H), 3.69-3.65 (m, 2H), 3.56 (s, 1H), 2.85 (d, J=6.9 Hz, 1H), 1.39 (s, 3H). $^{13}$C NMR (151 MHz, $CDCl_3$) δ 175.92, 137.65, 128.51, 127.94, 75.83, 74.42, 73.68, 69.85, 52.88, 22.28.

IR (neat) 3481, 2950, 2867, 1734, 1452, 1365, 1245, 1184, 1121, 1067, 980, 910, 823, 697 $cm^{-1}$.

HRMS (ESI, $[M+Na]^+$) calcd for $C_{13}H_{18}O_5Na$ 277.1046, found 277.1033.

Synthesis of Compound 9: Methyl (S)-4-(benzyloxy)-2-methyl-3-oxo-2-((trimethylsilyl)oxy)butanoate

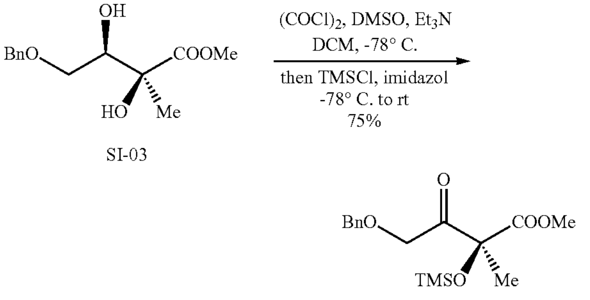

SI-03

9

To a solution of $(COCl)_2$ (9.18 ml, 105 mmol, 1.2 equiv) in DCM (500 ml) at −78° C. was added DMSO (18.60 ml, 262 mmol, 3.0 equiv) dropwise. After 30 minutes, the solution of SI-03 (22.22 g, 87 mmol, 1.0 equiv) in DCM (100 ml) was added and stirred at same temperature for 30 minutes. $Et_3N$ (30.4 ml, 218 mmol, 2.5 equiv) was added afterwards, and the reaction mixture was stirred for 30 minutes before warmed to 0° C. and further stirred for 30 minutes. After that, imidazole (29.7 g, 437 mmol, 5.0 equiv) and TMSCl (22.34 ml, 175 mmol, 2.0 equiv) were added at 0° C., and further stirred for 1 hour at the same temperature. The reaction was quenched with $H_2O$ (500 ml). The organic phase was separated and washed with sat. aqueous $NaHCO_3$ (1000 ml), dried over anhydrous $MgSO_4$, filtered and concentrated in vacuo and the residue was purified by flash column chromatography (silica gel, EtOAc/hexanes=1:20) to afford 9 (21.40 g, 65.9 mmol, 75%) as a colorless oil.

Color and State: colorless oil $R_f$=0.50 (EtOAc/hexanes=1:5; vanillin)

$[\alpha]_D^{20}$ −4.6 (c=1.34, $CHCl_3$)

$^1$H NMR (600 MHz, $CDCl_3$) δ 7.36-7.27 (m, 5H), 4.59 (d, A of AB, $J_{AB}$=11.7 Hz, 1H), 4.54 (d, B of AB, $J_{AB}$=12.0 Hz, 1H), 4.54 (d, A of AB, $J_{AB}$=18.5 Hz, 1H), 4.49 (d, B of AB, $J_{AB}$=18.4 Hz, 1H), 3.69 (s, 3H), 1.57 (s, 3H), 0.14 (s, 9H). $^{13}$C NMR (151 MHz, $CDCl_3$) δ 204.89, 170.78, 137.42, 128.46, 128.04, 127.95, 82.89, 73.28, 71.46, 52.75, 23.05, 1.63.

IR (neat) 3030, 2954, 2896, 1733, 1496, 1451, 1369, 1251, 1182, 1123, 1040, 1001, 945, 909, 840, 734, 697 $cm^{-1}$.

HRMS (ESI, $[M+Na]^+$) calcd for $C_{16}H_{24}O_5NaSi$ 347.1285, found 347.1279.

Synthesis of Compound 12: Methyl (2S,4R)-4-(benzyloxy)-6-((1R,5R)-5-((tert-butyldimethylsilyl)oxy)-4-methylcyclohex-3-en-1-yl)-2-methyl-3-oxo-2-((trimethylsilyl)oxy)hept-6-enoate

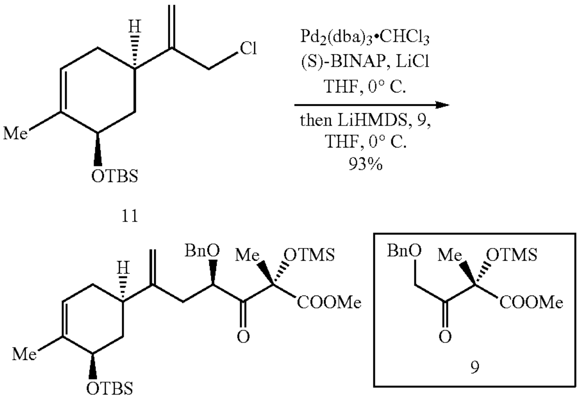

11

12

9

To the first flask containing $Pd_2(dba)_3.CHCl_3$ (0.259 g, 0.250 mmol, 0.01 equiv) and (S)-BINAP (0.623 g, 1.000 mmol, 0.04 equiv) and anhydrous lithium chloride (2.54 g, 60.0 mmol, 2.4 equiv) was added allylic chloride 11 (7.52 g, 25 mmol, 1.0 equiv) in THF (150 ml) at room temperature. The mixture was stirred for 30 minutes. In the second flask, to the solution of ketone 9 (8.92 g, 27.5 mmol, 1.1 equiv) in 75 ml THF was added LiHMDS (27.5 ml, 27.5 mmol, 1.1 equiv) dropwise at 0° C. The solution was stirred for 10 minutes. This enolate solution was transferred into the first flask at 0° C., and further stirred for 36 hours at the same temperature. The reaction was quenched with sat. aqueous $NH_4Cl$ (250 ml), and extracted with EtOAc (200 ml) three times. The combined organic phases were washed with brine (500 ml), dried over anhydrous $MgSO_4$, filtered and concentrated in vacuo. $^1$H NMR analysis of the crude product indicated an 8:1 diastereomeric ratio favoring the desired product 12. The crude product was purified by flash column chromatography (silica gel, EtOAc/hexanes=1:40 to 1:10) to afford 12 (13.68 g, 23.24 mmol, 93% yield) as a slightly yellow oil.

Color and State: slightly yellow oil $R_f$=0.46 (EtOAc/hexanes=1:10; vanillin)

$[\alpha]_D^{20}$ −25.3 (c=1.00, $CHCl_3$)

$^1$H NMR (600 MHz, $CDCl_3$) δ 7.33-7.27 (m, 5H), 5.44-5.40 (m, 1H), 4.88 (s, 1H), 4.86 (s, 1H), 4.72 (dd, X of ABX, $J_{AX}$=9.2 Hz, $J_{BX}$=3.1 Hz, 1H), 4.51 (d, A of AB, $J_{AB}$=11.5 Hz, 1H), 4.32 (d, B of AB, $J_{AB}$=11.5 Hz, 1H), 4.22-4.16 (m, 1H), 3.69 (s, 3H), 2.61 (dd, B of ABX, $J_{AB}$=15.2 Hz, $J_{BX}$=2.6 Hz, 1H), 2.30-2.26 (m, 1H), 2.23 (dd, A of ABX, $J_{AB}$=15.2 Hz, $J_{AX}$=9.2 Hz, 1H), 2.08-2.01 (m, 2H), 1.88-1.82 (m, 1H), 1.68 (br. s, 3H), 1.55 (s, 3H), 1.51 (td, J=12.5, 10.1 Hz, 1H), 0.91 (s, 9H), 0.16 (s, 9H), 0.09 (s, 3H), 0.08 (s, 3H). $^{13}$C NMR (151 MHz, $CDCl_3$) δ 207.40, 170.97, 149.41, 137.68, 137.15, 128.37, 128.08, 127.86, 123.32, 110.21, 83.30, 79.48, 72.38, 71.74, 52.73, 39.81, 38.94, 36.99, 31.93, 26.02, 23.95, 19.81, 18.26, 1.81, −3.99, −4.72.

IR (neat) 2929, 2855, 1753, 1730, 1641, 1451, 1366, 1343, 1250, 1186, 1159, 1121, 1091, 1060, 1004, 980, 893, 834, 772, 753, 696, 671 $cm^{-1}$.

HRMS (ESI, $[M+Na]^+$) calcd for $C_{32}H_{52}O_6NaSi_2$ 611.3195, found 611.3196.

Synthesis of Compound 8: Methyl (2S,4R)-4-(benzyloxy)-6-((1R,4R)-4-((tert-butyldimethylsilyl)oxy)-2-formyl-3-methylcyclopent-2-en-1-yl)-2-methyl-3-oxo-2-((trimethylsilyl)oxy) hept-6-enoate

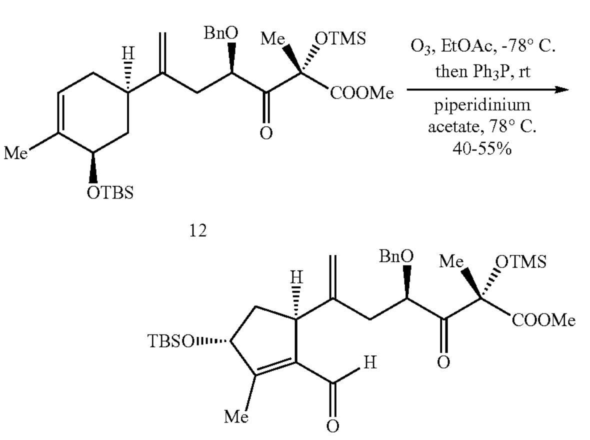

12

8

To a solution of 12 (2.50 g, 4.25 mmol, 1.0 equiv) in EtOAc (80 ml) at −78° C. was bubbling dry air/$O_3$. The reaction was carefully controlled by t.l.c. (checked in every 2 minutes to avoid over-oxidation) until full conversion. The reaction mixture was bubbled with dry air for 10 min before addition of triphenylphosphine (3.34 g, 12.74 mmol, 3.0 equiv) and slowly warmed to room temperature and further stirred for 10 hours. At this point, piperidinium acetate (0.123 g, 0.849 mmol, 0.2 equiv) was added and the reaction was heated to 78° C. for 12 hours. After cooled to room temperature, the reaction mixture was concentrated in vacuo and the residue was purified by flash column chromatography (silica gel, EtOAc/hexanes=1:20 to 1:10) to afford 8 (1.42 g, 2.35 mmol, 55% yield) as a colorless oil.

Color and State: colorless oil $R_f$=0.46 (EtOAc/hexanes=1:4; vanillin)

$[\alpha]_D^{20}$ −6.6 (c=0.89, $CHCl_3$)

$^1$H NMR (600 MHz, $CDCl_3$) δ 9.89 (s, 1H), 7.35-7.24 (m, 5H), 4.90 (s, 1H), 4.85 (s, 1H), 4.79 (dd, X of ABX, $J_{AX}$=9.1 Hz, $J_{BX}$=2.8 Hz, 1H), 4.55 (app. t, J=6.8 Hz, 1H), 4.47 (s, 2H), 3.68 (s, 3H), 3.38 (app. t, J=7.6 Hz, 1H), 2.62 (dd, B of ABX, $J_{AB}$=15.7 Hz, $J_{BX}$=2.5 Hz, 1H), 2.49 (dt, A of ABXY, $J_{AB}$=13.1 Hz, $J_{AX}$=$J_{AY}$=7.9 Hz, 1H), 2.30 (dd, A of ABX, $J_{AB}$=15.0 Hz, $J_{AX}$=9.1 Hz, 1H), 2.11 (s, 3H), 1.52 (s, 3H), 1.48 (dt, B of ABXY, $J_{AB}$=13.1 Hz, $J_{BX}$=$J_{BY}$=6.4 Hz, 1H), 0.90 (s, 9H), 0.16 (s, 9H), 0.09 (s, 3H), 0.06 (s, 3H). $^{13}$C NMR (126 MHz, $CDCl_3$) δ 207.53, 189.46, 171.09, 161.26, 148.22, 138.67, 137.95, 128.32, 128.26, 127.73, 112.45, 83.28, 79.48, 79.35, 72.52, 52.76, 47.37, 40.98, 37.88, 25.90, 23.91, 18.22, 12.06, 1.84, −4.31, −4.75.

IR (neat) 2952, 2931, 2856, 1751, 1729, 1675, 1496, 1447, 1364, 1251, 1187, 1160, 1121, 1098, 1025, 1003, 835, 776, 753, 697 $cm^{-1}$.

HRMS (ESI, $[M+H]^+$) calcd for $C_{32}H_{51}O_7Si_2$ 603.3168, found 603.3184.

Synthesis of Compound 7: (3S,3aR,4R,6aR,8R,9bS)-4-(Benzyloxy)-8-((tert-butyldimethylsilyl)oxy)-3a-hydroxy-3,9-dimethyl-6-methylene-3-((trimethylsilyl)oxy)-3a,4,5,6,6a,7,8,9b-octahydroazuleno[4,5-b]furan-2(3H)-one

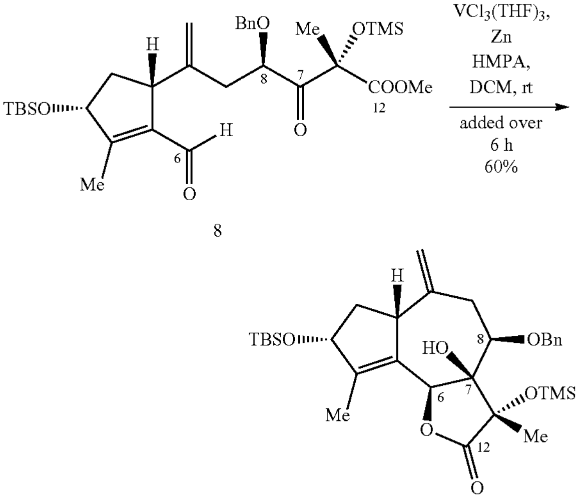

8

7

A mixture of $VCl_3(THF)_3$ (6.22 g, 16.33 mmol, 4.6 equiv) and zinc powder (0.65 g, 9.94 mmol, 2.8 equiv) in DCM (80 ml) was stirred for 30 minutes. After that, DCM (100 ml) and HMPA (7.41 ml, 42.6 mmol, 12 equiv) were added, then followed by addition of 8 (2.14 g, 3.55 mmol, 1.0 equiv) in DCM (20 ml) over 6 hours. The reaction was quenched with aqueous sat. aqueous potassium sodium tartrate solution (250 ml) and sat. aqueous $NaHCO_3$ (100 ml), and vigorously stirred for 3 hours. The organic phase was separated and washed with water (300 ml) twice and brine (300 ml) once, dried over anhydrous $MgSO_4$, filtered and concentrated in vacuo and the residue was purified by flash column chromatography (silica gel, EtOAc/hexanes=1:20) to afford 7 (1.22 g, 2.12 mmol, 60% yield) as a colorless sticky oil.

Color and State: colorless oil $R_f$=0.31 (EtOAc/hexanes=1:10; vanillin)

$[\alpha]_D^{20}$ −87.4 (c=0.43, $CHCl_3$)

$^1$H NMR (600 MHz, $CDCl_3$) δ 7.39-7.32 (m, 5H), 5.24 (br. s, 1H), 4.92 (s, 1H), 4.88 (s, 1H), 4.72 (d, A of AB, $J_{AB}$=11.0 Hz, 1H), 4.56 (app. t, 7.1 Hz, 1H), 4.52 (d, B of AB, $J_{AB}$=11.0 Hz, 1H), 4.10 (t, X of ABX, $J_{AX}$=$J_{BX}$=4.9 Hz, 1H), 3.70 (app. t, 8.6 Hz, 1H), 2.83 (s, 1H), 2.49 (dd, A of ABX, $J_{AB}$=13.5 Hz, $J_{AX}$=5.3 Hz, 1H), 2.46 (dt, A of ABXY, $J_{AB}$=11.9 Hz, $J_{AX}$=$J_A$Y=6.2 Hz, 1H), 2.33 (dd, B of ABX, $J_{AB}$=13.6 Hz, $J_{BX}$=4.3 Hz, 1H), 1.85 (s, 3H), 1.49 (ddd, B of ABXY, $J_{AB}$=12.0 Hz, $J_{BX}$=10.2 Hz, $J_B$Y=8.2 Hz, 1H), 1.44 (s, 3H), 0.92 (s, 9H), 0.18 (s, 9H), 0.11 (s, 3H), 0.09 (s, 3H). $^{13}$C NMR (151 MHz, $CDCl_3$) δ 175.85, 146.65, 146.15, 137.41, 131.07, 128.70, 128.37, 128.27, 112.32, 82.51, 79.23, 78.86, 78.01, 74.11, 71.47, 48.07, 42.86, 36.59, 26.03, 18.35, 17.58, 12.32, 1.48, −4.32, −4.65.

IR (neat) 3544, 2929, 2953, 2856, 1781, 1443, 1350, 1285, 1251, 1217, 1187, 1144, 1121, 1074, 1024, 1005, 987, 968, 940, 888, 836, 775, 754, 733, 697, 669 $cm^{-1}$.

HRMS (ESI, $[M-H]^-$) calcd for $C_{31}H_{47}O_6Si_2$ 571.2917, found 571.2934.

Synthesis of Compound 13: (3S,3aR,4R,6S,6aS,8R,9bS)-4-(benzyloxy)-8-((tert-butyldimethylsilyl)oxy)-3a,6-dihydroxy-3,6,9-trimethyl-3-((trimethylsilyl)oxy)-3a,4,5,6,6a,7,8,9b-octahydroazuleno[4,5-b]furan-2(3H)-one

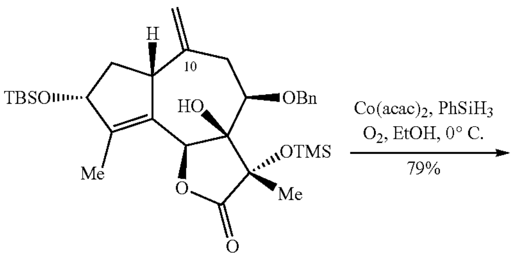

7

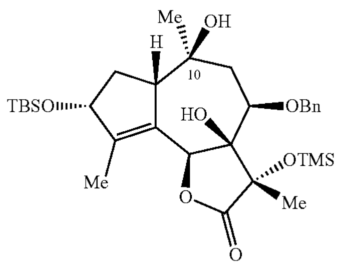

13

Through a solution of 7 (1.72 g, 3.00 mmol, 1.0 equiv) and $Co(acac)_2$ (0.232 g, 0.901 mmol, 0.3 equiv) in anhydrous EtOH (37.5 ml) was bubbling $O_2$ for 10 minutes at 0° C. After that, $PhSiH_3$ (0.953 ml, 7.51 mmol, 2.5 equiv) was added over 1 hour. The deep green reaction mixture was further stirred for 1 hour at 0° C. before quenched with sat. aqueous $Na_2S_2O_3$ (15 ml), sat. aqueous $NaHCO_3$ (10 ml) and EtOAc (15 ml). The mixture was vigorously stirred for 24 hours at room temperature before extracted with EtOAc (50 ml) three times. The combined organic phases were washed with brine (100 ml), dried over anhydrous $MgSO_4$, filtered and concentrated in vacuo and the residue was purified by flash column chromatography (silica gel, EtOAc/hexanes=1:4) to afford 13 (1.40 g, 2.37 mmol, 79% yield) as a colorless crystalline solid.

Color and State: colorless crystalline solid

Melting Point: 176.1-178.5° C.

$R_f$=0.42 (EtOAc/hexanes=1:2; vanillin)

$[\alpha]_D^{20}$ −72.3 (c=0.37, $CHCl_3$)

$^1$H NMR (600 MHz, $CDCl_3$) δ 7.38-7.31 (m, 5H), 5.21-5.18 (m, 1H), 4.62 (d, A of AB, $J_{AB}$=10.7 Hz, 1H), 4.53 (d, B of AB, $J_{AB}$=10.6 Hz, 1H), 4.52 (app. t, 5.7 Hz, 1H), 3.94 (dd, X of ABX, $J_{AX}$=11.0 Hz, $J_{BX}$=4.7 Hz, 1H), 3.21 (app. td, 7.6 Hz, 2.5 Hz, 1H), 2.35 (dt, A of ABXY, $J_{AB}$=12.8 Hz, $J_{AX}$=$J_A$Y=7.5 Hz, 1H), 2.31 (d, J=1.6 Hz, 1H), 2.12 (dd, B of ABX, $J_{AB}$=13.2 Hz, $J_{BX}$=4.7 Hz, 1H), 2.04 (app. t, A of ABX, $J_{AB}$=$J_{AX}$=12.1 Hz, 1H), 1.86 (br. s, 3H), 1.52 (ddd, B of ABXY, $J_{AB}$=13.1 Hz, $J_{BX}$=7.9 Hz, $J_{BY}$=6.8 Hz, 1H), 1.49 (s, 3H), 1.43 (s, 1H), 1.07 (s, 3H), 0.91 (s, 9H), 0.22 (s, 9H), 0.09 (s, 3H), 0.08 (s, 3H). $^{13}$C NMR (151 MHz, $CDCl_3$) δ 175.39, 146.10, 137.43, 128.73, 128.45, 128.31, 127.94, 83.56, 80.31, 79.45, 77.70, 75.25, 72.79, 72.22, 53.70, 45.29, 35.89, 26.05, 22.19, 18.33, 18.15, 12.97, 1.54, −4.30, −4.66.

IR (neat) 3497, 2952, 2929, 2895, 2855, 1781, 1456, 1405, 1359, 1290, 1252, 1220, 1193, 1131, 1089, 1062, 1028, 1009, 937, 906, 869, 860, 839, 776, 737, 698, 667 $cm^{-1}$.

HRMS (ESI, $[M+Na]^+$) calcd for $C_{31}H_{49}O_7NaSi_2$ 613.2987, found 613.2958.

Synthesis of Compound 14: (3S,3aR,4R,6S,6aS,8R,9bS)-4-(benzyloxy)-8-((tert-butyldimethylsilyl)oxy)-3a-hydroxy-3,6,9-trimethyl-2-oxo-3-((trimethylsilyl)oxy)-2,3,3a,4,5,6,6a,7,8,9b-decahydroazuleno[4,5-b]furan-6-yl acetate

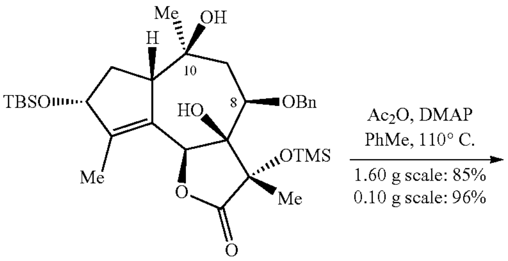

13

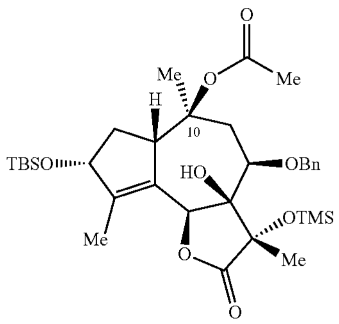

14

To a solution of 13 (1.67 g, 2.83 mmol, 1.0 equiv) and DMAP (0.38 g, 3.11 mmol, 1.1 equiv) in PhMe (56 ml) was added acetic anhydride (2.6 ml, 28.3 mmol, 10.0 equiv), then the reaction was stirred for 6 hours at 110° C. After cooled to room temperature, the solution was directly applied to flash column chromatography (silica gel, EtOAc/hexanes=1:10) to afford 14 (1.52 g, 2.40 mmol, 85% yield) as a white foam.

Color and State: white foam $R_f$=0.50 (EtOAc/hexanes=1:4; vanillin)

$[\alpha]_D^{20}$ −67.6 (c=0.49, $CHCl_3$)

$^1$H NMR (600 MHz, $CDCl_3$) δ 7.37-7.31 (m, 5H), 5.19-5.16 (m, 1H), 4.63 (d, J=10.6 Hz, 1H), 4.51-4.49 (m, 2H), 3.95 (dd, J=10.9, 5.3 Hz, 1H), 3.87 (app. td, J=7.9, 2.2 Hz, 1H), 2.65-2.58 (m, 2H), 2.31 (d, J=1.5 Hz, 1H), 2.26 (dt, A of ABXY, $J_{AB}$=13.0 Hz, $J_{AX}$=$J_{AY}$=7.5 Hz, 1H), 1.99 (s, 3H), 1.86 (s, 3H), 1.49 (s, 3H), 1.46 (ddd, B of ABXY, $J_{AB}$=13.3 Hz, $J_{BX}$=8.1 Hz, $J_{BY}$=6.6 Hz, 1H), 1.27 (s, 3H), 0.91 (s, 9H), 0.21 (s, 9H), 0.09 (s, 3H), 0.07 (s, 3H). $^{13}$C NMR (151 MHz, $CDCl_3$) δ 175.40, 170.42, 146.46, 137.43, 128.62, 128.24, 128.14, 127.22, 83.78, 83.72, 80.43, 79.25, 77.60, 75.21, 72.55, 50.98, 38.66, 36.11, 26.03, 22.67, 20.15, 18.29, 18.22, 13.06, 1.53, −4.29, −4.64.

IR (neat) 3451, 2952, 2929, 2869, 2856, 1728, 1716, 1497, 1458, 1364, 1249, 1194, 1147, 1128, 1091, 1025, 971, 940, 836, 775, 735, 698, 669 $cm^{-1}$.

HRMS (ESI, $[M-H]^-$) calcd for $C_{33}H_{51}O_8Si_2$ 631.3128, found 631.3104.

Synthesis of Compound 6: (3S,3aR,4S,6S,6aS,8R,9bS)-8-((tert-Butyldimethylsilyl)oxy)-3,3a,4-trihydroxy-3,6,9-trimethyl-2-oxo-2,3,3a,4,5,6,6a,7,8,9b-decahydroazuleno[4,5-b]furan-6-yl acetate

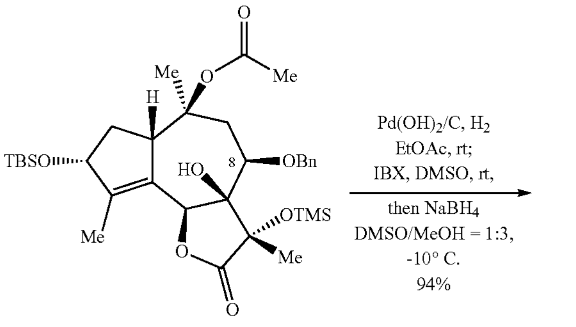

14

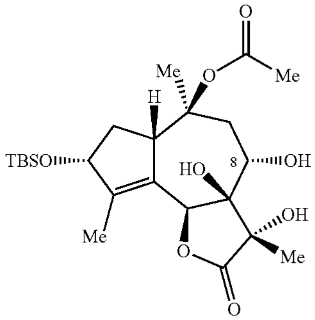

6

To a solution of 14 (1.34 g, 2.12 mmol, 1.0 equiv) in EtOAc (42 ml) was added $Pd(OH)_2/C$ (20 wt %, 0.59 g). The suspension was gently evacuated and refilled with $H_2$ and repeated three times. Then the reaction mixture was stirred under $H_2$ (balloon pressure) for 20 minutes before bubbling with argon for 20 minutes. After removing $Pd(OH)_2/C$ catalyst by filtration and solvents in vacuo, the residue was dissolved in DMSO (15 ml) followed by addition of IBX (2.96 g, 10.59 mmol, 5.0 equiv). The reaction mixture was stirred at room temperature overnight (~12 hours). After that, to this solution was added MeOH (45 ml) and stirred for 15 minutes before $NaBH_4$ (0.24 g, 6.35 mmol, 3.0 equiv) was added at −10° C. After 5 minutes, the reaction mixture was diluted with sat. aqueous $NH_4Cl$ (150 ml) and extracted with EtOAc (100 ml) three times. The combined organic phases were washed with sat. aqueous $NaHCO_3$ (200 ml) twice, dried over anhydrous $MgSO_4$, filtered and concentrated in vacuo. The residue was dissolved in MeOH (50 ml) and slowly concentrated, repeated 5 times. The crude product was purified by flash column chromatography (silica gel, EtOAc/hexanes=1:1) to afford 6 (0.93 g, 1.98 mmol, 94% yield) as a white foam.

Color and State: white foam $R_f$=0.22 (EtOAc/hexanes=1:1; vanillin)

$[\alpha]_D^{20}$ −64.7 (c=0.21, $CHCl_3$)

$^1$H NMR (600 MHz, $CDCl_3$) δ 5.81 (br. s, 1H), 4.94 (s, 1H), 4.50 (t, J=6.5 Hz, 1H), 4.34 (app. t, X of ABX, $J_{AX}$=$J_{BX}$=3.4 Hz, 1H), 4.29 (s, 1H), 4.04 (app. t, J=7.3 Hz, 1H), 3.08 (s, 1H), 2.90 (app. dd, A of ABX, $J_{AB}$=14.6 Hz, $J_{AX}$=3.6 Hz, 1H), 2.30 (dd, B of ABX, $J_{AB}$=14.3 Hz, $J_{BX}$=3.0 Hz, 1H), 2.18 (dt, A of ABXY, $J_{AB}$=13.1 Hz, $J_{AX}$=$J_{AY}$=7.5 Hz, 1H), 1.97 (s, 3H), 1.85 (s, 3H), 1.52 (dt, B of ABXY, $J_{AB}$=13.1 Hz, $J_{BX}$=$J_{BY}$=7.0 Hz, 1H), 1.47 (s, 3H), 1.36 (s, 3H), 0.91 (s, 9H), 0.09 (s, 3H), 0.07 (s, 3H). $^{13}$C NMR (151 MHz, $CDCl_3$) δ 176.01, 171.62, 147.23, 126.97, 87.21, 79.83, 79.60, 78.58, 77.76, 69.13, 50.36, 39.71, 35.67, 26.02, 22.77, 22.35, 18.29, 16.46, 13.04, −4.27, −4.63.

IR (neat) 3356, 2952, 2929, 2886, 2856, 2687, 1764, 1727, 1700, 1461, 1438, 1365, 1248, 1181, 1126, 1092, 1068, 1025, 983, 957, 938, 911, 873, 834, 810, 775, 736, 703, 669 $cm^{-1}$.

HRMS (ESI, $[M-H]^-$) calcd for $C_{23}H_{37}O_8Si$ 469.2263, found 469.2251.

Synthesis of Compound 15: (3S,3aR,4S,6S,6aS,9bS)-6-Acetoxy-3,3a-dihydroxy-3,6,9-trimethyl-2,8-dioxo-2,3,3a,4,5,6,6a,7,8,9b-decahydroazuleno[4,5-b]furan-4-yl butyrate

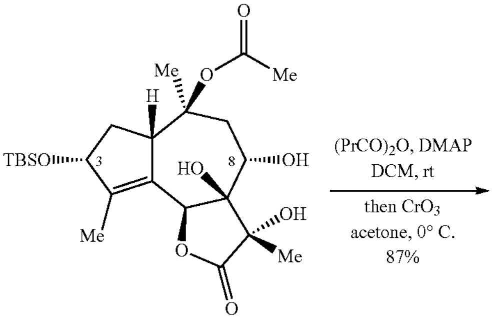

6

-continued

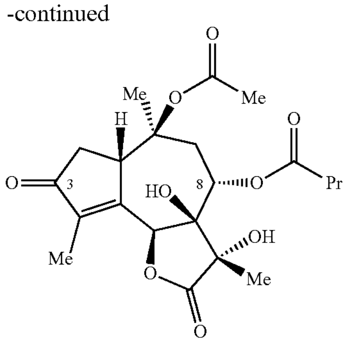

15

Butyric anhydride (79 μl, 0.472 mmol) was added to a solution of alcohol 6 (111.0 mg, 0.236 mmol) and DMAP (5.8 mg, 0.047 mmol) in DCM (5 ml). The reaction solution was stirred for ca. 1 hour (t.l.c. control) at room temperature before acetone (15 ml), one drop of water. Jones reagent (0.5 ml, 0.990 mmol, 2 M) was added in two portions (ca. 30 minutes' interval) at 0° C. The reaction mixture was stirred for ca. 5 hours (t.l.c. control) at the same temperature before quenched with iPrOH (0.5 ml). The resulting mixture was portioned between sat. aqueous $NaHCO_3$ (100 ml) and EtOAc (50 ml). The organic phases were combined, washed with brine (50 ml), dried over anhydrous MgSO4, filtered and concentrated in vacuo to afford the crude product. Purification by flash column chromatography (silica gel, EtOAc/hexanes=1:2) afforded the enone 15 (86.7 mg, 87% yield) as a white solid. All spectral data matched the reported values (Doan, N. T. Q. et al. *J. Nat. Prod.* 2015, 78: 1406-1414).

Color and State: white foam $R_f$=0.30 (EtOAc/hexanes=1:1; vanillin)

$[\alpha]_D^{20}$ −49.0 (c=0.35, $CHCl_3$)

$^1H$ NMR (600 MHz, $CDCl_3$) δ 5.81 (s, 1H), 5.71 (t, X of ABX, $J_{AX}$=$J_{BX}$=3.3 Hz, 1H), 4.78-4.75 (m, 1H), 4.19 (s, 1H), 3.32 (dd, A of ABX, $J_{AB}$=14.5 Hz, $J_{AX}$=3.0 Hz, 1H), 3.20 (s, 1H), 2.42 (dd, J=19.4, 6.4 Hz, 1H), 2.34 (dd, J=19.5, 1.9 Hz, 1H), 2.27 (t, X of $A_3M_2X_2$, $J_{MX}$=7.5 Hz, 2H), 2.09 (dd, B of ABX, $J_{AB}$=14.5 Hz, $J_{BX}$=3.4 Hz, 1H), 1.98 (s, 3H), 1.92 (br. s, 3H), 1.61 (sext d, M (or M') of $A_3MM'X_2$, $J_{AM}$=$J_{AM'}$=$J_{MX}$=$J_{M'X'}$=7.3 Hz, $J_{MM'}$=1.9 Hz, 2H), 1.50 (s, 3H), 1.20 (s, 3H), 0.93 (t, A of $A_3M_2X_2$, $J_{AM}$=7.4 Hz, 3H).

IR (neat) 3416, 2966, 2935, 2876, 1792, 1734, 1701, 1692, 1447, 1369, 1303, 1245, 1166, 1080, 1048, 1019, 986, 965, 937, 887, 861, 808, 782, 735, 700, 663 $cm^{-1}$.

HRMS (ESI, $[M-H]^-$) calcd for $C_{21}H_{27}O_9$ 423.1661, found 423.1645.

Synthesis of Compound 16: (3S,3aR,4S,6S,6aR,7S,9bS)-6-Acetoxy-4-(butyryloxy)-3,3a-dihydroxy-3,6,9-trimethyl-2,8-dioxo-2,3,3a,4,5,6,6a,7,8,9b-decahydroazuleno[4,5-b]furan-7-yl octanoate

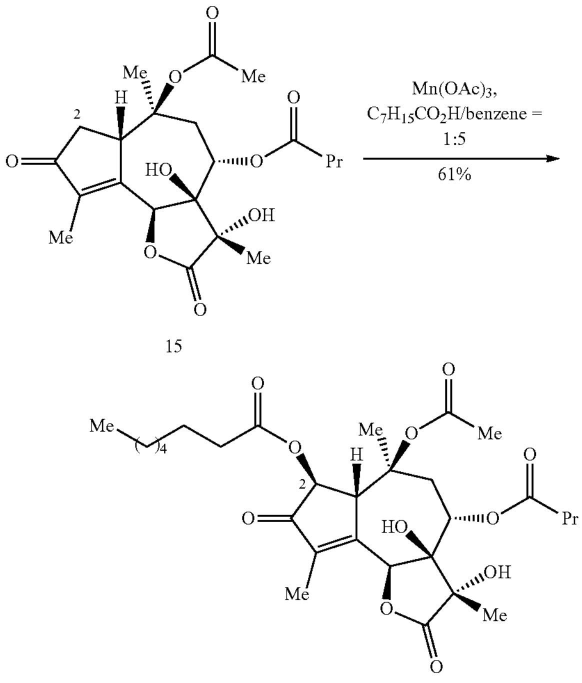

15

16

$Mn(OAc)_3.2H_2O$ (399.0 mg, 1.414 mmol) was added to a solution of enone 15 (100.0 mg, 0.236 mmol) in octanic acid (6 ml) and benzene (30 ml). The reaction mixture was refluxed for ca. 4 hours while removing water with a Dean-Stark apparatus. The brown reaction mixture was cooled to room temperature and portioned between sat. aqueous $NaHCO_3$ (100 ml) and EtOAc (50 ml). The organic phases were combined, washed with sat. aqueous $NaHCO_3$ (100 ml) five times, dried over anhydrous $MgSO_4$, filtered and concentrated in vacuo to afford the crude product. Purification by flash column chromatography (silica gel, EtOAc/hexanes=1:2) afforded a brown foam which was further crystallized from $Et_2O$ to give the enone 16 (81.5 mg, 61% yield) as a white solid. (Crestey, F. et al. *Tetrahedron Lett.* 2015, 56:5896-5898).

Color and State: white solid

Melting Point: 161.5-162.0° C.

$R_f$=0.52 (EtOAc/hexanes=1:1; vanillin)

$[\alpha]_D^{20}$ −89.6 (c=0.44, $CHCl_3$)

$^1H$ NMR (600 MHz, $CDCl_3$) δ 5.82 (br. s, 1H), 5.68 (t, J=3.7 Hz, 1H), 5.23-5.21 (m, 1H), 4.54-4.51 (m, 1H), 3.26 (s, 1H), 3.20 (dd, J=14.7, 3.2 Hz, 1H), 2.58 (s, 1H), 2.39-2.26 (m, 5H), 2.01-1.99 (m, 3H), 1.94 (s, 3H), 1.66-1.58 (m, 4H), 1.49 (s, 3H), 1.39 (s, 3H), 1.34-1.23 (m, 8H), 0.95 (t, J=7.4 Hz, 3H), 0.87 (t, J=6.9 Hz, 3H).

IR (neat) 3400, 2954, 2928, 2856, 1793, 1718, 1632, 1457, 1413, 1368, 1301, 1241, 1159, 1124, 1079, 1047, 1018, 992, 961, 914, 862, 811, 768, 731 $cm^{-1}$.

HRMS (ESI, $[M-H]^-$) calcd for $C_{29}H_{41}O_{11}$ 565.2654, found 565.2637.

Synthesis of Thapsigargin (1)

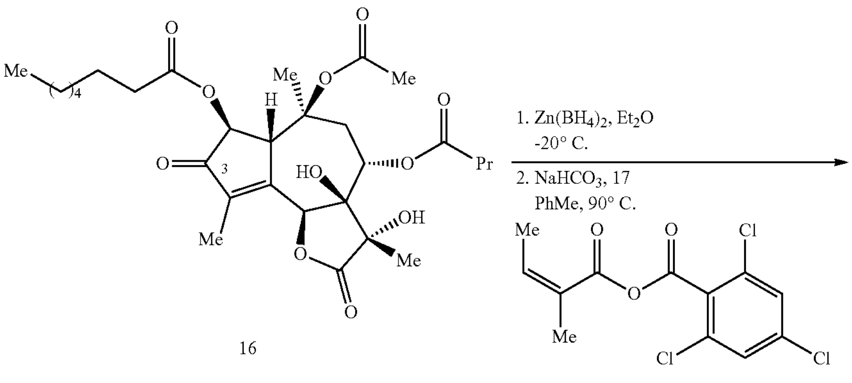

16

17

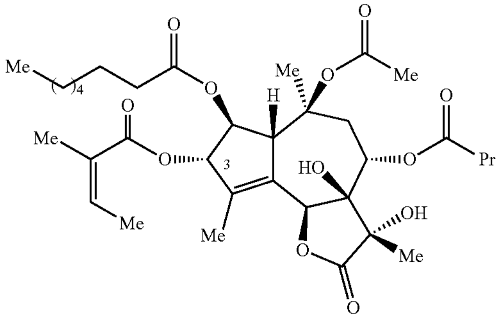

Thapsigargin (1)

To a solution of 16 (10 mg, 0.018 mmol, 1.0 equiv) in $Et_2O$ (2 ml) at −20° C. was added $Zn(BH_4)_2$ (~0.5 M in $Et_2O$, 0.42 ml, 0.21 mmol, 12.0 equiv) dropwise. After 5 hours, another portion of $Zn(BH_4)_2$ (~0.5 M in $Et_2O$, 0.42 ml, 0.21 mmol, 12.0 equiv) was added dropwise and the reaction mixture was further stirred for 5 hours. The reaction solution was diluted with EtOAc (20 ml) and sat. aqueous NaEDTA (100 ml). The organic phase was separated and washed with brine (50 ml), dried over anhydrous $Na_2SO_4$, filtered and concentrated in vacuo to afforded crude product SI-04.

To the mixture of the resulting crude alcohol SI-04, anhydride 17 (54.1 mg, 0.176 mmol, 10.0 equiv) and $NaHCO_3$ (29.5 mg, 0.352 mmol, 20.0 equiv) was added PhMe (0.5 ml), then the reaction was stirred for 45 hours at 90° C. After cooled to room temperature, the solution was directly applied to flash column chromatography (silica gel, EtOAc/hexanes=1:3) to afford thapsigargin (7.3 mg, 0.011 mmol, 64% yield) as a white foam.

Color and State: white foam $R_f$=0.37 (EtOAc/hexanes=1:2; vanillin)

$[\alpha]_D^{20}$ −53.8 (c=0.12, $CHCl_3$)

$^1H$ NMR (600 MHz, $CDCl_3$) δ 6.11 (qq, J=7.2, 1.5 Hz, 1H), 5.68 (br. s, 1H), 5.65 (br. s, 1H), 5.63 (t, J=3.6 Hz, 1H), 5.48 (t, J=3.3 Hz, 1H), 4.29-4.26 (m, 1H), 3.39 (s, 1H), 3.04 (dd, J=14.6, 3.1 Hz, 1H), 2.77 (br. s, 1H), 2.36-2.24 (m, 5H), 1.99 (dq, J=7.3, 1.7 Hz, 3H), 1.93-1.91 (m, 3H), 1.89 (br. s, 3H), 1.86 (br. s, 3H), 1.65-1.55 (m, 4H), 1.48 (s, 3H), 1.39 (s, 3H), 1.33-1.21 (m, 8H), 0.94 (t, J=7.4 Hz, 3H), 0.86 (t, J=6.9 Hz, 3H). $^{13}C$ NMR (151 MHz, $CDCl_3$) δ 175.47, 172.75, 172.71, 170.99, 167.22, 141.99, 138.92, 130.25, 127.56, 84.72, 84.27, 78.77, 78.71, 77.85, 76.99, 66.28, 57.67, 38.39, 36.69, 34.36, 31.82, 29.21, 29.13, 24.97, 23.04, 22.75, 22.73, 20.73, 18.13, 16.37, 15.97, 14.23, 13.85, 13.12.

IR (neat) 3437, 2954, 2926, 2856, 1791, 1771, 1738, 1717, 1648, 1457, 1414, 1369, 1303, 1234, 1198, 1158, 1128, 1098, 1042, 1020, 985, 951, 853, 800, 729 $cm^{-1}$.

HRMS (ESI, $[M+Na]^+$) calcd for $C_{34}H_{50}O_{12}Na$ 673.3194, found 673.3198.

Synthesis of Compound 18: (3S,3aR,4S,6S,6aS,8R, 9bS)-6-Acetoxy-3,3a,8-trihydroxy-3,6,9-trimethyl-2-oxo-2,3,3a,4,5,6,6a,7,8,9b-decahydroazuleno[4,5-b]furan-4-yl Butyrate

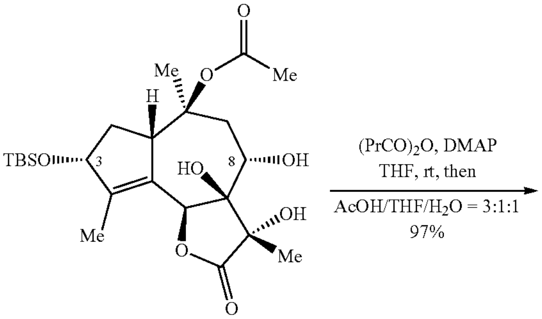

6

-continued

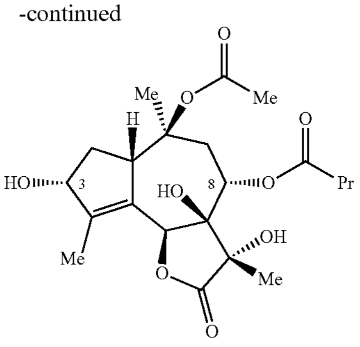

18

-continued

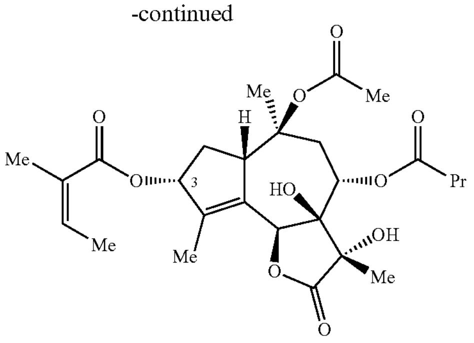

Nortrilobolide (3)

Butyric anhydride (69 μl, 0.425 mmol) was added to a solution of alcohol 6 (100.0 mg, 0.212 mmol) and DMAP (5.2 mg, 0.042 mmol) in THF (3 ml). The reaction solution was stirred for ca. 5 hours (t.l.c. control) at room temperature before added $H_2O$ (3 ml) and AcOH (9 ml). The reaction solution was further stirred for ca. 24 hours before concentrated in vacuo to afford the crude product. Purification by flash column chromatography (silica gel, EtOAc/hexanes=1:2) afforded the alcohol 18 (88.2 mg, 97% yield) as a white foam. (Doan, N. T. Q. et al. *J. Nat. Prod.* 2015, 78: 1406-1414).

Color and State: white foam $R_f$=0.19 (EtOAc/hexanes=1:1; vanillin)

$[\alpha]_D^{20}$ −51.9 (c=0.36, $CHCl_3$)

$^1H$ NMR (600 MHz, $CDCl_3$) δ 5.69 (br. s, 1H), 5.61 (t, X of ABX, $J_{AX}$=$J_{BX}$=3.7 Hz, 1H), 4.59 (app. q, J=6.6 Hz, 1H), 4.19 (app. t, J=6.9 Hz, 1H), 3.71 (s, 1H), 3.10 (dd, A of ABX, $J_{AB}$=14.9 Hz, $J_{AX}$=3.3 Hz, 1H), 2.66 (s, 1H), 2.39 (dt, J=14.0, 8.2 Hz, 1H), 2.28 (s, 1H), 2.27 (t, J=7.7 Hz, 2H), 2.19 (dd, B of ABX, $J_{AB}$=14.7 Hz, $J_{BX}$=4.0 Hz, 1H), 1.97 (s, 3H), 1.95 (br. s, 3H), 1.80 (d, J=6.3 Hz, 1H), 1.66-1.59 (m, 3H), 1.48 (s, 3H), 1.33 (s, 3H), 0.94 (t, J=7.4 Hz, 3H).

IR (neat) 3402, 2971, 2937, 2873, 1765, 1704, 1445, 1368, 1305, 1242, 1166, 1124, 1097, 1047, 1017, 979, 957, 894, 859, 775, 735, 702, 666 $cm^{-1}$.

HRMS (ESI, $[M-H]^-$) calcd for $C_{21}H_{29}O_9$ 425.1817, found 425.1830.

Synthesis of Nortrilobolide (3)

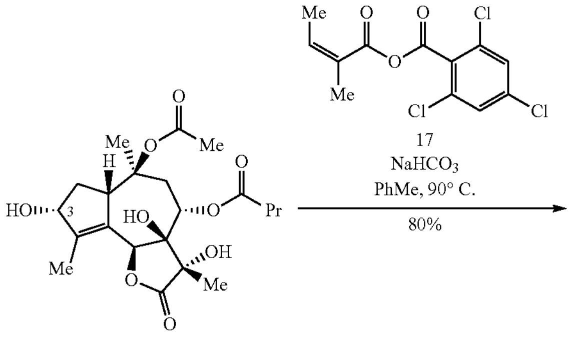

18

To a mixture of 18 (15 mg, 0.035 mmol, 1.0 equiv), mixed anhydride 17 (76 mg, 0.246 mmol, 10.0 equiv) and $NaHCO_3$ (59 mg, 0.0.703 mmol, 20.0 equiv) was added PhMe (1 ml), then the reaction was stirred for 6 hours at 90° C. After cooled to room temperature, the solution was directly applied to flash column chromatography (silica gel, EtOAc/hexanes=1:2) to afford nortrilobolide (3) (14.3 mg, 0.028 mmol, 80% yield) as a white foam.

Color and State: white foam $R_f$=0.45 (EtOAc/hexanes=1:1; vanillin)

$[\alpha]_D^{20}$ −68.6 (c=0.24, $CHCl_3$)

$^1H$ NMR (600 MHz, $CDCl_3$) δ 6.11 (qq, J=7.3, 1.5 Hz, 1H), 5.70 (br. s, 1H), 5.63 (t, X of ABX, $J_{AX}$=$J_{BX}$=3.6 Hz, 1H), 5.58 (app. t, J=4.7 Hz, 1H), 4.37-4.34 (m, 1H), 3.29 (s, 1H), 3.12 (dd, A of ABX, $J_{AB}$=14.8 Hz, $J_{AX}$=3.6 Hz, 1H), 3.13 (br. s, 1H), 2.54 (dt, J=14.8, 8.5 Hz, 1H), 2.27 (t, J=7.5 Hz, 2H), 2.16 (dd, B of ABX, $J_{AB}$=14.6 Hz, $J_B$x=3.8 Hz, 1H), 2.01 (app. dq, J=7.2, 1.6 Hz, 3H), 1.97 (s, 3H), 1.91-1.89 (m, 6H), 1.66-1.60 (m, 3H), 1.48 (s, 3H), 1.30 (s, 3H), 0.94 (t, J=7.4 Hz, 3H). $^{13}C$ NMR (151 MHz, $CDCl_3$) δ 175.51, 172.72, 171.02, 167.83, 143.75, 138.71, 131.29, 127.89, 85.85, 79.71, 78.87, 78.83, 77.65, 66.58, 51.02, 38.63, 36.71, 32.28, 22.62, 22.19, 20.86, 18.14, 16.47, 16.03, 13.86, 13.27.

IR (neat) 3428, 2958, 2926, 2873, 1775, 1769, 1706, 1455, 1368, 1235, 1155, 1078, 1017, 963, 850, 801, 735, 702 $cm^{-1}$.

HRMS (ESI, $[M-H]^-$) calcd for $C_{26}H_{35}O_{10}$ 507.2236, found 507.2235.

Synthesis of Compound 22

Prophetic Example: A method for synthesizing 8-O-debutanoyl-thapsigargin (22) includes the same first seven steps as the synthesis of thapsigargin (1). See FIGS. 3 and 5. The conversion of (R)-(−)-carvone (10) to compound 14, should provide a route to compound (22), which the inventors have postulated.

Step 8. Compound 14 is Oxidized to Form Compound 19.

To a solution of compound 14 (100.0 mg) in acetone (15 ml) is added Jones reagent (4.2 equiv) in two portions (ca. 30 minute interval) at 0° C. The reaction mixture is stirred for ca. 5 hours (t.l.c. control) at the same temperature before being quenched with iPrOH (0.5 ml). The resulting mixture is portioned between sat. aqueous $NaHCO_3$ (100 ml) and EtOAc (50 ml). The organic phases are combined, washed with brine (50 ml), dried over anhydrous $MgSO_4$, filtered and concentrated in vacuo to afford the crude product. Purification by flash column chromatography (silica gel) affords compound 19.

Step 9. Compound 19 Undergoes Oxidation to Form Compound 20.

$Mn(OAc)_3.2H_2O$ (6.0 equiv) is added to a solution of compound 19 (100.0 mg) in octanic acid (6 ml) and benzene (30 ml). The reaction mixture is refluxed for ca. 4 hours while removing water with a Dean-Stark apparatus. The brown reaction mixture is cooled to room temperature and portioned between sat. aqueous $NaHCO_3$ (100 ml) and EtOAc (50 ml). The organic phases are combined, washed with sat. aqueous $NaHCO_3$ (100 ml) five times, dried over anhydrous $MgSO_4$, filtered and concentrated in vacuo to afford the crude product. Purification is performed by flash column chromatography (silica gel) affording compound 20 which may need further recrystallized from $Et_2O$.

Step 10. Compound 20 is Reduced and Acylated to Form Compound 21.

To a solution of compound 20 (10 mg) in $Et_2O$ (2 ml) at −20° C. is added $Zn(BH_4)_2$ (~0.5 M in $Et_2O$, 12.0 equiv) dropwise. After 5 hours, another portion of $Zn(BH_4)_2$ (~0.5 M in $Et_2O$, 12.0 equiv) is added dropwise and the reaction mixture is further stirred for ca. 12 hours. The reaction solution is diluted with EtOAc (20 ml) and sat. aqueous NaEDTA (100 ml). The organic phase is separated and washed with brine (50 ml), dried over anhydrous $Na_2SO_4$, filtered and concentrated in vacuo to afford crude product SI-05. To a mixture of the resulting crude alcohol SI-07, anhydride 17 (10.0 equiv) and $NaHCO_3$ (20.0 equiv) are added PhMe (0.5 ml), then the reaction was stirred for ca. 45 hours at 90° C. After cooling to room temperature, the solution is directly applied to flash column chromatography (silica gel) to afford compound 21.

Step 11. Compound 21 is Deprotected, Followed by Oxidation, Followed by Reduction to Yield 8-O-Debutanoyl-Thapsigargin (22)

To a solution of compound 21 (1.00 g) in EtOAc (42 ml) is added $Pd(OH)_2/C$ (20 wt %, 0.59 g). The suspension is gently evacuated and refilled with $H_2$ and repeated three times. Then the reaction mixture is stirred under $H_2$ (balloon pressure) for 20 minutes before bubbling with argon for 20 minutes. $Pd(OH)_2/C$ catalyst is removed by filtration and solvents are removed in vacuo. A residue is dissolved in DMSO (15 ml) followed by addition of IBX (5.0 equiv). The reaction mixture is stirred at room temperature overnight (~12 hours). After that, MeOH (45 ml) is added and the solution is stirred for 15 minutes before $NaBH_4$ (3.0 equiv) is added at −10° C. After 5 minutes, the reaction mixture is diluted with sat. aqueous $NH_4Cl$ (150 ml) and extracted with EtOAc (100 ml) three times. The combined organic phases are washed with sat. aqueous $NaHCO_3$ (200 ml) twice, dried over anhydrous $MgSO_4$, filtered and concentrated in vacuo to afford the crude product. Purification is performed by flash column chromatography (silica gel) afforded 8-O-debutanoyl-thapsigargin (22).

Example 2. Synthetic Routes to Indicated Compounds of Formula I

Synthesis of Compound DC-21-097: (3S,3aR,4S,6S,6aR,7S,9bS)-6-Acetoxy-4-(butyryloxy)-3,3a-dihydroxy-3,6,9-trimethyl-2,8-dioxo-2,3,3a,4,5,6,6a,7,8,9b-decahydroazuleno[4,5-b]furan-7-yl Hexanoate

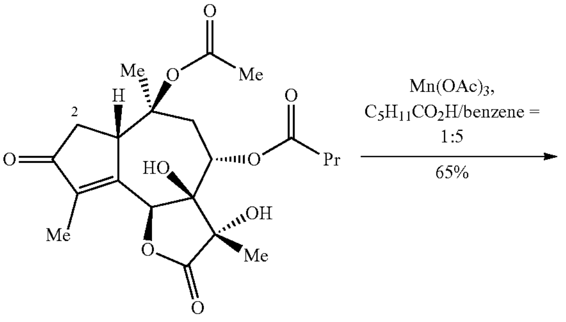

15

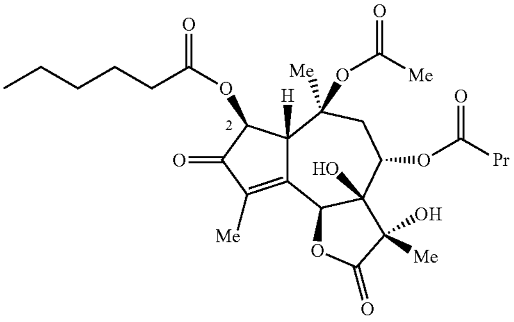

DC-21-097

Compound DC-21-097 was synthesized by following the procedure for synthesis of compound-16

Color and State: white solid $R_f$=0.52 (EtOAc/hexanes=1:1; vanillin)

$^1H$ NMR (400 MHz, $CDCl_3$) δ 5.82 (br. s, 1H), 5.68 (t, J=3.7 Hz, 1H), 5.23-5.21 (m, 1H), 4.54-4.56 (br. s, 1H), 3.87 (br. s, 1H), 3.23 (dd, J=15.2, 2.0 Hz, 1H), 3.03 (br.s, 1H), 2.36-2.20 (m, 5H), 1.99 (br.s, 3H), 1.93 (s, 3H), 1.67-1.57 (m, 4H), 1.46 (s, 3H), 1.37 (s, 3H), 1.32-1.30 (m, 4H), 0.93 (t, J=7.4 Hz, 3H), 0.87 (m, 3H). $^{13}C$ NMR (100 MHz, $CDCl_3$) δ 201.39, 174.72, 172.86, 172.71, 170.98, 156.44, 142.06, 83.95, 78.98, 78.51, 77.83, 66.03, 51.73. 38.64, 36.57, 33.78, 31.11, 24.40, 22.83, 22.49, 22.28, 17.97, 16.05, 13.88, 13.69, 10.24

Synthesis of Thapsigargicin

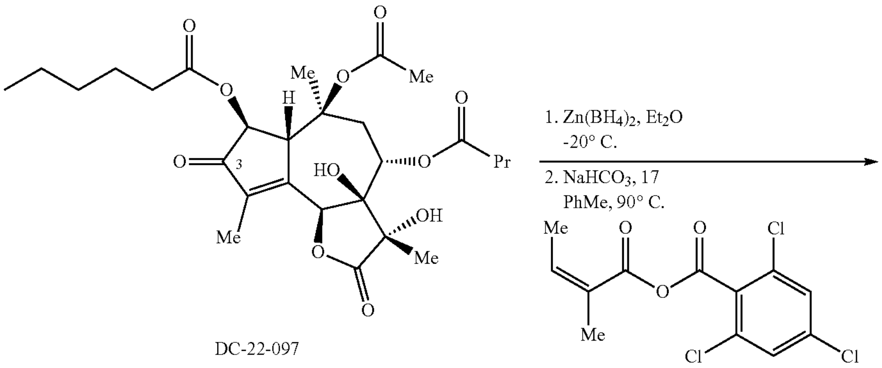

DC-22-097

17

68%

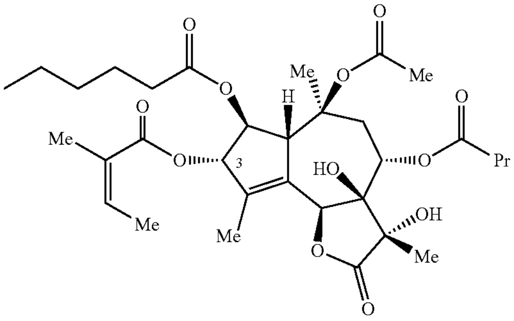

Thapsigargicin

Thapsigargicin was synthesized by following the procedure for synthesis of thapsigargin Color and State: white foam $R_f$=0.5 (EtOAc/hexanes=1:2; vanillin)

$^1$H NMR (600 MHz, $CDCl_3$) δ 6.11 (qq, J=7.2, 1.5 Hz, 1H), 5.68 (br. s, 1H), 5.65 (br. s, 1H), 5.62 (t, J=3.6 Hz, 1H), 5.48 (t, J=3.3 Hz, 1H), 4.24 (s, 1H), 3.02 (s, 1H), 3.00 (dd, J=14.6, 3.1 Hz, 1H), 2.51 (br. s, 1H), 2.36-2.24 (m, 5H), 1.99 (dd, J=7.2, 1.8 Hz, 3H), 1.93-1.91 (m, 3H), 1.89 (br. s, 3H), 1.87 (br. s, 3H), 1.66-1.60 (m, 4H), 1.49 (s, 3H), 1.40 (s, 3H), 1.32-1.29 (m, 4H), 1.20-1.17 (m, 1H), 0.94 (t, J=7.4 Hz, 3H), 0.86 (t, J=6.3 Hz, 3H). $^{13}$C NMR (151 MHz, $CDCl_3$) 175.12, 172.55, 172.51, 170.74, 167.08, 142.12, 138.80, 130.05, 127.52, 84.53, 84.20, 78.69, 77.76, 66.22, 57.72. 38.35, 36.56, 34.24, 31.25, 24.55, 22.89, 22.63, 22.36, 20.63, 18.05, 16.32, 15.86, 13.93, 13.71, 13.00

Synthesis of Compound DC-22-002: (3S,3aR,4S, 6S,6aR,7S,9bS)-6-Acetoxy-4-(butyryloxy)-3,3a-dihydroxy-3,6,9-trimethyl-2,8-dioxo-2,3,3a,4,5,6,6a, 7,8,9b-decahydroazuleno[4,5-b]furan-7-yl 3-methylbutanoate

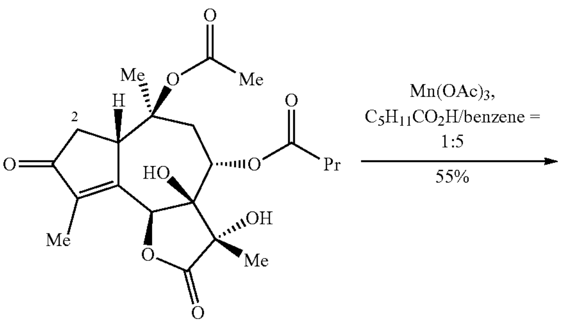

15

-continued
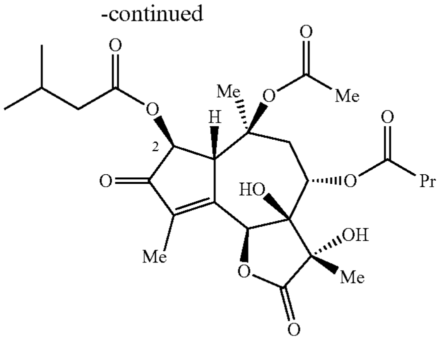
DC-22-002
Compound DC-22-002 was synthesized by following the procedure for synthesis of compound-16
Color and State: white solid
$R_f$=0.52 (EtOAc/hexanes=1:1; vanillin)
$^1$H NMR (400 MHz, $CDCl_3$) δ 5.82 (br. s, 1H), 5.67 (t, J=3.6 Hz, 1H), 5.22 (d, J=3.2 Hz, 1H), 4.54 (br. s, 1H), 3.58 (s, 1H), 3.23 (dd, J=15.2, 3.6 Hz, 1H), 2.81 (s, 1H), 2.30-2.05 (m, 6H), 1.99 (br. s, 3H), 1.93 (s, 3H), 1.65-1.57 (m, 2H), 1.48 (s, 3H), 1.38 (s, 3H), 0.98 (d, J=7.2 Hz, 3H), 0.87 (t, J=7.4 Hz, 3H). $^{13}$C NMR (100 MHz, $CDCl_3$) δ 201.32, 174.50, 172.61, 172.13. 170.88, 156.22, 142.19, 83.85, 79.05, 78.52, 77.77, 72.95, 66.03, 51.81, 42.85, 38.72, 36.55, 25.71, 22.49, 22.41, 22.33, 17.98, 16.15, 13.70, 10.26
Synthesis of Thapsivillosin J
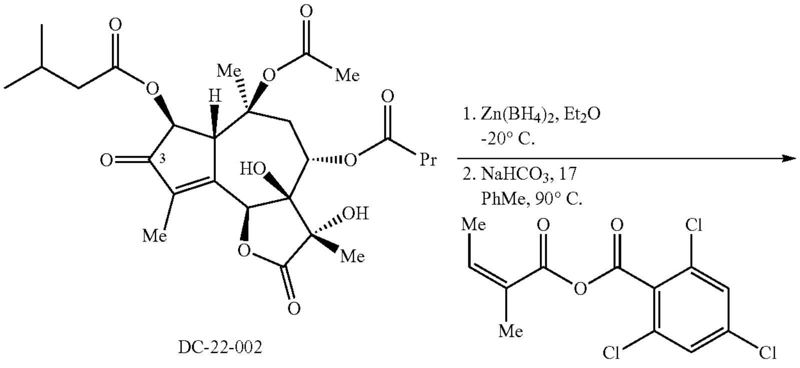
DC-22-002
17
62%
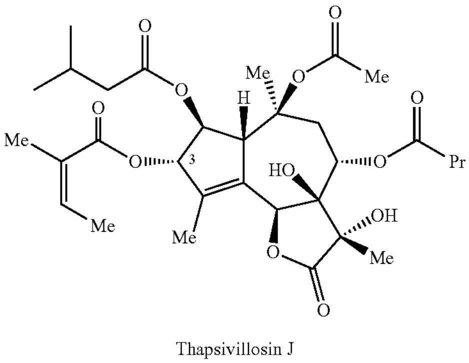
Thapsivillosin J Thapsivillosin J was synthesized by following the procedure for synthesis of thapsigargin (1)

Color and State: white foam $R_f$=0.5 (EtOAc/hexanes=1:2; vanillin)

$^1$H NMR (600 MHz, $CDCl_3$) δ 6.10 (q, J=7.2 Hz, 1H), 5.69 (br. s, 1H), 5.65 (br. s, 1H), 5.62 (t, J=3.9 Hz, 1H), 5.47 (t, J=3.0 Hz, 1H), 4.25 (br. s, 1H), 3.16 (br. s, 1H), 3.01 (dd, J=14.6, 3.1 Hz, 1H), 2.63-2.54 (m, 1H), 2.34-2.30 (m, 1H), 2.28-2.20 (m, 3H), 2.18-2.06 (m, 2H), 1.99 (d, J=7.2, 3H), 1.93-1.88 (m, 5H), 1.86 (br. s, 3H), 1.66-1.58 (m, 3H), 1.48 (s, 3H), 1.40 (s, 3H), 1.25 (s, 3H), 1.21-1.17 (m, 3H), 0.99-0.86 (m, 12H).

Synthesis of Compound DC-22-001: (3S,3aR,4S,6S,6aR,7S,9bS)-6-acetoxy-3,3a-dihydroxy-3,6,9-trimethyl-2,8-dioxo-2,3,3a,4,5,6,6a,7,8,9b-decahydroazuleno[4,5-b]furan-4,7-diyl Dibutyrate

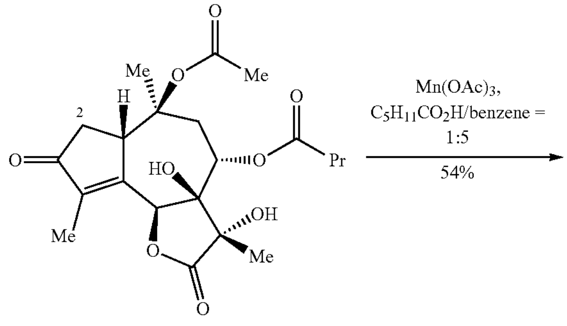

15

-continued

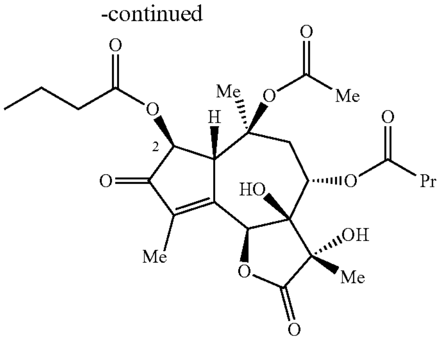

DC-22-001

Compound DC-22-001 was synthesized by following the procedure for synthesis of compound-16

Color and State: white solid $R_f$=0.48 (EtOAc/hexanes=1:1; vanillin)

$^1$H NMR (400 MHz, $CDCl_3$) δ 5.82 (br. s, 1H), 5.67 (t, J=3.6 Hz, 1H), 5.22 (d, J=3.2 Hz, 1H), 4.56 (br. s, 1H), 3.79 (s, 1H), 3.23 (dd, J=14.6, 4.0 Hz, 1H), 2.94 (s, 1H), 2.35-2.20 (m, 5H), 1.99 (br. s, 3H), 1.93 (s, 3H), 1.73-1.58 (m, 4H), 1.47 (s, 3H), 1.38 (s, 3H), 1.00-0.9 (m, 6H). $^{13}$C NMR (100 MHz, $CDCl_3$) δ 201.42, 174.63, 172.68, 170.98, 156.40, 142.11, 83.92, 79.01, 78.53, 77.381, 72.98, 66.04, 51.77, 38.66, 36.58, 35.69, 22.85, 22.49, 18.26, 17.97, 16.09, 13.69, 13.57, 10.24.

Synthesis of Thapsivillosin L

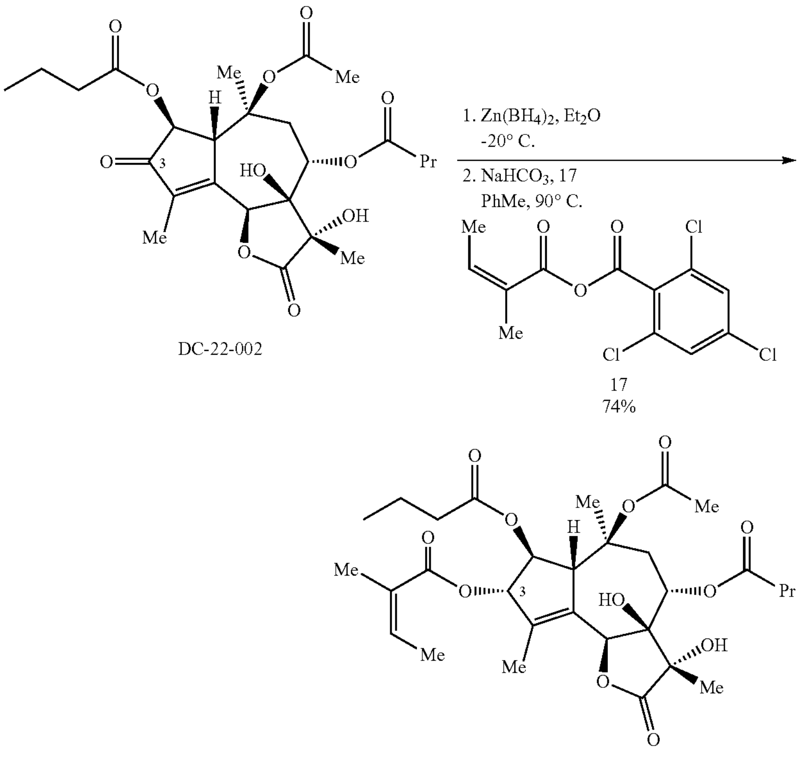

DC-22-002

17

Thapsivillosin L

Thapsivillosin L was synthesized by following the procedure for synthesis of Thapsigargin (1)

Color and State: white foam $R_f$=0.37 (EtOAc/hexanes=1:2; vanillin)

$^1$H NMR (600 MHz, $CDCl_3$) δ 6.11 (qq, J=7.2, 1.5 Hz, 1H), 5.69 (br. s, 1H), 5.65 (br. s, 1H), 5.62 (t, J=3.6 Hz, 1H), 5.49 (t, J=3.3 Hz, 1H), 4.23 (br. s, 1H), 3.02 (s, 1H), 3.00 (dd, J=15.2, 3.3 Hz, 1H), 2.87 (br. s, 1H), 2.41 (br. S, 1H), 2.36-2.24 (m, 5H), 1.99 (dd, J=7.2, 1.8 Hz, 3H), 1.93-1.91 (m, 3H), 1.90 (s, 3H), 1.87 (br. s, 3H), 1.66-1.60 (m, 4H), 1.49 (br. s, 3H), 1.40 (br. s, 3H), 1.25 (br. s, 1H), 1.20-1.17 (m, 2H), 0.99-0.93 (m, 6H). $^{13}$C NMR (151 MHz, $CDCl_3$) δ 175.12, 172.55, 172.51, 170.74, 167.08, 142.12, 138.80, 130.05, 127.52, 84.53, 84.20, 78.69, 77.76, 66.22, 57.72. 38.35, 36.56, 34.24, 31.25, 24.55, 22.89, 22.63, 22.36, 20.63, 18.05, 16.32, 15.86, 13.93, 13.71, 13.00

Synthesis of Compound DC-22-021: (S)-(3S,3aR,4S,6S,6aS,9bS)-6-Acetoxy-3,3a-dihydroxy-3,6,9-trimethyl-2,8-dioxo-2,3,3a,4,5,6,6a,7,8,9b-decahydroazuleno[4,5-b]furan-4-yl 2-methylbutanoate

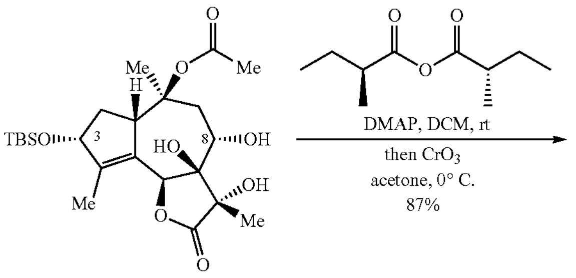

6

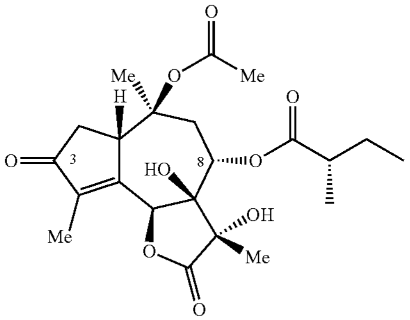

DC-22-021

Compound DC-22-021 was synthesized by following procedure for synthesis of compound-15

Color and State: white foam $R_f$=0.30 (EtOAc/hexanes=1:1; vanillin)

$^1$H NMR (600 MHz, $CDCl_3$) δ 5.78 (s, 1H), 5.70 (t, X of ABX, $J_{AX}$=$J_{BX}$=3.6 Hz, 1H), 4.78-4.75 (m, 1H), 3.54 (s, 1H), 3.32 (dd, A of ABX, $J_{AB}$=14.7 Hz, $J_{AX}$=3.3 Hz, 1H), 2.55 (s, 1H), 2.44 (dd, J=14.7, 3.9 Hz, 1H), 1.98 (s, 3H), 1.95-1.93 (m, 3H), 1.72-1.65 (m, 1H), 1.60 (s, 1H), 1.53 (s, 3H), 1.47-1.40 (m, 1H), 1.21 (s, 3H), 1.13 (d, J=6.6 Hz, 3H), 0.90 (t, J=7.5 Hz, 3H). $^{13}$C NMR (151 MHz, $CDCl_3$) δ 207.00, 175.35, 171.05, 144.97, 85.03, 79.21, 78.67, 77.64, 66.36, 45.99, 41.40, 39.00, 36.59, 26.14, 22.29, 22.21, 16.27, 11.62, 9.75.

Synthesis of Compound DC-22-047: (3S,3aR,4S,6S,6aR,7S,9bS)-6-Acetoxy-3,3a-dihydroxy-3,6,9-trimethyl-4-(((S)-2-methylbutanoyl)oxy)-2,8-dioxo-2,3,3a,4,5,6,6a,7,8,9b-decahydroazuleno[4,5-b]furan-7-yl Octanoate

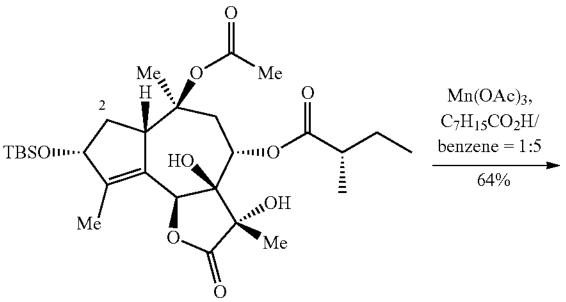

DC-22-021

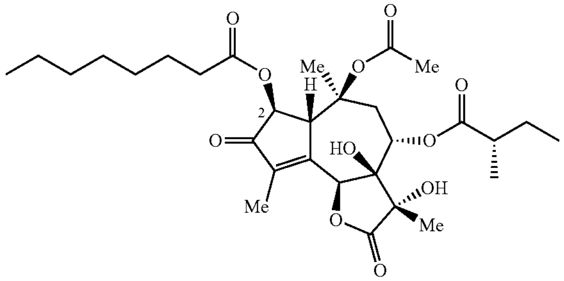

DC-22-047

Compound DC-22-047 was synthesized by following the procedure for synthesis of compound 16

Color and State: white solid $R_f$=0.52 (EtOAc/hexanes=1:1; vanillin)

$^1$H NMR (600 MHz, $CDCl_3$) δ 5.79 (br. s, 1H), 5.66 (t, J=3.6 Hz, 1H), 5.20 (s, 1H), 4.54-4.51 (m, 1H), 3.21 (dd, J=14.4, 3.6 Hz, 1H), 3.02 (s, 1H), 2.44 (s, 1H), 2.37-2.20 (m, 4H), 2.01-1.99 (m, 3H), 1.93 (s, 3H), 1.72-1.58 (m, 10H), 1.51 (s, 3H), 1.48-1.38 (m, 7H), 1.34-1.23 (m, 10H), 1.14 (d, J=7.2 Hz, 3H), 0.90 (t, J=7.2 Hz, 3H), 0.86 (t, J=6.9 Hz, 3H).

Synthesis of Thapsivillosin C

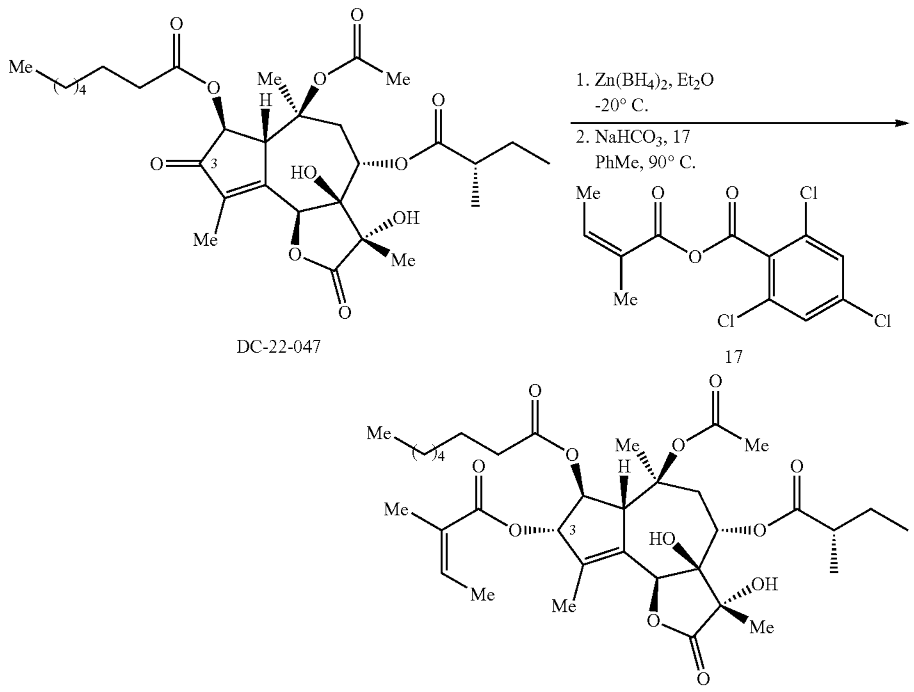

DC-22-047

17

Thapsivillosin C

Thapsivillosin C was synthesized by following the procedure for synthesis of thapsigargin (1).

Color and State: white foam $R_f$=0.37 (EtOAc/hexanes=1:2; vanillin)

$^1H$ NMR (600 MHz, $CDCl_3$): δ=6.11 (qd, J=7.2, J=1.0 Hz, 1H), 5.72 (br. s, 1H), 5.65 (br s, 1H), 5.63 (dd, J=3.7, J=3.6 Hz, 1H; H-8), 5.50 (t, J=3.2 Hz, 1H), 4.23 (br s, 1H), 2.99 (dd, J=14.8, J=3.3 Hz, 1H), 2.37-2.25 (m, 4H), 2.01 (dd, J=7.2, J=1.2 Hz, 3H), 1.93 (s, 3H), 1.91 (s, 3H), 1.89 (s, 3H), 1.72 (m, 1H), 1.62 (m, 2H), 1.52 (s, 3H), 1.44 (m, 1H), 1.42 (s, 3H), 1.35-1.25 (m, 8H), 1.85 (d, J=7.4 Hz, 3H), 0.92 (m, 3H), 0.88 (m, 3H).

Synthesis of Compound DC-21-100: (3S,3aR,4S,6S,6aS,8R,9bS)-6-Acetoxy-3,3a,8-trihydroxy-3,6,9-trimethyl-2-oxo-2,3,3a,4,5,6,6a,7,8,9b-decahydroazuleno[4,5-b]furan-4-yl 3-methylbut-2-enoate

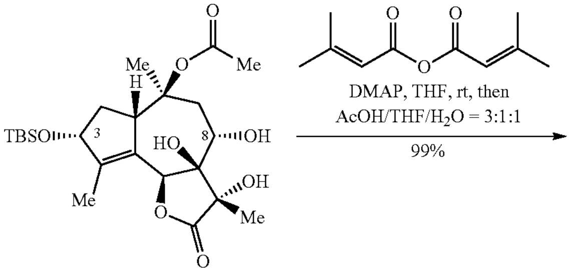

6

-continued

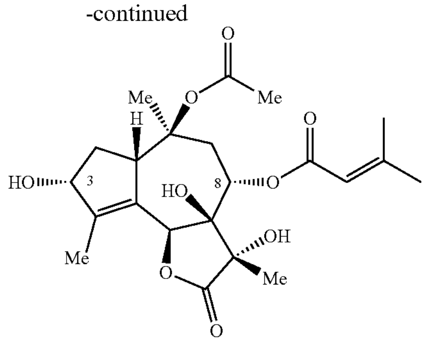

DC-22-100

Compound DC-21-100 was synthesized by following procedure for synthesis of compound-18

$R_f$=0.20 (EtOAc/hexanes=1:1; vanillin)

$^1H$ NMR (600 MHz, $CDCl_3$) δ 5.70 (br. s, 1H), 5.61 (s, 1H), 5.58 (t, J=3.6 Hz, 1H), 4.56 (m, 1H), 4.24 (m, 1H), 3.27 (s, 1H), 3.12 (dd, J=14.6 Hz, J=3.0 Hz, 1H), 2.55 (s, 1H), 2.35 (dt, J=14.0, 8.2 Hz, 1H), 2.22-2.13 (m, 4H), 1.96 (s, 3H), 1.93 (br. s, 3H), 1.90 (s, 3H), 1.61-1.53 (m, 1H), 1.48 (s, 3H), 1.31 (s, 3H). $^{13}C$ NMR (100 MHz, $CDCl_3$) δ 175.63, 171.17, 165.36, 159.73, 146.48, 129.04, 115.53, 86.20, 79.06, 78.99, 78.12, 76.83, 66.47, 50.08, 38.60, 34.71, 27.68, 22.55, 20.60, 16.51, 12.87.

Synthesis of Thapsivillosin F

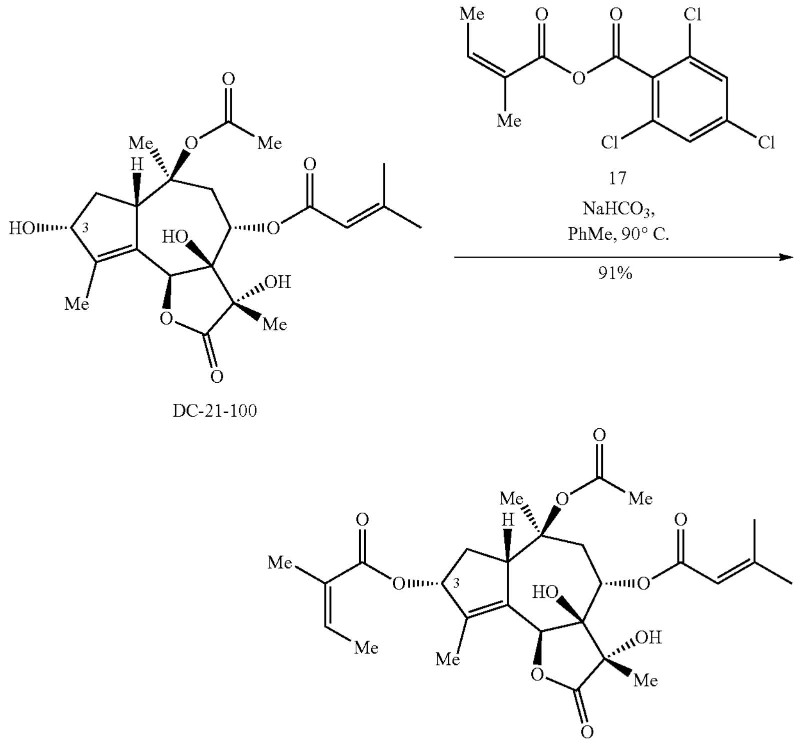

17

DC-21-100 thapsivillosin F

Thapsivillosin F was synthesized by following the procedure for synthesis of nortrilobolide $R_f$=0.50 (EtOAc/hexanes=1:1; vanillin)

$^1$H NMR (600 MHz, $CDCl_3$) δ 6.11 (qq, J=7.3, 1.5 Hz, 1H), 5.72 (br. s, 1H), 5.62 (s, 1H), 5.60 (t, J=3.6 Hz, 1H), 4.37-4.30 (m, 1H), 3.08 (dd, J=14.7 Hz, J=3.3 Hz, 1H), 2.97 (s, 1H), 2.54 (dt, J=14.4, 8.7 Hz, 1H), 2.35 (s, 1H), 2.24 (dd, J=14.4 Hz, J=4.2 Hz, 1H), 1.96 (s, 3H), 1.91-1.89 (m, 9H), 1.66 (dt, J=15.0, 4.8 Hz, 1H), 1.50 (s, 3H), 1.31 (s, 3H), 0.94 (t, J=7.4 Hz, 3H). $^{13}$C NMR (151 MHz, $CDCl_3$) δ 175.35, 171.00, 167.83, 165.34, 159.81, 143.58, 138.55, 131.41, 127.96, 115.49, 87.92, 79.80, 79.06, 79.00, 77.70, 66.49, 50.97, 38.53, 32.27, 27.66, 22.60, 22.20, 20.83, 20.61, 16.59, 15.99, 13.21.

Synthesis of Compound DC-22-20: (S)-(3S,3aR,4S,6S,6aS,8R,9bS)-6-Acetoxy-3,3a,8-trihydroxy-3,6,9-trimethyl-2-oxo-2,3,3a,4,5,6,6a,7,8,9b-decahydroazuleno[4,5-b]furan-4-yl 2-methylbutanoate

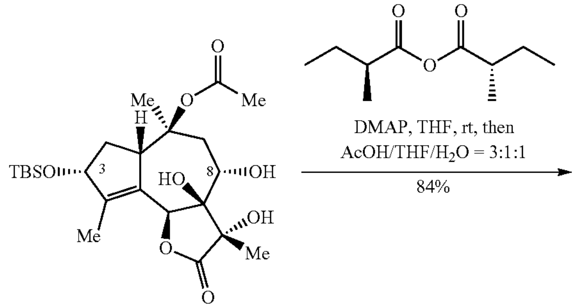

6

-continued

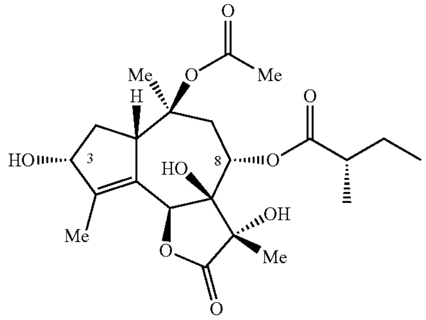

DC-22-20

Compound DC-22-20 was synthesized by following procedure for synthesis of compound-18

$R_f$=0.19 (EtOAc/hexanes=1:1; vanillin)

$^1$H NMR (600 MHz, $CDCl_3$) δ 5.66 (br. s, 1H), 5.62 (t, J=3.6 Hz, 1H), 4.58 (m, 1H), 4.26 (m, 1H), 3.75-3.45 (m, 2H), 3.25-3.15 (m, 2H), 2.61 (s, 1H), 2.38-2.31 (m, 2H), 2.10 (dd, J=14.7 Hz, J=3.9 Hz, 1H), 1.96-1.93 (m, 9H), 1.72-1.66 (m, 4H), 1.64-1.55 (m, 2H), 1.50-1.35 (m, 8H), 1.14-1.11 (m, 3H), 0.95-0.86 (m, 3H). $^{13}$C NMR (100 MHz, $CDCl_3$) δ 175.88, 175.62, 171.18, 146.60, 129.14, 86.19, 78.92, 78.10, 77.77, 72.61, 71.42, 70.64, 70.32, 66.72, 62.02, 50.08, 41.59, 38.80, 34.64, 31.78, 29.84, 26.28, 22.75, 22.53, 16.41, 16.32, 12.92, 11.77.

Synthesis of Trilobolide

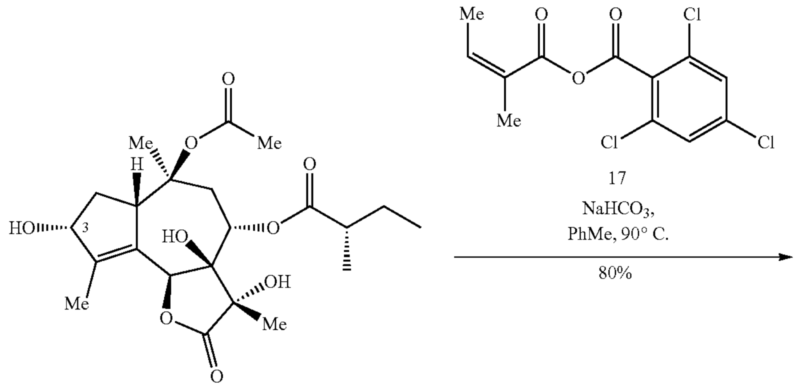

DC-22-20

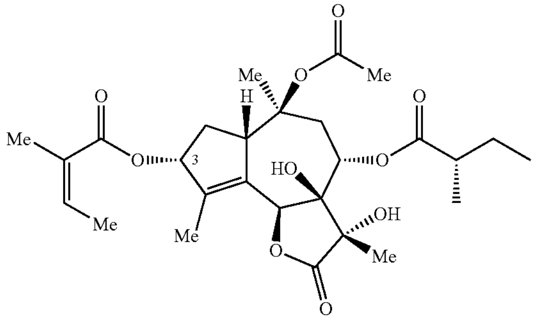

Ttrilobolide

Trilobolide was synthesized by following the procedure for synthesis of nortrilobolide.

$R_f$=0.27 (EtOAc/hexanes=1:1; vanillin)

$^1$H NMR (600 MHz, $CDCl_3$) δ 6.11 (qq, J=7.3, 1.5 Hz, 1H), 5.68 (br. s, 1H), 5.63 (t, J=3.6 Hz, 1H), 5.59 (m, 1H), 4.37-4.34 (m, 1H), 3.11 (dd, J=15.0 Hz, J=3.0 Hz, 1H), 2.84 (br. s, 1H), 2.57 (dt, J=14.8, 8.5 Hz, 1H), 2.36-2.30 (m, 2H), 2.20-2.17 (m, 1H), 2.01 (dd, J=7.2, 1.6 Hz, 3H), 1.97 (s, 3H), 1.92-1.89 (m, 6H), 1.73-1.63 (m, 3H), 1.57 (s, 3H), 1.50 (s, 3H), 1.48-1.42 (m, 1H), 1.32 (s, 3H), 1.14 (d, J=7.2 Hz, 3H), 0.90 (t, J=7.5 Hz, 3H). $^{13}$C NMR (151 MHz, $CDCl_3$) 175.46, 175.23, 170.80, 167.82, 144.11, 138.61, 131.07, 127.94, 85.62, 79.67, 78.98, 78.85, 77.63, 66.71, 51.15, 41.57, 38.75, 32.35, 26.33, 22.58, 22.30, 20.83, 16.56, 16.43, 16.00, 13.27, 11.79.

Example 3. Synthetic Routes to Compound of Formula IB

Synthesis of Compound DC-18-037: (2S,4S)-methyl 4-(Benzyloxy)-6-((1R,4R)-4-((tert-butyldimethylsilyl)oxy)-2-formyl-3-methylcyclopent-2-en-1-yl)-2-methyl-3-oxo-2-((trimethylsilyl)oxy)hept-6-enoate

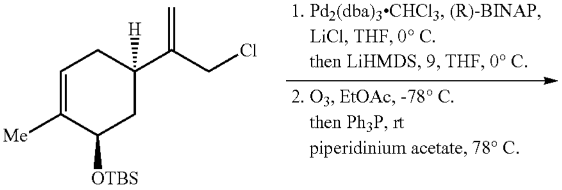

11

-continued

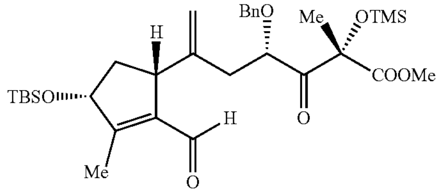

DC-18-037

Compound DC-18-037 was synthesized by following procedures from compound 11 to 13 Color and State: colorless oil $R_f$=0.46 (EtOAc/hexanes=1:4; vanillin)

$^1$H NMR (400 MHz, $CDCl_3$) δ 9.91 (s, 1H), 7.357-7.25 (m, 5H), 4.92 (s, 1H), 4.87 (s, 1H), 4.83 (dd, X of ABX, $J_{AX}$=8.8 Hz, $J_{BX}$=3.0 Hz, 1H), 4.55 (app. t, J=7.0 Hz, 1H), 4.49 (dd, X of ABX, $J_{AX}$=15.2 Hz, $J_{BX}$=11.2 Hz, 2H), 4.23-4.09 (m, 2H), 3.40 (app. t, J=7.2 Hz, 1H), 2.66 (dd, B of ABX, $J_{AB}$=15.2 Hz, $J_{BX}$=2.5 Hz, 1H), 2.50 (dt, A of ABXY, $J_{AB}$=13.2 Hz, $J_{AX}$=$J_{AY}$=7.6 Hz, 1H), 2.29 (dd, A of ABX, $J_{AB}$=15.2 Hz, $J_{AX}$=10.4 Hz, 1H), 2.13 (s, 3H), 1.54 (s, 3H), 1.54-1.45 (m, 1H), 0.92 (s, 9H), 0.18 (s, 9H), 0.11 (s, 3H), 0.08 (s, 3H).

Synthesis of Compound DC-22-042: (3S,3aS,4S,6aR,8R,9bR)-4-(Benzyloxy)-8-((tert-butyldimethylsilyl)oxy)-3a-hydroxy-3,9-dimethyl-6-methylene-3-((trimethylsilyl)oxy)-3,3a,4,5,6,6a,7,8-octahydroazuleno[4,5-b]furan-2(9bH)-one

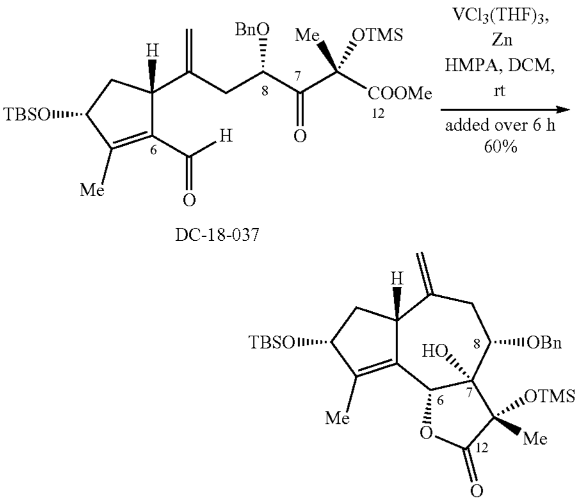

DC-18-037

DC-22-042

$R_f$=0.31 (EtOAc/hexanes=1:10; vanillin)

$^1$H NMR (600 MHz, $CDCl_3$) δ 7.39-7.32 (m, 5H), 5.04 (br. s, 1H), 4.94 (s, 1H), 4.74 (s, 1H), 4.43-4.40 (m, 3H), 3.96 (br. s, 1H), 3.34 (br. s, 1H), 2.81 (d, J=14.4 Hz, 1H), 2.69-2.62 (m, 1H), 2.48-2.40 (m, 1H), 1.75 (s, 3H), 1.47-1.41 (m, 4H), 0.86 (s, 9H), 0.23 (s, 9H), 0.04 (s, 3H), 0.03 (s, 3H).

In a prophetic synthetic route, it is postulated that thapsitranstagin, 2-acetoxytrilobolide and thapsivillosin B, D, G and K can be synthesized from a common starting material DC-22-021 in three steps (procedures according to compound-16 to thapsigargin).

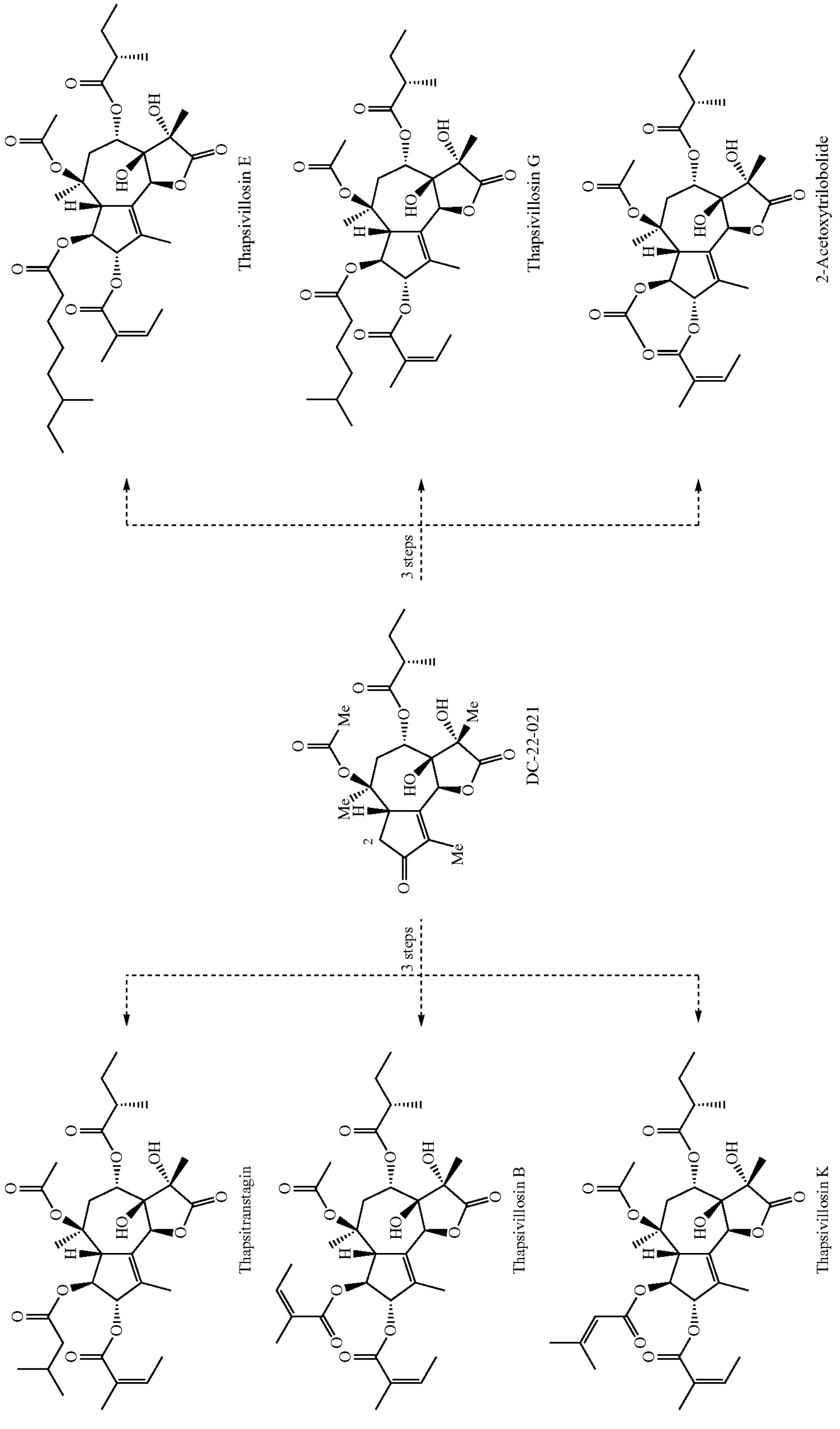
DC-22-021
Thapsitranstagin
Thapsivillosin B
Thapsivillosin K
Thapsivillosin E
Thapsivillosin G
2-Acetoxytrilobolide Similarly, in a prophetic route, thapsivillosin I is synthesized from common starting material 16 in three steps similar for thapsigargin synthesis.

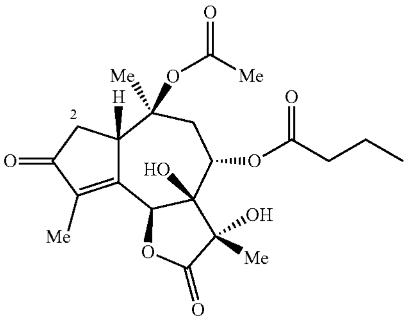

16

3 steps

-continued

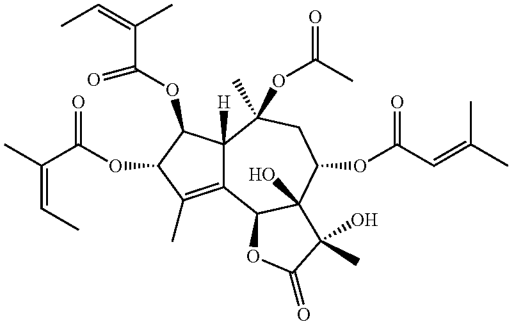

Thapsivillosin I

In a prophetic synthetic route to thapsivillosin A, D, and H, it is postulated that these compounds can be synthesized from a common starting material DC-21-100 in four steps (first step is $CrO_3$ oxidation followed by procedures to synthesize thapsigargin from 16.

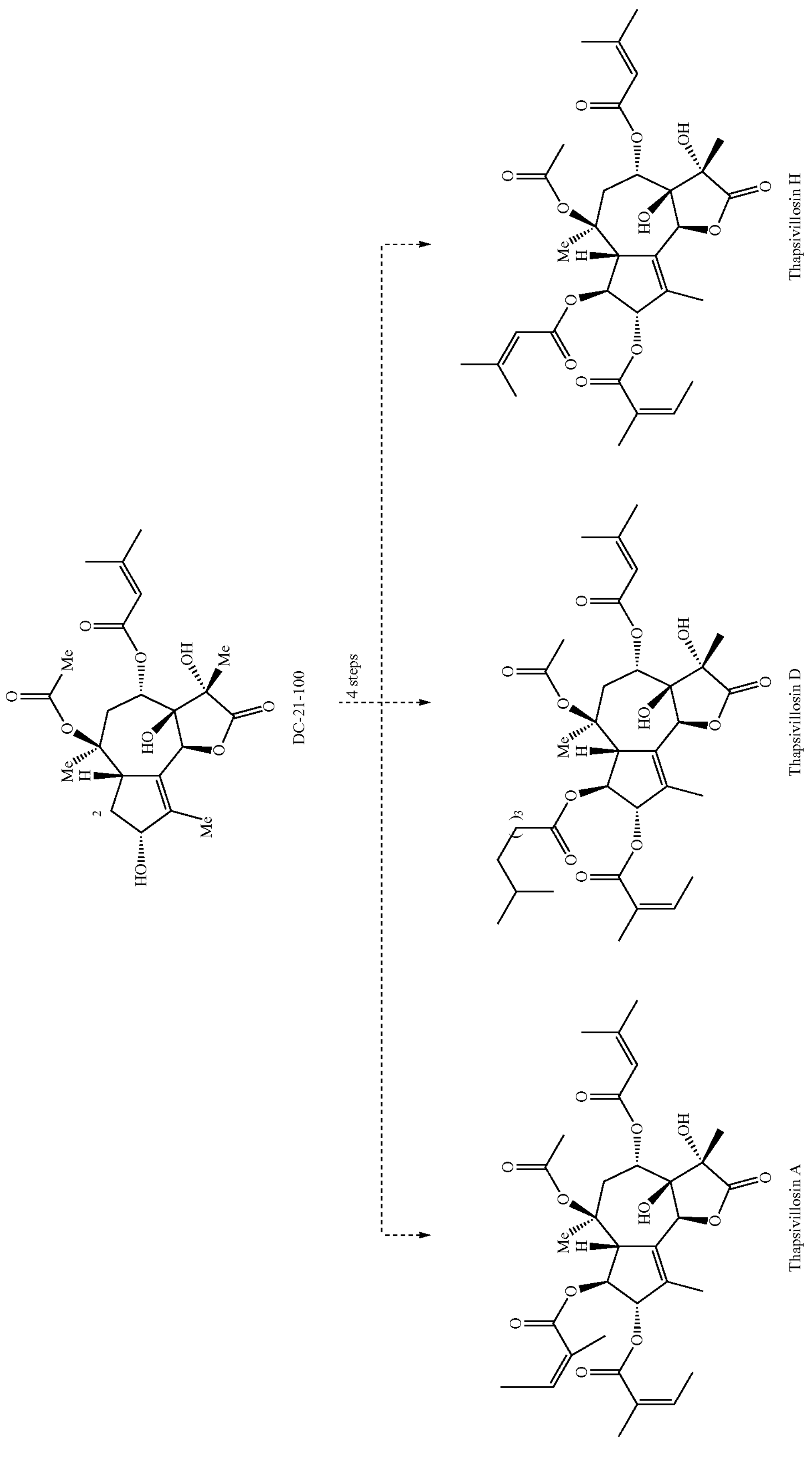
DC-21-100
Thapsivillosin A
Thapsivillosin D
Thapsivillosin H

It will be understood by those skilled in the art that this description is made with reference to certain embodiments and that it is possible to make other embodiments employing the principles of the invention which fall within its scope as defined by the claims.

We claim:

1. A method for synthesizing a compound of Formula I or a pharmaceutically acceptable salt thereof, wherein Formula I is:

I

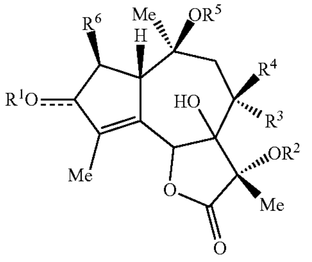

wherein $R^1$ is H, acyl, aryl, or aliphatic group, or may not be present;

$R^2$ is H, acyl, aryl, aliphatic, or a hydroxyl protecting group;

$R^3$ and $R^4$ are independently H or acyloxy, alkoxyl, or OP wherein P is a hydroxyl protecting group;

$R^5$ is H or an acyl or aliphatic group;

$R^6$ is H or an acyloxy or alkoxy group:

carbon moieties within acyl, acyloxy, alkyl and alkoxy groups are aliphatic or aryl and may be substituted or unsubstituted; and a dotted line represents a bond that may or may not be present, the method comprising subjecting a reactant to a series of chemical reactions that produce synthetic intermediates including an alkylation to produce compound 12

12

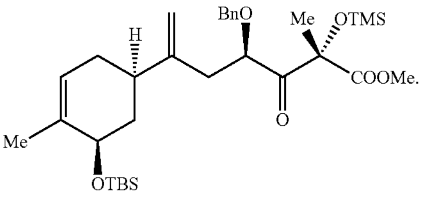

2. The method of claim 1, wherein the compound of Formula I is a compound of Formula IA or Formula IB:

Formula IA

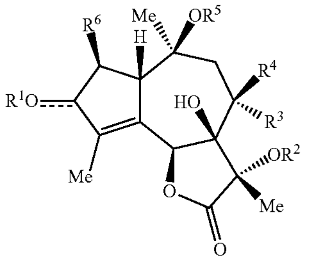

-continued

Formula IB

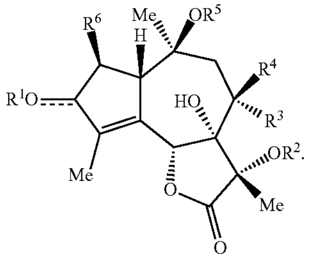

3. The method of claim 2, wherein the compound of Formula IA is:

thapsigargin, thapsigargicin, thapsitranstagin, 2-acetoxytrilobolide, thapsivillosin A, thapsivillosin B, thapsivillosin C, thapsivillosin D, thapsivillosin E, thapsivillosin H, thapsivillosin G, thapsivillosin I, thapsivillosin J, thapsivillosin K, thapsivillosin L, thapsivillosin F, trilobolide, or nortrilobolide

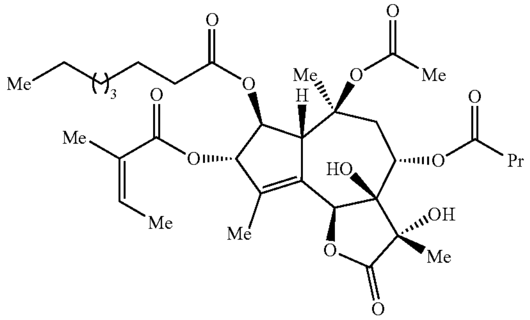

Thapsigargin

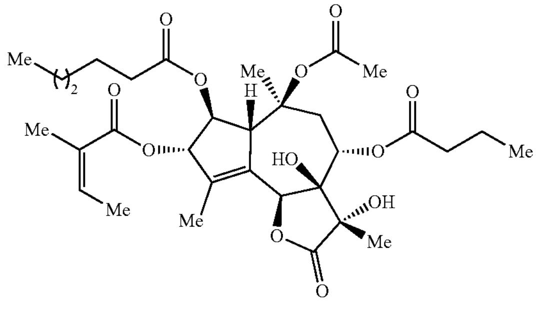

Thapsigargicin

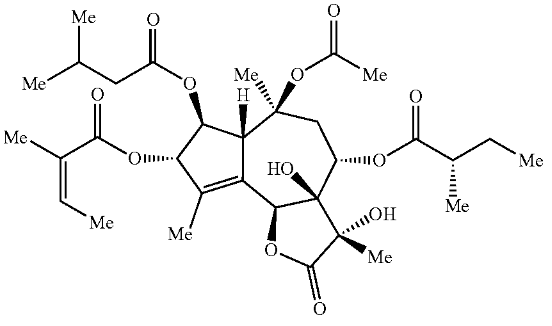

Thapsitranstagin

-continued
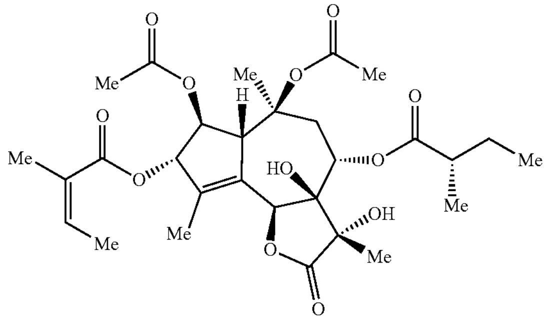
2-Acetoxytrilobolide
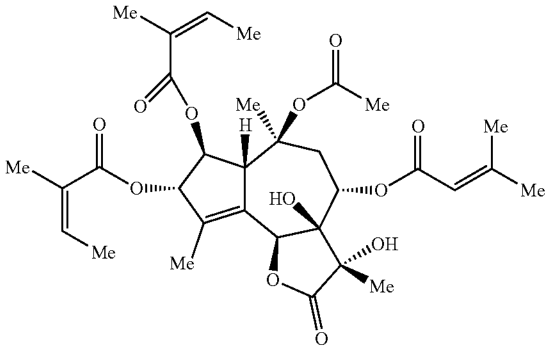
Thapsivillosin A
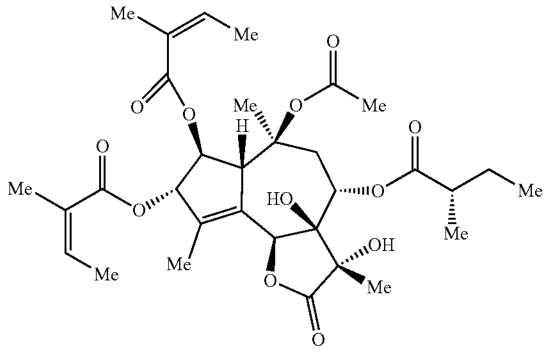
Thapsivillosin B
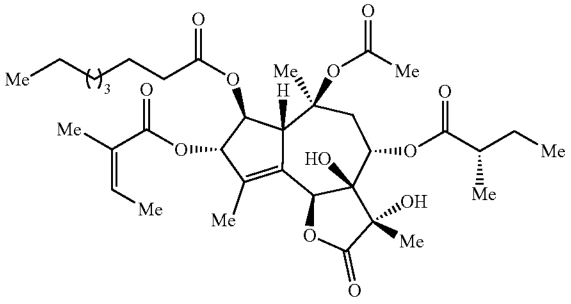
Thapsivilliosin C
-continued
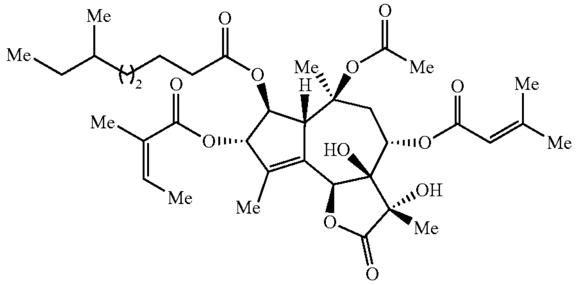
Thapsivilliosin D
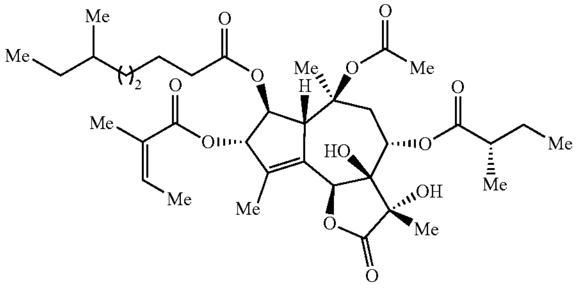
Thapsivilliosin E
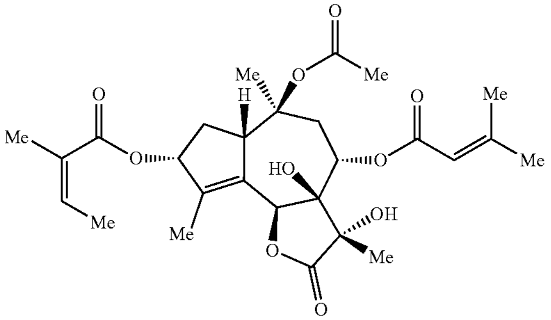
Thapsivillosin F
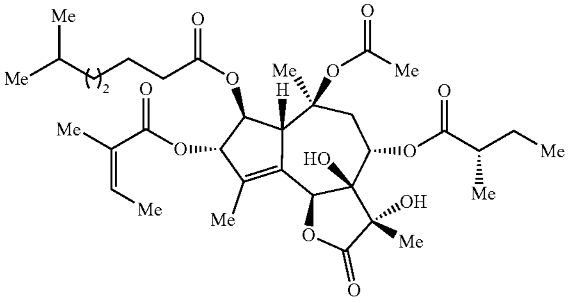
Thapsivillosin G -continued
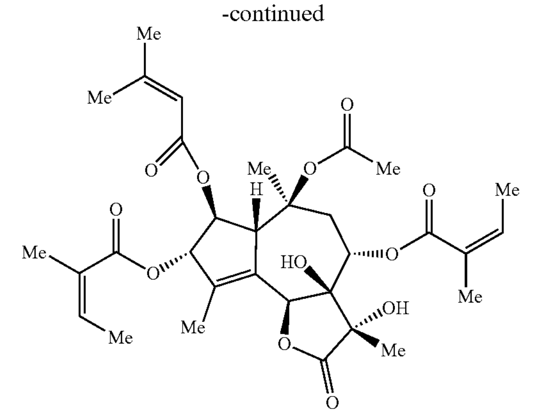
Thapsivillosin H
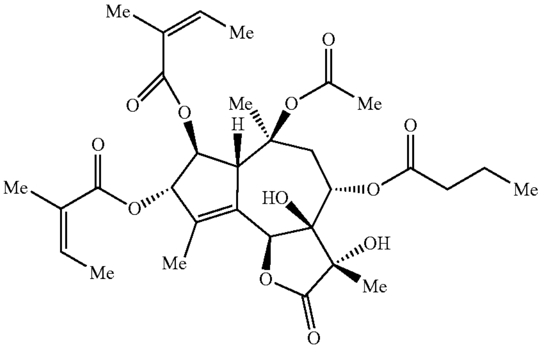
Thapsivillosin I
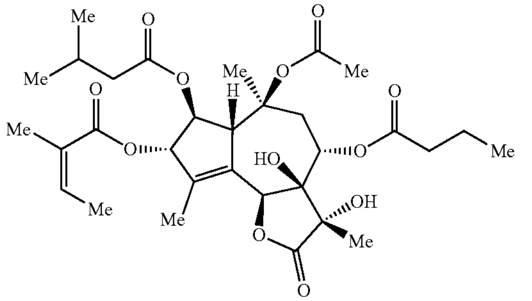
Thapsivillosin J
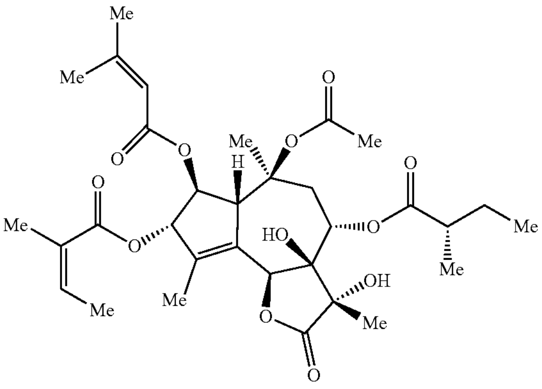
Thapsivillosin K
-continued
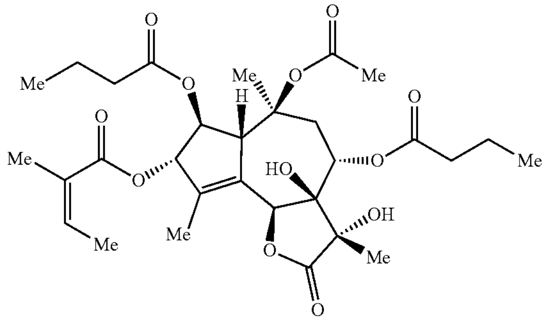
Thapsivillosin L
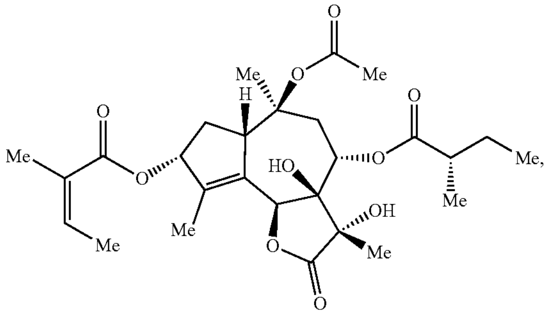
Me, or
Trilobolide
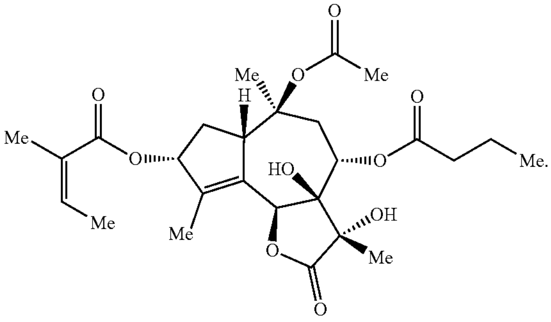
Me.
Nortrilobolide
4. The method of claim 2, wherein the compound of Formula IB is compound DC-22-042
DC-22-042
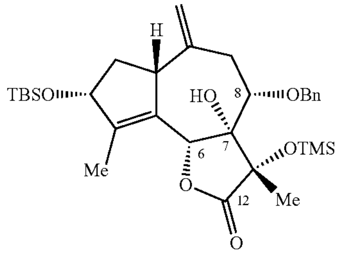
(3S,3aS,4S,6aR,8R,9bR)-4-(Benzyloxy)-8-((tert-butyldimethylsilyl)oxy)-3a-hydroxy-3,9-dimethyl-6-methylene-3-((trimethylsilyl)oxy)-3,3a,4,5,6,6a,7,8-octahydroazuleno[4,5-b]furan-2(9bH)-one.

5. The method of claim 1, wherein the compound of Formula I is thapsigargin (1)

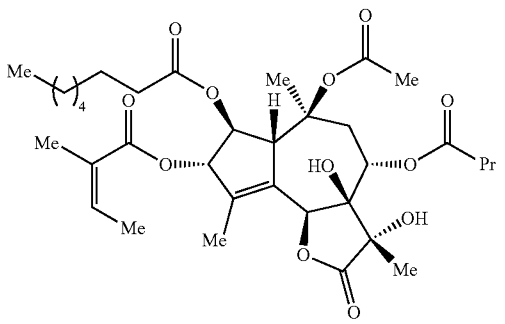

thapsigargin (1)

or a pharmaceutically acceptable salt thereof.

6. The method of claim 1, wherein the reactant is (R)-(−)-carvone (10).

7. The method of claim 1, further comprising reacting a reactant in a series of chemical reactions that produce synthetic intermediates that include compound 7

7

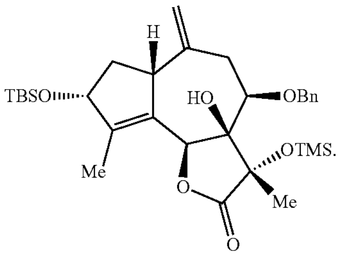

8. The method of claim 1, further comprising reacting a reactant in a series of chemical reactions that produce synthetic intermediates that include compound 8

8

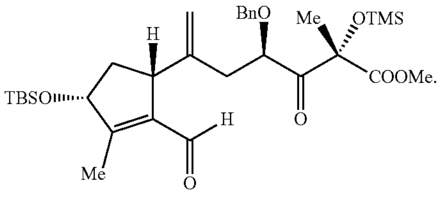

9. The method of claim 1, further comprising reacting a reactant in a series of chemical reactions that produce synthetic intermediates that include compound 13

13

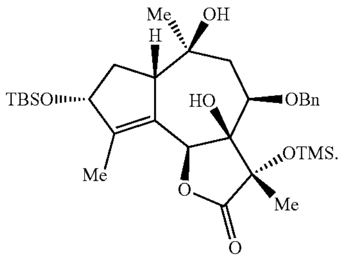

10. The method of claim 1, further comprising reacting a reactant in a series of chemical reactions that produce synthetic intermediates that include compound 14

14

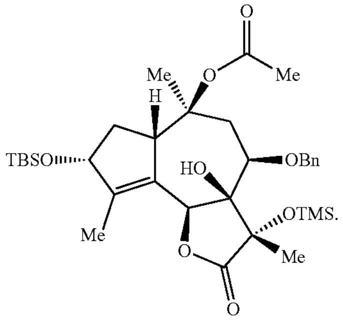

11. The method of claim 1, further comprising reacting a reactant in a series of chemical reactions that produce synthetic intermediates that include compound 15

15

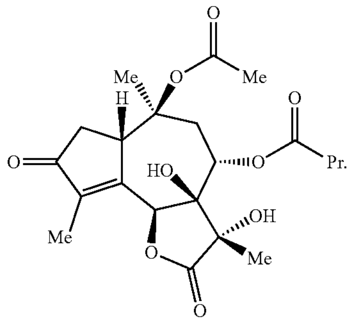

12. The method of claim 1, further comprising reacting a reactant in a series of chemical reactions that produce synthetic intermediates that include compound 16

16

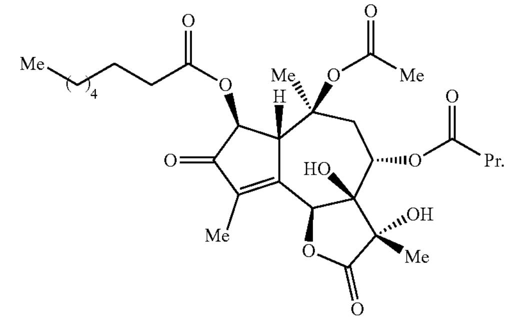

13. The method of claim 1, further comprising reacting a reactant in a series of chemical reactions that produce synthetic intermediates that include compound SI-04

SI-04

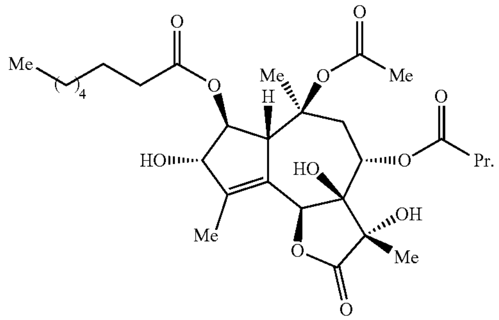

14. The method of claim 1 wherein the compound of Formula I is thapsigargin (1) or a pharmaceutically acceptable salt thereof, comprising the steps of:

Step 1) converting of (R)-(−)-carvone (10) to compound SI-01 by allylic halogenation;

Step 2) converting compound SI-01 to compound 11 by reduction and in situ protection;

Step 3) coupling compound 11 and compound 9 to form compound 12 by asymmetric alkylation;

Step 4) converting compound 12 to compound 8 by selective ozonolysis followed by in situ aldol condensation and dehydration;

Step 5) converting compound 8 to compound 7 by pinacol coupling and in situ lactonization;

Step 6) converting compound 7 to compound 13 by hydration;

Step 7) converting compound 13 to compound 14 by acylation;

Step 8) converting compound 14 to compound 6 by deprotection, oxidation, and reduction;

Step 9) converting compound 6 to compound 15 by acylation and oxidation;

Step 10) converting compound 15 to compound 16 by oxidation;

Step 11) converting compound 16 to compound SI-04 by reduction; and Step 12) converting compound SI-04 to thapsigargin (1) by acylation

SI-01

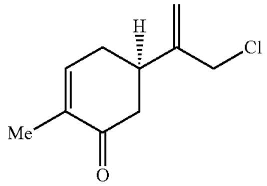

6

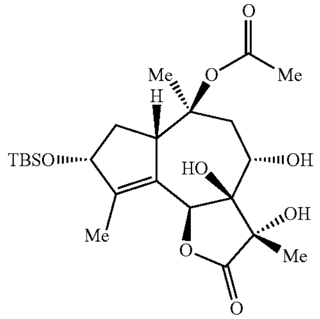

7

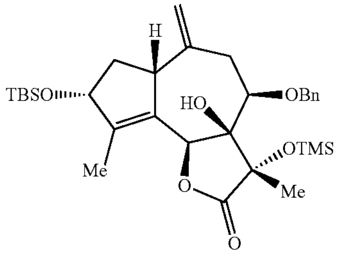

8

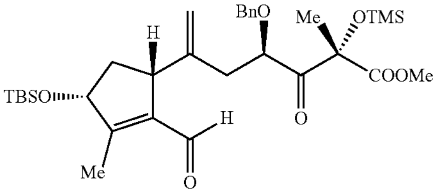

9

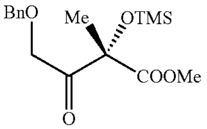

10

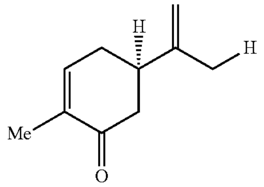

11

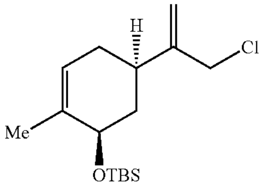

-continued

12

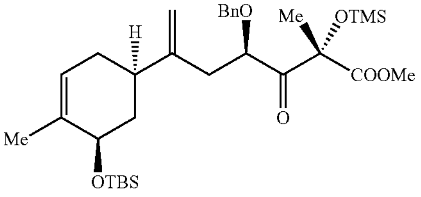

13

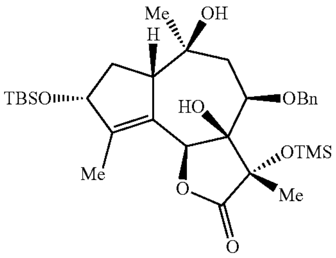

14

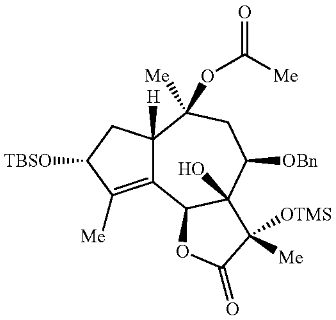

15

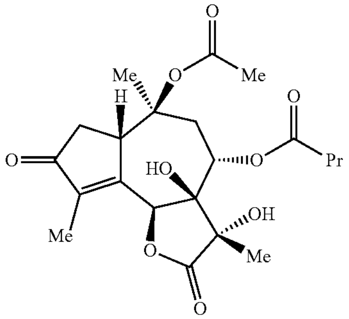

16

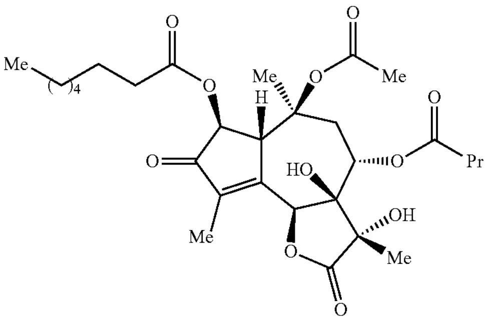

-continued

SI-04

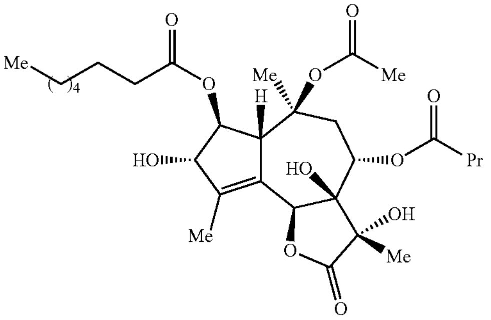

(1)

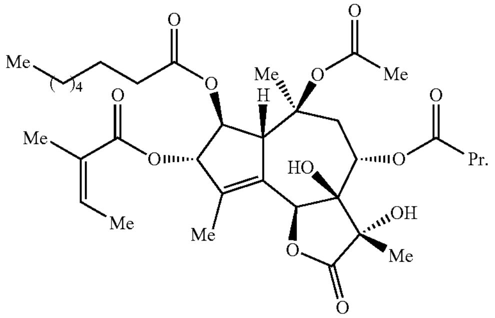

Thapsigargin

15. The method of claim 1 wherein the compound of Formula I is nortrilobolide (3) or a pharmaceutically acceptable salt thereof, comprising the steps of:

Step 1) converting (R)-(−)-carvone (10) to compound SI-01 by allylic halogenation;

Step 2) converting compound SI-01 to compound 11 by reduction and in situ protection;

Step 3) coupling compound 11 and compound 9 to form compound 12 by asymmetric alkylation;

Step 4) converting compound 12 to compound 8 by selective ozonolysis followed by in situ aldol condensation and dehydration;

Step 5) converting compound 8 to compound 7 by pinacol coupling and in situ lactonization;

Step 6) converting compound 7 to compound 13 by hydration;

Step 7) converting compound 13 to compound 14 by acylation;

Step 8) converting compound 14 to compound 6 by deprotection, oxidation, and reduction;

Step 9) converting compound 6 to compound 18 by acylation, and deprotection; and Step 10) converting compound 18 to nortrilobolide (3) by acylation 6
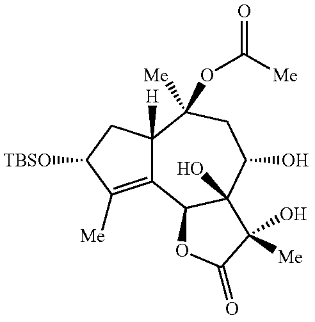
7
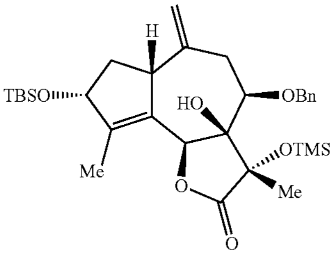
8
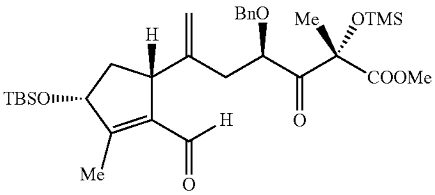
9
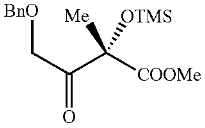
10
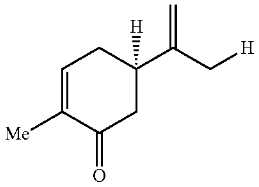
11
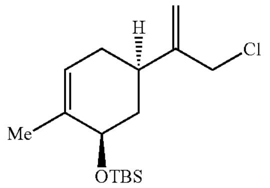
12
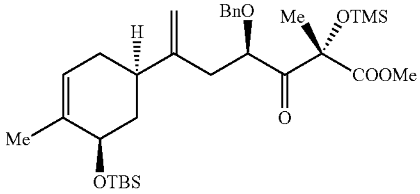
-continued
13
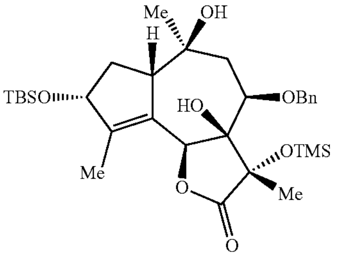
14
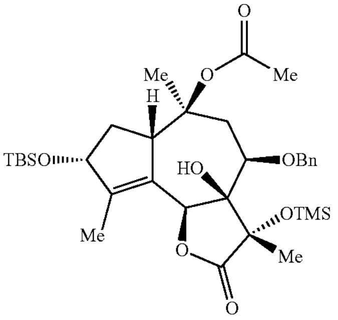
18
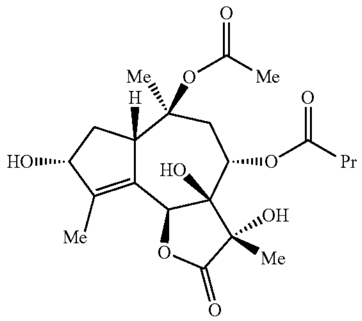
SI-01
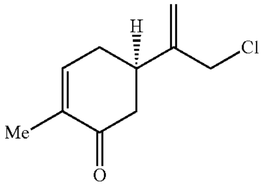
(3)
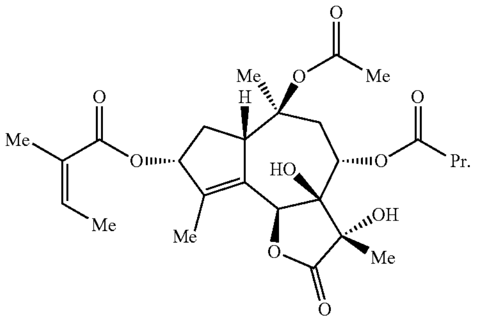
Nortrilobolide
16. The method of claim 1 wherein the compound of Formula I is compound 9 or a pharmaceutically acceptable salt thereof, comprising the steps of:
converting compound SI-02 to compound SI-03 by dihydroxylation; and
converting compound SI-03 to compound 9 by oxidation and in situ protection

SI-02

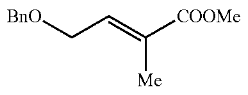

SI-03

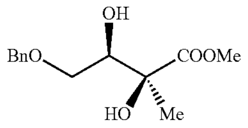

9

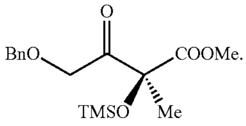

17. The method of claim 1 wherein the compound of Formula I is compound 18 or a pharmaceutically acceptable salt thereof, comprising the step of selective acylation and deprotection of compound 6

6

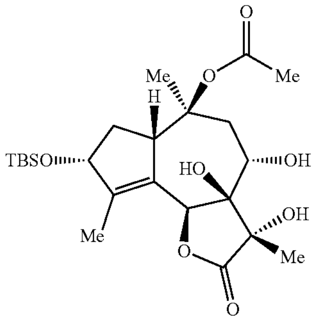

18

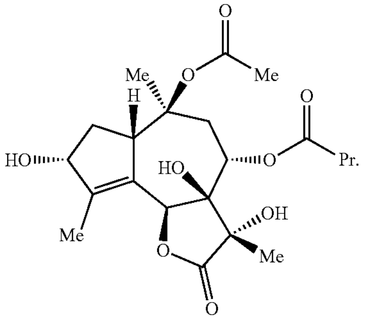

18. The method of claim 1 wherein the compound of Formula I is compound 15 or a pharmaceutically acceptable salt thereof, comprising the step of selective acylation and oxidation of compound 6

6

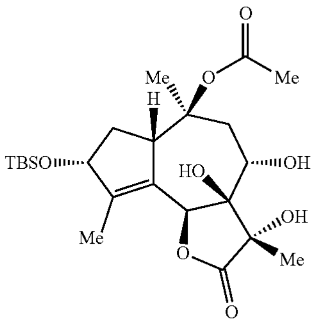

15

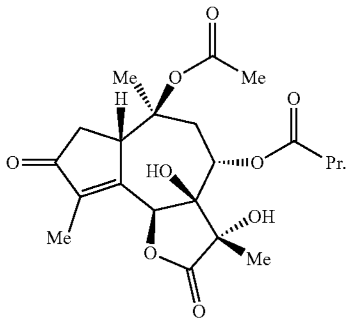

19. The method of claim 1 wherein the compound of Formula I is compound 6 or a pharmaceutically acceptable salt thereof, comprising the step of inverting stereochemistry of compound 14 at C-8

6

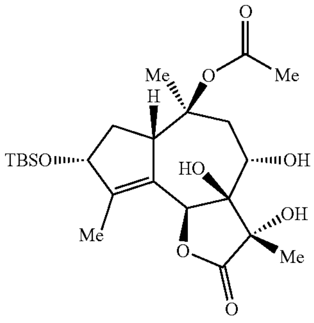

14

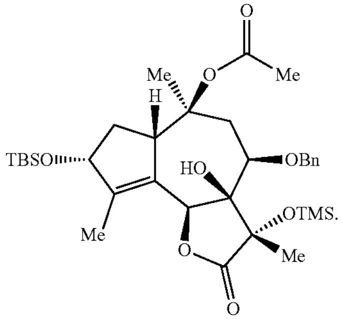

20. The method of claim 1 wherein the compound of Formula I is compound 13 or a pharmaceutically acceptable salt thereof, comprising the step of stereoselective installation of oxygen functionality at C-10 position of compound 7

7

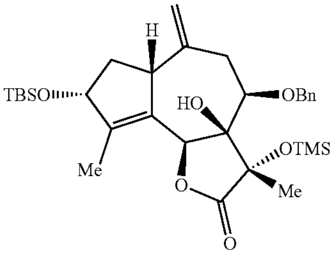

13

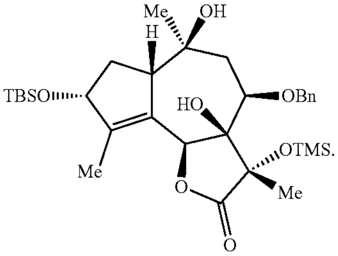

21. The method of claim 1 wherein the compound of Formula I is compound 7 or a pharmaceutically acceptable salt thereof, comprising the step of pinacol coupling of compound 8 and in situ lactonization

8

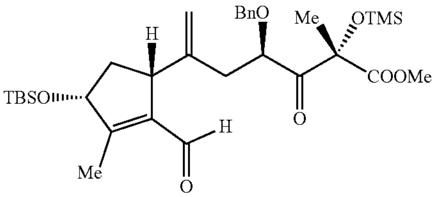

7

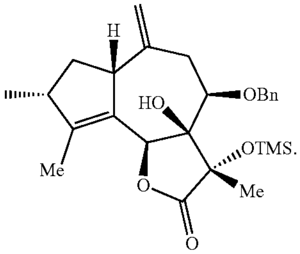

22. The method of claim 1 wherein the compound of Formula I is 8-O-debutanoyl-thapsigargin (22) or a pharmaceutically acceptable salt thereof, comprising the steps of Step C1) converting of (R)-(−)-carvone (10) to compound SI-01 by chlorination;

Step C2) converting compound SI-01 to compound 11 by reduction and in situ protection;

Step C3) coupling compound 11 and compound 9 to form compound 12 by asymmetric alkylation;

Step C4) converting compound 12 to compound 8 by selective ozonolysis followed by in situ aldol condensation and dehydration;

Step C5) converting compound 8 to compound 7 by pinacol coupling and in situ lactonization;

Step C6) converting compound 7 to compound 13 by hydration;

Step C7) converting compound 13 to compound 14 by acylation;

Step C8) converting compound 14 compound 19 by oxidation;

Step C9) converting compound 19 to compound 20 by oxidation;

Step C10) converting compound 20 to compound 21 by reduction and acylation, and Step C11) converting compound 21 to 8-O-debutanoyl-thapsigargin (22) by deprotection, oxidation and reduction,

SI-01

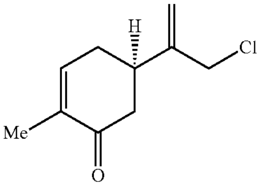

7

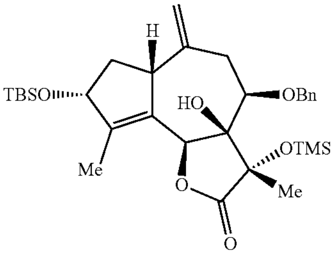

8

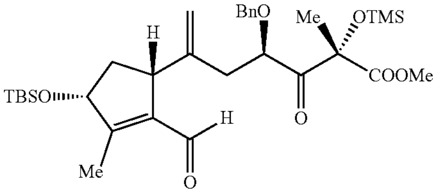

9

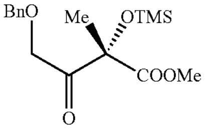

10

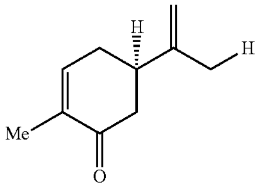

11

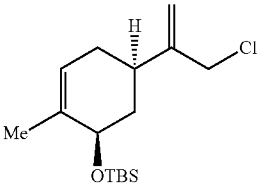

12

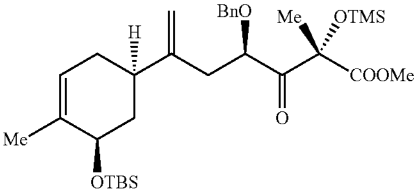

-continued

13

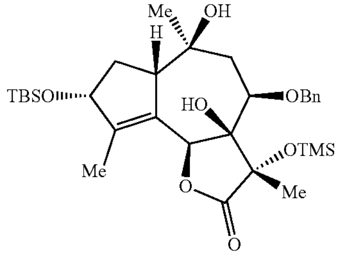

14

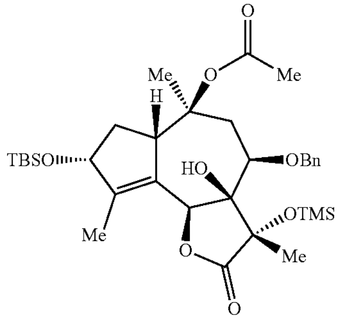

19

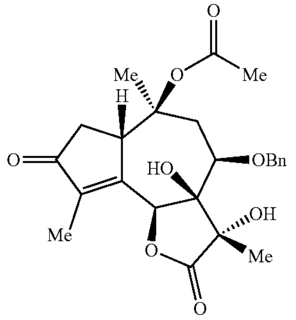

20

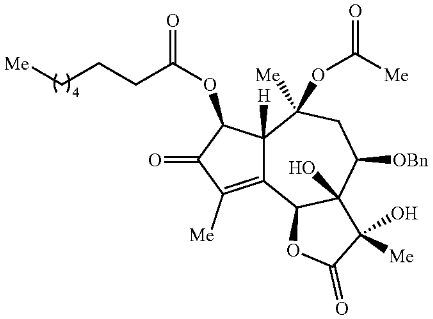

-continued

21

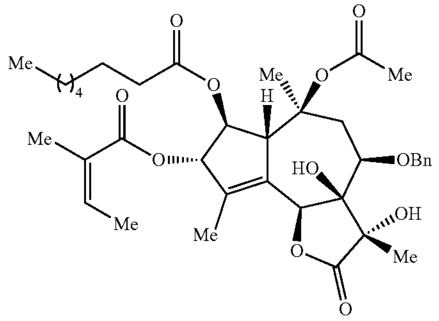

(22)

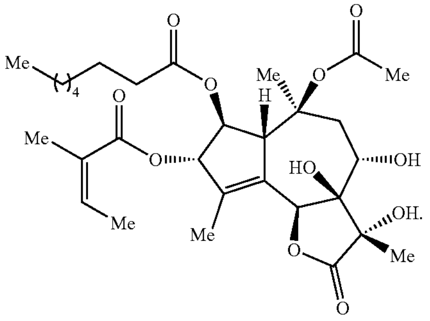

8-O-debutanoyl~thapsigargin

23. The method of claim 1, further comprising attaching a polypeptide or a linker suitable for attachment of an antibody, wherein the product is a compound of Formula III

III

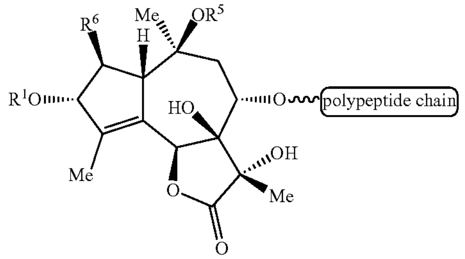

wherein $R^1$ and $R^5$ are independently acyl groups; $R^6$ is H or an acyloxyl group.

24. The method of claim 23, wherein the compound of Formula III is mipsagargin (5)

(5)

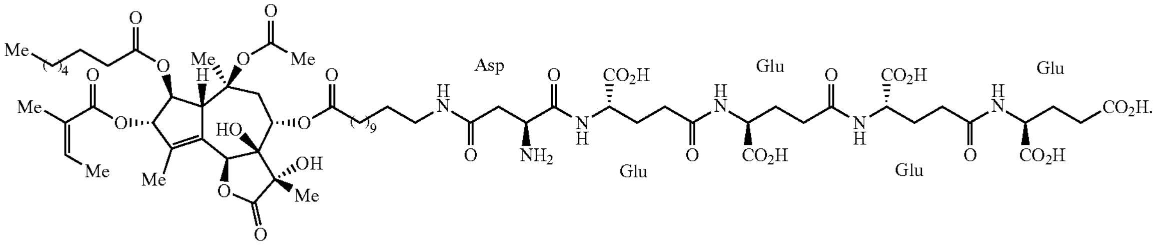

mipsagargin

25. The method of claim 1 wherein the compound of Formula I is DC-22-042 or a pharmaceutically acceptable salt thereof, comprising the steps of Step 1) converting compound 11 to DC-18-037 by asymmetric allylic coupling with lithium enolate of ketone 9 in the presence of lithium chloride and a chiral catalyst derived from $Pd_2(dba)_3.CHCl_3$ and (R)-BINAP followed by selective ozonolysis and an in situ intramolecular aldol condensation; and Step 2) converting compound DC-18-037 to DC-22-042 by reaction with $[V_2Cl_3(THF)_6]_2[Zn_2Cl_6]$

11

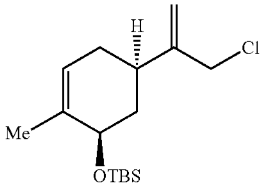

DC-18-037

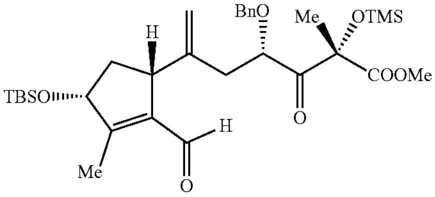

9

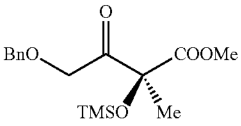

-continued

DC-22-042

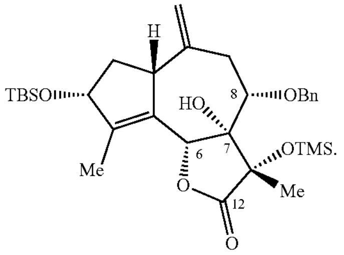

26. A method for synthesizing compound 12, comprising palladium-catalyzed coupling of compound 11 and compound 9

11

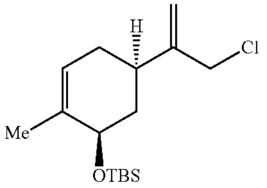

9

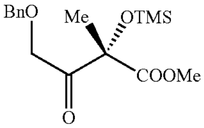

12

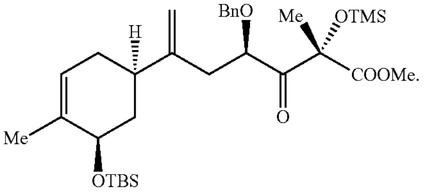

* * * * *